US012753168B2

(12) United States Patent
Allemann et al.

(10) Patent No.: US 12,753,168 B2
(45) Date of Patent: Oct. 6, 2026

(54) CCR6 RECEPTOR MODULATORS

(71) Applicant: Idorsia Pharmaceuticals Ltd, Allschwil (CH)

(72) Inventors: Oliver Allemann, Allschwil (CH); Eva Caroff, Allschwil (CH); Francis Hubler, Allschwil (CH); Emmanuel Meyer, Allschwil (CH)

(73) Assignee: Idorsia Pharmaceuticals Ltd, Allschwil (CH)

( * ) Notice: Subject to any disclaimer, the term of this patent is extended or adjusted under 35 U.S.C. 154(b) by 328 days.

(21) Appl. No.: 18/704,588

(22) PCT Filed: Oct. 25, 2022

(86) PCT No.: PCT/EP2022/079766
§ 371 (c)(1),
(2) Date: Apr. 25, 2024

(87) PCT Pub. No.: WO2023/072924
PCT Pub. Date: May 4, 2023

(65) Prior Publication Data

US 2025/0042881 A1 Feb. 6, 2025

(30) Foreign Application Priority Data

Oct. 26, 2021 (WO) ................. PCT/EP2021/079694

(51) Int. Cl.

| | |
|---|---|
| ***C07D 405/14*** | (2006.01) |
| ***A61K 31/4439*** | (2006.01) |
| ***A61K 31/4545*** | (2006.01) |
| ***C07D 401/14*** | (2006.01) |

(52) U.S. Cl.
CPC ........ *C07D 405/14* (2013.01); *A61K 31/4439* (2013.01); *A61K 31/4545* (2013.01); *C07D 401/14* (2013.01)

(58) Field of Classification Search
None
See application file for complete search history.

(56) References Cited

U.S. PATENT DOCUMENTS

| | | | | |
|---|---|---|---|---|
| 3,458,635 | A | 7/1969 | Lunsford et al. | |
| 3,479,370 | A | 11/1969 | Lunsford et al. | |
| 3,489,769 | A | 1/1970 | Helsley et al. | |
| 3,499,002 | A | 3/1970 | Helsley et al. | |
| 3,542,807 | A | 11/1970 | Lunsford et al. | |
| 3,651,085 | A | 3/1972 | Lunsford et al. | |
| 9,090,596 | B2 | 7/2015 | Musicki et al. | |
| 9,388,149 | B2 | 7/2016 | Musicki et al. | |
| 2003/0119806 | A1 * | 6/2003 | Lindell ................ | C07D 403/10 514/210.01 |
| 2014/0296254 | A1 | 10/2014 | Musicki et al. | |
| 2014/0309208 | A1 | 10/2014 | Musicki et al. | |
| 2015/0105366 | A1 | 4/2015 | Leonard et al. | |
| 2023/0174514 | A1 | 6/2023 | Allemann et al. | |
| 2025/0011313 | A1 | 1/2025 | Allemann et al. | |

FOREIGN PATENT DOCUMENTS

| | | | |
|---|---|---|---|
| CN | 103588697 | A | 2/2014 |
| GB | 1304650 | A | 1/1973 |
| WO | 1991/013359 | A1 | 9/1991 |
| WO | WO 1993/020063 | A1 | 10/1993 |
| WO | 1999/043664 | A1 | 9/1999 |
| WO | 2003/022808 | A1 | 3/2003 |
| WO | 2006/136830 | A1 | 12/2006 |
| WO | 2007/022351 | A2 | 2/2007 |
| WO | 2008/103426 | A1 | 8/2008 |
| WO | 2010/131145 | A1 | 11/2010 |
| WO | 2013/061004 | A1 | 5/2013 |
| WO | 2013/061005 | A1 | 5/2013 |
| WO | 2014/062658 | A1 | 4/2014 |
| WO | 2014/075580 | A1 | 5/2014 |
| WO | 2015/033299 | A1 | 3/2015 |
| WO | 2015/034820 | A1 | 3/2015 |
| WO | 2015/044900 | A1 | 4/2015 |

(Continued)

OTHER PUBLICATIONS

U.S. Appl. No. 19/136,271, filed Jun. 5, 2025, Fleischer et al.
Kulig, P. et al., "Efficacy of IDOR-1117-2520, a novel, orally available CCR6 antagonist in preclinical models of skin dermatitis," British Journal of Pharmacology, 2025, 24 pages, DOI: 10.1111/bph.70025.
Meyer, E. et al., "Discovery of the Clinical Candidate IDOR-1117-2520: A Potent and Selective Antagonist of CCR6 for Autoimmune Diseases," Journal of Medicinal Chemistry, 2024, 67, 8077-8098.
Meyer, E., "Discovery of the Clinical Candidate IDOR-1117-2520: A Potent and Selective Antagonist of CCR6 for Autoimmune Diseases," RICT Conference Presentation, 2024, 30 pages.

(Continued)

*Primary Examiner* — Kortney L. Klinkel
*Assistant Examiner* — Cierra M Rochelle
(74) *Attorney, Agent, or Firm* — Hoxie & Associates LLC

(57) ABSTRACT

The present invention relates to compounds of Formula (I), their synthesis and use as CCR6 receptor modulators for the prevention or treatment of e.g. inflammatory/autoimmune diseases/disorders and cancer.

Formula (I)

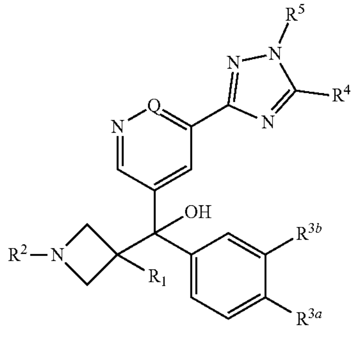

16 Claims, No Drawings

(56) References Cited

FOREIGN PATENT DOCUMENTS

| | | | |
|---|---|---|---|
| WO | 2015/057205 | A1 | 4/2015 |
| WO | 2015/057626 | A1 | 4/2015 |
| WO | 2015/084842 | A1 | 6/2015 |
| WO | 2017/087607 | A1 | 5/2017 |
| WO | 2019/036374 | A1 | 2/2019 |
| WO | 2019/105915 | A1 | 6/2019 |
| WO | 2019/136370 | A2 | 7/2019 |
| WO | 2019/147862 | A1 | 8/2019 |
| WO | 2020/058869 | A1 | 3/2020 |
| WO | 2021/219849 | A1 | 11/2021 |
| WO | 2023/057548 | A1 | 4/2023 |
| WO | 2023/073082 | A1 | 5/2023 |
| WO | WO 2024/121138 | A1 | 6/2024 |

OTHER PUBLICATIONS

Espacenet English abstract for CN103588697A, 1 page, retrieved on Sep. 25, 2024, from: https://worldwide.espacenet.com/patent/search/family/050079052/publication/CN103588697A?q=pn%3DCN103588697A.

Greene, T. et al., Protective Groups in Organic Synthesis, Third Edition, Wiley-Interscience, John Wiley & Sons, Inc., New York, 1999.

Sucur, A. et al., "Combined manual and automated immunophenotypisation identified disease-specific peripheral blood immune subpopulations in rheumatoid arthritis, ankylosing spondylitis and psoriatic arthritis," Clinical and Experimental Rheumatology, 2019, 17 pages.

Tanis, V. et al., "3-Substituted Quinolines as RORγt Inverse Agonists," Bioorganic & Medicinal Chemistry Letters, 2019, 29, 1463-1470.

Tawaraisha, T. et al., "Identification of a novel series of potent and selective CCR6 inhibitors as biological probes," Bioorganic & Medicinal Chemistry Letters, 2018, 28, 3067-3072.

Tsaur, I. et al., "CCL2 Chemokine as a Potential Biomarker for Prostate Cancer: A Pilot Study," Cancer Research and Treatment, 2015, 47(2), 306-312.

Uchida, K. et al., "The Increased Expression of CCL20 and CCR6 in Rectal Mucosa Correlated to Severe Inflammation in Pediatric Ulcerative Colitis," Gastroenterology Research and Practice, 2015, 856532, 6 pages, http://dx.doi.org/10.1155/2015/856532.

Van Hamburg, J. et al., "Th17 Cells, but Not Th1 Cells, From Patients With Early Rheumatoid Arthritis are Potent Inducers of Matrix Metalloproteinases and Proinflammatory Cytokines Upon Synovial Fibroblast Interaction, Including Autocrine Interleukin-17A Production," Arthritis & Rheumatism, 2011, 63(1), 73-83.

Van Langelaar, J. et al., "T helper 17.1 cells associate with multiple sclerosis disease activity: perspectives for early intervention," Brain, 2018, 141, 1334-1349.

Varona, R. et al., "CCR6 has a non-redundant role in the development of inflammatory bowel disease," European Journal of Immunology, 2003, 33, 2937-2946.

Vlahos, C. et al., "A Specific Inhibitor of Phosphatidylinositol 3-Kinase, 2-(4-Morpholinyl)-8-phenyl-4H-1-benzopyran-4-one (LY294002)," The Journal of Biological Chemistry, 1994, 269(7), 5241-5248.

Wallace, A. et al., "Chemokine (C—C) motif ligand 20 is regulated by PGF2α-F-prostanoid receptor signalling in endometrial adenocarcinoma and promotes cell proliferation," Molecular and Cellular Endocrinology, 2011, 331, 129-135.

Wang, G. et al., "Tobacco smoke induces production of chemokine CCL20 to promote lung cancer," Cancer Letters, 2015, 363, 60-70.

Wang, L. et al., "Overexpression of CCL20 and its receptor CCR6 predicts poor clinical prognosis in human gliomas," Medical Oncology, 2012, 29, 3491-3497.

Wang, L-x. et al., "Network-based co-expression analysis for exploring the potential diagnostic biomarkers of metastatic melanoma," PLoS ONE, 2018, 13(1), e0190447, 16 pages, https://doi.org/10.1371/journal.pone.0190447.

Wu, Q. et al., "Blocking Triggering Receptor Expressed on Myeloid Cells-1-Positive Tumor-Associated Macrophages Induced by Hypoxia Reverses Immunosuppression and Anti-Programmed Cell Death Ligand 1 Resistance in Liver Cancer," Hepatology, 2019, 70(1), 198-214.

Yu, S. et al., "Is CCR6 Required for the Development of Psoriasiform Dermatitis in Mice?," HHS Public Access, Author Manuscript, available in PMC 2019, 6 pages, doi:10.1016/j.jid.2018.07.036, front page starts: Published in final edited form as: J Invest Dermatol. 2019; 139(2): 485-488.

Zhang, C-y. et al., "The role of CCL20/CCR6 axis in recruiting Treg cells to tumor sites of NSCLC patients," Biomedicine & Pharmacotherapy, 2015, 69, 242-248.

Zhang, X-P. et al., "Role of CCL20/CCR6 and the ERK signaling pathway in lung adenocarcinoma," Oncology Letters, 2017, 14, 8183-8189.

Zhao, X. et al., "Synergistic association of FOXP3+ tumor infiltrating lymphocytes with CCL20 expressions with poor prognosis of primary breast cancer," Medicine, 2019, 98(50), e18403, 11 pages.

Zhong, W. et al., "CCR6+ Th cell distribution differentiates systemic lupus erythematosus patients based on anti-dsDNA antibody status," PeerJ, 2018, 6, e4294, 19 pages.

Zhu, C-c. et al., "CCR6 promotes tumor angiogenesis via the AKT/NF-KB/VEGF pathway in colorectal cancer," BBA—Molecular Basis of Disease, 2018, 1864, 387-397.

U.S. Appl. No. 17/997,531, filed Oct. 28, 2022, Allemann et al.

U.S. Appl. No. 18/705,346, filed Apr. 26, 2024, Allemann et al.

Kang, M. et al., "Interleukin-17 in Various Ocular Surface Inflammatory Diseases," Journal of Korean Medical Science, 2011, 26, 938-944.

Kenna, T. et al., "Enrichment of Circulating Interleukin-17-Secreting Interleukin-23 Receptor-Positive γ/δ T Cells in Patients With Active Ankylosing Spondylitis," Arthritis & Rheumatism, 2012, 64(5), 1420-1429.

Kirshberg, S. et al., "Involvement of CCR6/CCL20/IL-17 Axis in NSCLC Disease Progression," PLoS ONE, 2011, 6 (9), e24856, 10 pages, doi:10.1371/journal.pone.0024856.

Kleeff, J. et al., "Detection and Localization of MIP-3a/Larc/Exodus, a Macrophage Proinflammatory Chemokine, and Its CCR6 Receptor in Human Pancreatic Cancer," International Journal of Cancer, 1999, 81, 650-657.

Kohl, N. et al., "Inhibition of farnesyltransferase induces regression of mammary and salivary carcinomas in ras transgenic mice," Nature Medicine, 1995, 1(8), 792-797.

Kohler, R. et al., "A role for Macrophage Inflammatory Protein-3a/CC Chemokine Ligand 20 in Immune Priming During T Cell-Mediated Inflammation of the Central Nervous System," The Journal of Immunology, 2003, 170, 6298-6306.

Kwon, J. et al., "Colonic epithelial cells are a major site of macrophage inflammatory protein 3α(MIP-3α) production in normal colon and inflammatory bowel disease," Gut, 2002, 51, 818-826.

Lee, A. et al., "Expression of CCR6 on B cells in systemic lupus erythematosus patients," Clinical Rheumatology, 2017, 36, 1453-1456.

Lee, H-J. et al., "Increased Expression of MIP-3α/CCL20 in Peripheral Blood Mononuclear Cells From Patients With Ulcerative Colitis and Its Down-regulation by Sulfasalazine and Glucocorticoid Treatment," Inflammatory Bowel Diseases, 2005, 11(12), 1070-1079.

Lee, J-J. et al., "Enrichment of Human CCR6+ Regulatory T Cells with Superior Suppressive Activity in Oral Cancer," The Journal of Immunology, 2017, 199, 467-476.

Lee, S. et al., "Human antigen R-regulated CCL20 contributes to osteolytic breast cancer bone metastasis," Scientific Reports, 2017, 7, 9610, 13 pages, doi:10.1038/s41598-017-09040-4.

Leipe, J. et al., "Role of Th17 Cells in Human Autoimmune Arthritis," Arthritis & Rheumatism, 2010, 62(10), 2876-2885.

Lin, Y-L. et al., "CCR6 Deficiency Impairs IgA Production and Dysregulates Antimicrobial Peptide Production, Altering the Intestinal Flora," Frontiers in Immunology, 2017, 8(805), 20 pages, doi:10.3389/fimmu.2017.00805.

Liu, J. et al., "Tumor-Associated Macrophages Recruit CCR6+ Regulatory T Cells and Promote the Development of Colorectal

(56) References Cited

OTHER PUBLICATIONS

Cancer via Enhancing CCL20 Production in Mice," PLoS ONE, 2011, 6(4), e19495, 13 pages, doi:10.1371/journal.pone/0019495.
Liu, J. et al., "CCR6 Is a Prognostic Marker for Overall Survival in Patients with Colorectal Cancer, and Its Overexpression Enhances Metastasis In Vivo," PLoS ONE, 2014, 9(6), e101137, 13 pages, doi:10.1371/journal.pone.0101137.
Liu, W. et al., "Cisplatin-stimulated macrophages promote ovarian cancer migration via the CCL20-CCR6 axis," Cancer Letters, 2020, 472, 59-69.
Lu, E. et al., "CCL20/CCR6 promotes cell proliferation and metastasis in laryngeal cancer by activating p38 pathway," Biomedicine & Pharmacotherapy, 2017, 85, 486-492.
Mabuchi, T. et al., "Chemokine receptors in the pathogenesis and therapy of psoriasis," Journal of Dermatological Science, 2012, 65, 4-11.
Marsigliante, S. et al., "Paracrine CCL20 Loop Induces Epithelial-Mesenchymal Transition In Breast Epithelial Cells," Molecular Carcinogenesis, 2016, 55, 1175-1186.
Matsui, T. et al., "Selective recruitment of CCR6-expressing cells by increased production of MIP-3α in rheumatoid arthritis," Clinical and Experimental Immunology, 2001, 125, 155-161.
Maung, H. et al., "Common Transcription Programs and the Role of Chemokine (C—C Motif) Ligand 20 (CCL20) in Cell Migration of Cholangiocarcinoma," EXCLI Journal, 2020, 19, 154-166.
Mays, A. et al., "Chemokine and Chemokine Receptor Profiles in Metastatic Salivary Adenoid Cystic Carcinoma," Anticancer Research, 2016, 36, 4013-4018.
Meares, G. et al., "Regulation of CCL20 Expression in Astrocytes by IL-6 and IL-17," GLIA, 2012, 60, 771-781.
Meissner, A. et al., "CC chemokine ligand 20 partially controls adhesion of naive B cells to activated endothelial cells under shear stress," Blood, 2003, 102, 2724-2727.
Melis, L. et al., "Systemic Levels of IL-23 are strongly associated with disease activity in rheumatoid arthritis but not spondyloarthritis," Annals of the Rheumatic Diseases, 2010, 69, 618-623.
Miyagaki, T. et al., "IL-22, but not IL-17, Dominant Environment in Cutaneous T-cell Lymphoma," Clinical Cancer Research, 2011, 17(24), 7529-7538.
Moller, C. et al., "Expression and function of chemokine receptors in human multiple myeloma," Leukemia, 2003, 17 (1), 203-210.
Montresor, A. et al., "Chemokines and the signaling modules regulating integrin affinity," Frontiers in Immunology, 2012, 3(127), 10 pages, doi:103389/fimmu.2012.00127.
Mony, J. et al., "Chemokine receptor expression by inflammatory T cells in EAE," Frontiers in Cellular Neuroscience, 2014, 8(187), 9 pages, doi: 10.3389/fncel.2014.00187.
Moody, S. et al., "Novel GPR34 and CCR6 mutation and distinct genetic profiles in MALT lymphomas of different sites," Haematologica, 2018, 103(8), 1329-1336.
Mrizak, D. et al., "Effects of Nasopharyngeal Carcinoma-Derived Exosomes on Human Regulatory T Cells," Journal of the National Cancer Institute, 2015, 107(1), 363, 13 pagesm doi:10.1093/jnci/dju363.
Nandi, B. et al., "CCR6, the Sole Receptor for the Chemokine CCL20, Promotes Spontaneous Intestinal Tumorigenesis," PLoS ONE, 2014, 9(5), e97566, 10 pages, coiL10.1371/journal/pone.0097566.
Nistala, K. et al., "Interleukin-17-Producing T Cells are Enriched in the Joints of Children With Arthritis, but Have a Reciprocal Relationship to Regulatory T Cell Numbers," Arthritis & Rheumatism, 2008, 58(3), 875-887.
Papp, K. et al., "Brodalumab, an Anti-Interleukin-17-Receptor Antibody for Psoriasis," The New England Journal of Medicine, 2012, 366(13), 1181-1189.
Paul, C. et al., "Efficacy, safety and usability of secukinumab administration by autoinjector/pen in psoriasis: a randomized, controlled trial (Juncture)," Journal of the European Academy of Dermatology and Venereology, 2015, 29, 1082-1090.
Ranasinghe, R. et al., "Modulation of the CCR6-CCL20 Axis: A Potential Therapeutic Target in Inflammation and Cancer," Medicina, 2018, 54, 88, 12 pages, doi:10.3390/medicina54050088.
Reboldi, A. et al., "C—C chemokine receptor 6-regulated entry of TH-17 cells into the CNS through the choroid plexus is required for the initiation of EAE," Nature Immunology, 2009, 10(5), 514-523.
Reboldi, A. et al., "IgA production requires B cell interaction with subepithelial dendritic cells in Peyer's patches," HHS Public Access, Author Manuscript, available in PMC 2016, 25 pages, doi:10.1126/science.aaf4822, front page states: Published in final edited form as: Science. 2016; 352(6287): aaf4822.
Reich, K. et al., "Guselkumab versus secukinumab for the treatment of moderate-to-severe psoriasis (Eclipse): results from a phase 3, randomised controlled trial," Lancet, 2019, 394, 831-839.
Robert, R. et al., "Essential role for CCR6 in certain inflammatory diseases demonstrated using specific antagonist and knockin mice," JCI Insight, 2017, 2(15), e94821, 17 pages, https://doi.org/10.1172/jci.insight.94821.
Rubie, C. et al., "Chemokine expression in hepatocellular carcinoma versus colorectal liver metastases," World Journal of Gastroenterology, 2006, 12(41), 6627-6633.
Rubie, C. et al., "CCL20/CCR6 expression profile in pancreatic cancer," Journal of Translational Medicine, 2010, 8 (45), 8 pages, doi: 10.1186/1479-5876-8-45.
Sausville, E., "Cyclin-Dependent Kinase Modulators Studied at the NCI: Pre-Clinical and Clinical Studies," Current Medicinal Chemistry—Anti-Cancer Agents, 2003, 3, 47-56.
Schutyser, E. et al., "The CC chemokine CCL20 and its receptor CCR6," Cytokine & Growth Factor Reviews, 2003, 14, 409-426.
Sekulic, A. et al., "A Direct Linkage between the Phosphoinositide 3-Kinase-AKT Signaling Pathway and the Mammalian Target of Rapamycin in Mitogen-stimulated and Transformed Cells," Cancer Research, 2000, 60, 3504-3513.
Shen, H. et al., "Frequency and Phenotype of Peripheral Blood Th17 Cells in Ankylosing Spondylitis and Rheumatoid Arthritis," Arthritis & Rheumatism, 2009, 60(6), 1647-1656.
Singh, S. et al., "Human T Cells That are Able to Produce IL-17 Express the Chemokine Receptor CCR6," The Journal of Immunology, 2008, 180, 214-221.
Skepner, J. et al., "Pharmacologic Inhibition of RORγt Regulates Th17 Signature Gene Expression and Suppresses Cutaneous Inflammation In Vivo," The Journal of Immunology, 2014, 192, 2564-2575.
Skovdahl, H. et al., "Expression of CCL20 and Its Corresponding Receptor CCR6 Is Enhanced in Active Inflammatory Bowel Disease, and TLR3 Mediates CCL20 Expression in Colonic Epithelial Cells," PLoS ONE, 2015, 10 (11), e0141710, 17 pages, doi:10.1371/journal.pone.1041710.
Suan, D. et al., "CCR6 Defines Memory B Cell Precursors in Mouse and Human Germinal Centers, Revealing Light-Zone Location and Predominant Low Antigen Affinity," Immunity, 2017, 47(6), 1142-1153.
Abe, F. et al., "Histone deacetylase inhibitors inhibit metastasis by restoring a tumor suppressive microRNA-150 in advanced cutaneous T-cell lymphoma," Oncotarget, 2017, 8(5), 7572-7585.
Abraham, M. et al., "Natural and induced immunization against CCL20 ameliorate experimental autoimmune encephalitis and may confer protection against multiple sclerosis," Clinical Immunology, 2017, 183, 316-324.
Acosta-Rodriguez, E. et al., "Surface phenotype and antigenic specificity of human interleukin 17-producing T helper memory cells," Nature Immunology, 2007, 8(6), 639-646.
Al-Mossawi, M. et al., "Unique transcriptome signatures and GM-CSF expression in lymphocytes from patients with spondyloarthritis," Nature Communications, 2017, 8(1510), 11 pages, doi: 10.1038/s41467-017-01771-2.
Baeten, D. et al., "Secukinumab, an Interleukin-17A Inhibitor, in Ankylosing Spondylitis," The New England Journal of Medicine, 2015, 373(26), 2534-2548.
Blokland, S. et al., "Decreased circulating CXCR3 + CCR9+T helper cells are associated with elevated levels of their ligands CXCL10 and CCL25 in the salivary gland of patients with Sjogren's

(56) References Cited

OTHER PUBLICATIONS syndrome to facilitate their concerted migration," Scandinavian Journal of Immunology, 2020, 91, e12852, 8 pages, https://doi.org/10.1111/sji.12852.
Bonelli, M. et al., "CCR6 controls autoimmune but not innate immunity-driven experimental arthritis," Journal of Cellular and Molecular Medicine, 2018, 22, 5278-5285.
Buhl, T. et al., "Molecular and Morphological Characterization of Inflammatory Infiltrate in Rosacea Reveals Activation of Th1/Th17 Pathways," Journal of Investigative Dermatology, 2015, 135, 2198-2208.
Campbell, J. et al., "IL-17-Secreting γδ T Cells are Completely Dependent upon CCR6 for Homing to Inflamed Skin," The Journal of Immunology, 2017, 199, 3129-3136.
Campbell, J. et al., "Efficacy of Chemokine Receptor Inhibition in Treating IL-36α-Induced Psoriasiform Inflammation," The Journal of Immunology, 2019, 202, 1687-1692.
Castro, G. et al., "RORγt and RORα signature genes in human Th17 cells," PLoS ONE, 2017, 12(8), e0181868, 22 pages, https://doi.org/10.1371/journal.pone.0181868.
Chabaud, M. et al., "Enhancing Effect of IL-1, IL-17, and TNF-α on Macrophage Inflammatory Protein-3α Production in Rheumatoid Arthritis: Regulation by Soluble Receptors and Th2 Cytokines," The Journal of Immunology, 2001, 167, 6015-6020.
Chang, H. et al., "CCR6 is a Predicting Biomarker of Radiosensitivity and Potential Target of Radiosensitization in Rectal Cancer," Cancer Research and Treatment, 2018, 50(4), 1203-1213.
Chen, W. et al., "CCL20 triggered by chemotherapy hinders the therapeutic efficacy of breast cancer," PLoS Biology, 2018, 16(7), e2005869, 27 pages, https://doi.org/10.1371/journal.pbio.2005869.
Chevrel, G. et al., "Addition of interleukin 1 (IL1) and IL17 soluble receptors to a tumour necrosis factor a soluble receptor more effectively reduces the production of IL6 and macrophage inhibitory protein-3α and increases that of collagen in an in vitro model of rheumatoid synoviocyte activation," Annals of the Rheumatic Diseases, 2002, 61, 730-733.
Chew, V. et al., "Delineation of an immunosuppressive gradient in hepatocellular carcinoma using high-dimensional proteomic and transcriptomic analyses," Proceedings of the National Academy of Sciences of the United States of America, 2017, PNAS Early Edition, 10 pages, www.pnas.org/cgi/doi/10.1073/pnas.1706559114.
Cohen, S. et al., "Rituximab for Rheumatoid Arthritis Refractory to Ant-Tumor Necrosis Factor Therapy," Arthritis & Rheumatism, 2006, 54(9), 2793-2806.
Cook, D. et al., "CCR6 Mediates Dendritic Cell Localization, Lymphocyte Homeostasis, and Immune Responses in Mucosal Tissue," Immunity, 2000, 12, 495-503.
Coperchini, F. et al., "TNF-α increases the membrane expression of the chemokine receptor CCR6 in thyroid tumor cells, but not in normal thyrocytes: potential role in the metastatic spread of thyroid cancer," Tumor Biology, 2016, 37, 5569-5575.
Cua, D. et al., "Innate IL-17-producing cells: the sentinels of the immune system," Nature Reviews Immunology, 2010, 10, 479-489.
Dellacasagrande, J. et al., "Liver Metastasis of Cancer Facilitated by Chemokine Receptor CCR6," Scandinavian Journal of Immunology, 2003, 57, 534-544.
Ding, X. et al., "High Expression of CCL20 Is Associated with Poor Prognosis in Patients with Hepatocellular Carcinoma after Curative Resection," Journal of Gastrointestinal Surgery, 2012, 16, 828-836.
Dohlman, T. et al., "The CCR6/CCL20 Axis Mediates Th17 Cell Migration to the Ocular Surface in Dry Eye Disease," Investigative Ophthalmology & Visual Science, 2013, 54(6), 4081-4091.
Dolcino, M. et al., "Gene Expression Profiling in Peripheral Blood Cells and Synovial Membranes of Patients with Psoriatic Arthritis," PLoS ONE, 2015, 10(6), e0128262, 33 pages, doi:10.1371/journal.pone.0128262.
El Sharkawi, F. et al., "The combined effect of IL-17F and CCL20 gene polymorphism in susceptibility to multiple sclerosis in Egypt," Gene, 2019, 685, 164-169.
Elgueta, R. et al., "CCR6-Dependent Positioning of Memory B Cells Is Essential for Their Ability to Mount a Recall Response to Antigen," The Journal of Immunology, 2015, 194, 9 pages, doi:10.4049/jimmunol.1401553.
Elhofy, A. et al., "Mice deficient for CCR6 fail to control chronic experimental autoimmune encephalomyelitis," NIH Public Access, Author Manuscript, available in PMC 2010, 19 pages, doi:10.1016/j.jneuroim.2009.05.011, front page states: Published in final edited form as: J Neuroimmunol. 2009; 213(1-2): 91-99.
Getschman, A. et al., "Protein engineering of the chemokine CCL20 prevents psoriasiform dermatitis in an IL-23-dependent murine model," Proceedings of the National Academy of Sciences of the United States of America, 2017, 114(47), 12460-12465.
Ghadjar, P. et al., "Chemokine receptor CCR6 expression level and aggressiveness of prostate cancer," Journal of Cancer Research and Clinical Oncology, 2008, 134, 1181-1189.
Giuliani, N. et al., "CC-Chemokine Ligand 20/Macrophage Inflammatory Protein-3α and CC-Chemokine Receptor 6 are Overexpressed in Myeloma Microenvironment Related to Osteolytic Bone Lesions," Cancer Research, 2008, 68 (16), 6840-6850.
Goldstein, N. et al., "Biological Efficacy of a Chimeric Antibody to the Epidermal Growth Factor Receptor in a Human Tumor Xenograft Model," Clinical Cancer Research, 1995, 1, 1311-1318.
Greaves, D. et al., "CCR6, a CC Chemokine Receptor that Interacts with Macrophage Inflammatory Protein 3α and Is Highly Expressed in Human Dendritic Cells," Journal of Experimental Medicine, 1997, 186(6), 837-844.
Guo, W. et al., "DEPDC1 drives hepatocellular carcinoma cell proliferation, invasion and angiogenesis by regulating the CCL20/CCR6 signaling pathway," Oncology Reports, 2019, 15 pages, DOI: 10.3892/or.2019.7221.
Harasawa, H. et al., "Survey of chemokine receptor expression reveals frequent co-expression of skin-homing CCR4 and CCR10 in adult T-cell leukemia/lymphoma," Leukemia & Lymphoma, 2006, 47(10), 2163-2173.
Harper, E. et al., "Th17 Cytokines Stimulate CCL20 Expression in Keratinocytes In Vitro and In Vivo: Implications for Psoriasis Pathogenesis," NIH Public Access, Author Manuscript, available in PMC 2010, 16 pages, doi:10.1038/jid.2009.65, front page states: Published in final edited form as: J Invest Dermatol. 2009; 129(9): 2175-2183.
Hashikawa, H. et al., "Microarray analysis of gene expression by microdissected epidermis and dermis in mycosis fungoides and adult T-cell leukemia/lymphoma," International Journal of Oncology, 2014, 45, 1200-1208.
Hattori, T. et al., "Gene Expression Profiling of IL-17A-Treated Synovial Fibroblasts from the Human Temporomandibular Joint," Mediators of Inflammation, 2015, Article ID 436067, 12 pages, http://dx.doi.org/10.1155/2015/436067.
He, H. et al., "CCR6+ B lymphocytes responding to tumor cell-derived CCL20 support hepatocellular carcinoma progression via enhancing angiogenesis," American Journal of Cancer Research, 2017, 7(5), 1151-1163 and supplementary pp. 1-3.
Hedrick, M. et al., "CCR6 as a possible therapeutic target in psoriasis," NIH Public Access, Author Manuscript, available in PMC 2013, 19 pages, doi:10.1517/14728222.2010.504716, front page states: Published in final edited form as: Expert Opin Ther Targets. 2010; 14(9): 911-922.
Hedrick, M. et al., "CCR6 is required for IL-23-induced psoriasis-like inflammation in mice," The Journal of Clinical Investigation, 2009, 119(8), 2317-2329.
Hirota, K. et al., "Preferential recruitment of CCR6-expressing Th17 cells to inflamed joints via CCL20 in rheumatoid arthritis and its animal model," The Journal of Experimental Medicine, 2007, 204(12), 2803-2812.
Ikeda, S. et al., "Disruption of CCL20-CCR6 interaction inhibits metastasis of advanced cutaneous T-cell lymphoma," Oncotarget, 2016, 7(12), 13563-13574.
Ito, M. et al., "MicroRNA-150 inhibits tumor invasion and metastasis by targeting the chemokine receptor CCR6, in advanced cutaneous T-cell lymphoma," Blood, 2014, 123(10), 1499-1511.

(56) References Cited

OTHER PUBLICATIONS

Ivanov, I. et al., "The Orphan Nuclear Receptor RORγt Directs the Differentiation Program of Proinflammatory IL-17+ T Helper Cells," Cell, 2006, 126, 1121-1133.
Iwamoto, S. et al. "TNF-α is essential in the induction of fatal autoimmune hepatitis in mice through upregulation of hepatic CCL20 expression," Clinical Immunology, dated 2013, 39 pages, retrieved from Kyoto University Research Information Repository: http://hdl.handle.net/2433/168391.
Jin, P. et al., "Astrocyte-derived CCL20 reinforces HIF-1-mediated hypoxic responses in glioblastoma by stimulating the CCR6-NF-kB signaling pathway," Oncogene, 2018, 37, 3070-3087.
Kadomoto, S. et al., "Tumor-Associated Macrophages Induce Migration of Renal Cell Carcinoma Cells via Activation of the CCL20-CCR6 Axis," Cancers, 2019, 12, 89, doi:10.3390/cancers12010089, 13 pages.
Remington, The Science and Practice of Pharmacy, 21st Edition, Part 5, "Pharmaceutical Manufacturing," published by Lippincott Williams & Wilkins, 2005.
Stahl, P. et al., Eds., Handbook of Pharmaceutical Salts. Properties, Selection and Use, Wiley-VCH, Weinheim, 2008.
Wouters, J. et al., Eds., Pharmaceutical Salts and Co-crystals, RSC Publishing, 2012.

* cited by examiner

CCR6 RECEPTOR MODULATORS

CROSS REFERENCE TO RELATED APPLICATIONS

This application is a National Stage Entry under 35 U.S.C. § 371 of International Application No. PCT/EP2022/079766 filed Oct. 25, 2022, which claims priority to International Application No. PCT/EP2021/079694 filed Oct. 26, 2021, the contents of each of which are hereby incorporated by reference in their entireties.

The present invention relates to novel compounds of Formula (I), or pharmaceutically acceptable salts thereof, and their use as CCR6 receptor modulators in the treatment or prevention of various diseases, conditions or disorders ameliorated by modulating said receptor. Furthermore, the present invention concerns related aspects such as pharmaceutical compositions containing one or more compounds of Formula (I) and processes for the preparation of said compounds.

Chemokine receptors comprise a family G-protein coupled receptors (GPCRs) that recognize and bind to peptide chemokine ligands. The predominant functions of chemokine receptors and their ligands are to induce leukocyte trafficking to-and-from lymphoid organs and tissues in the steady state, as well as in the context of an infection or inflammation. Additionally, chemokine signaling events can induce the activation of integrin molecules on the surface of immune cells, allowing firm adhesion to activated endothelium, facilitating migration from blood into inflamed tissue (Montresor A, Frontiers in Imm., 2012; Meissner A, Blood, 2003). Chemokine receptor 6 (CCR6, aliases BN-1, C—C CKR-6, CD196, CKRL3, CMKBR6, DCR2, DRY6, GPR29, GPRCY4, STRL22) is a GPCR mainly expressed on effector CD4+T helper cells, but is also present on B cells, CD8+ cytotoxic T cells, regulatory T cells (Treg), immature dendritic cells (DC) and type 3 innate lymphoid cells (ILC3) (Cua D J, Nat Rev Immunol. 2010 July; 10(7):479-89. doi: 10.1038/nri2800). CCR6 binds to the chemokine CCL20 (chemokine (C—C motif) ligand 20) (Greaves D R, J Exp Med. 1997 Sep. 15; 186(6):837-44. doi: 10.1084/jem.186.6.837.). CCL20 is also called macrophage inflammatory protein 3a (MIP-3a), liver and activation-regulated chemokine (LARC), or Exodus-1 (Schutyser E, Cytokine Growth Factor Rev. 2003 October; 14(5):409-26. doi: 10.1016/s1359-6101(03)00049-2). CCR6/CCL20 interactions dictate the humoral response in the intestinal mucosa and are required for lymphocyte homeostasis in the mucosa of the small intestine (Cook D N, Immunity. 2000 May; 12(5):495-503. doi: 10.1016/s1074-7613(00)80201-0). Under steady state conditions, CCR6 and CCL20 regulate production of IgA in the intestine, where CCL20 expressed in Peyer's patches guides CCR6+IgA+B cells to the mucosa and secretory IgA can be released into the gut lumen (Lin Y L, Front Immunol. 2017; 8:805. doi: 10.3389/fimmu.2017.00805; Reboldi A, Science. 2016 May 13; 352(6287):aaf4822. doi: 10.1126/science.aaf4822). Under inflammatory conditions, expression of CCL20 is highly upregulated by proinflammatory cytokines including IL-17A, TNFa and IL-1b in both endothelial and epithelial cells (Harper E G, J Invest Dermatol. 2009 September; 129(9):2175-83. doi: 10.1038/jid.2009.65; PLoS One. 2015; 10(11):e0141710. doi: 10.1371/journal.pone.0141710) and tissue fibroblasts (Hattori T, Mediators Inflamm. 2015; 2015:436067. doi: 10.1155/2015/436067). Interleukin (IL)-17A expression is restricted to cells expressing the transcription factor RORgt (Cell. 2006 Sep. 22; 126(6):1121-33. doi: 10.1016/j.cell.2006.07.035). IL-17A expression has been shown to segregate with CCR6 expression on human T cells (Singh S P, J Immunol. 2008 Jan. 1; 180(1):214-21. doi: 10.4049/jimmunol.180.1.214; Nat Immunol. 2007 June; 8(6):639-46. doi: 10.1038/ni1467). CCR6 was also described as a target gene of RORgt (PLoS One. 2017; 12(8):e0181868. doi: 10.1371/journal.pone.0181868; Skepner J, J Immunol. 2014 Mar. 15; 192(6):2564-75. doi: 10.4049/jimmunol.1302190), thus clarifying the co-expression of IL-17A and CCR6 in RORgt+ cell types.

Certain disclosures in the prior art may be regarded as relating to modulation of CCR6. For instance, Tawaraishia et al. (Bioorganic & Medicinal Chemistry Letters, Volume 28, Issue 18, 2018, Pages 3067-3072, ISSN 0960-894X, https://doi.org/10.1016/j.bmcl.2018.07.042) disclose a series of benzenesulfonyl-aminocyclohexane derivatives as selective CCR6 inhibitors. CN103588697 teaches sulfonamide derivatives as CCR6 antagonists and their use in treating CCR6-mediated diseases such as autoimmune diseases, inflammation, psoriasis, multiple sclerosis or cancer. WO2014/075580 describes the use of aurintricarboxylic acid for targeting chemokine receptors. WO2015/084842 teaches certain sulfonamides which may be used in treating CCR6 related diseases. WO2017/087607, WO2010/131145, WO2013/061004, WO2013/061005, WO2019/036374 and WO2020/058869 provide certain cyclobutenediones for use in the treatment of chemokine/CCR6 related diseases. WO2019/136370 teaches a method of treating a certain type of psoriasis. WO2019/147862 proposes azetidine derivatives which may be used as chemokine modulators. WO2021219849 relates to certain CCR6 receptor modulators.

Further, WO1999/43664 discloses certain pyrrolidinones with anti-inflammatory and analgesic properties. In WO2019/105915 certain heterocyclic compounds are provided which may be used as MAGL inhibitors. WO2015/057626, US2015/0105366, WO2014/062658, WO2015/057205 and Tanis V M et al. (Bioorg Med Chem Lett. 2019 Jun. 15; 29(12):1463-1470. doi: 10.1016/j.bmcl.2019.04.021) relate to modulators of the RORγt receptor which may be used in treating rheumatoid arthritis or psoriasis. WO03/022808 proposes certain azetidine derivatives for use as pesticides. WO2008/103426 and WO2007/022351 disclose certain quaternary ammonium compounds useful as muscarinic receptor antagonists. WO2006/136830 teaches certain heteroaryl-alkylamines as protein kinase inhibitors. WO91/13359 proposes heterocyclic cholinergic enhancers. U.S. Pat. No. 3,458,635 teaches certain pyrrolidines which may be used for treating depression. GB 1304650 discloses spasmolytic pyrrolidines. U.S. Pat. Nos. 3,479,370, 3,489,769, 3,499,002, 3,542,807 and 3,651,085 relate to certain pyrrolidines with analgesic/tranquilizing activity.

The present CCR6 modulators may be useful, alone, or in combination in the treatment or prevention of the following diseases or disorders: Rheumatoid arthritis (RA) causes chronic inflammation of the joints and chemokines regulate infiltration of the inflamed synovium by inflammatory cells. RA is characterized by the increased release of CCL20 and the subsequent recruitment of CCR6+ T cells to the inflamed joints. CCL20 is highly expressed in the synovial fluid of RA (Hirota, J Exp Med. 2007 Nov. 26; 204(12):2803-12. doi: 10.1084/jem.20071397; Matsui T, Clin Exp Immunol. 2001 July; 125(1):155-61. doi: 10.1046/j.1365-2249.2001.01542.x). In patients with RA, CCR6+Th cells have been found in the inflamed synovium and increased proportions of peripheral blood CCR6+Th cells have been found in patients with early RA (van Hamburg J P, Arthritis Rheum. 2011 January; 63(1):73-83. doi: 10.1002/art.30093; Leipe J Arthritis Rheum. 2010 October; 62(10):2876-85. doi: 10.1002/art.27622; Nistala K, Arthritis Rheum. 2008 March; 58(3):875-87. doi: 10.1002/art.23291). The production of CCL20 is known to be up-regulated in synovium explants or fibroblast-like synoviocytes from RA patients after stimulation of TNF-$\alpha$, IL-1b and IL-17 (Matsui T, Clin Exp Immunol. 2001 July; 125(1):155-61. doi: 10.1046/j.1365-2249.2001.01542.x; J Immunol. 2001 Nov. 15; 167 (10):6015-20. doi: 10.4049/jimmunol.167.10.6015; Chevrel G, Ann Rheum Dis. 2002 August; 61(8):730-3. doi: 10.1136/ard.61.8.730). CCR6+ B cells in RA synovium have been reported, contributing to pathogenesis by antigen presentation, autoantibody production and/or inflammatory cytokine production. Furthermore, Rituximab is an efficacious therapy for RA (Cohen S B, Arthritis Rheum. 2006 September; 54(9):2793-806. doi: 10.1002/art.22025), supporting a role for CCR6+ B cells in RA pathogenesis. Additionally, CCR6-deficient mice have impaired IgG1-dependent memory B cell responses (J Immunol. 2015 Jan. 15; 194 (2):505-13. doi: 10.4049/jimmunol.1401553). Preclinical rodent models showed that CCR6-deficient mice developed a less severe joint inflammation in the collagen-induced arthritis (CIA) model. Reduced production of collagen-specific antibodies in CCR6-deficient mice were observed compared to WT mice, and arthritic inflammation was also reduced (J Cell Mol Med. 2018 November; 22(11):5278-5285. doi: 10.1111/jcmm.13783). Furthermore, depletion of CCR6+ cells reduced the severity of SKG arthritis (Hirota K, J Exp Med. 2007 Nov. 26; 204(12):2803-12. doi: 10.1084/jem.20071397).

CCR6+ Th17 are increased in peripheral blood in ankylosing spondylitis patients (Shen H, Arthritis Rheum. 2009 June; 60(6):1647-56. doi: 10.1002/art.24568). Circulating interleukin-17-secreting interleukin-23 receptor-positive $\gamma/\delta$ T cells were also reported in patients with active ankylosing spondylitis (Kenna T J, Arthritis Rheum. 2012 May; 64(5): 1420-9. doi: 10.1002/art.33507). Secukinumab, an IL-17A inhibitor, in was shown to be efficacious in ankylosing spondylitis (AS) (Baeten D, N Engl J Med. 2015 Dec. 24; 373(26):2534-48. doi: 10.1056/NEJMoa1505066). CD32B expression on memory B cells in AS was increased and was associated with disease activity. Furthermore, $CCR6^+$ cytotoxic T-cells and $CD32B^+$ memory B-cells were highly enriched within the synovial compartment of AS patients (Sucur A, Clin Exp Rheumatol. 2019 Nov. 20; PMID: 31820725).

Psoriasis is a commonly occurring autoimmune skin disease. The role of Th17-associated cytokines has been clinically validated and their role in psoriatic inflammation confirmed (Paul C, J Eur Acad Dermatol Venereol. 2015 June; 29(6):1082-90. doi: 10.1111/jdv.12751). An IL-17R-blocking antibody (brodalumab, AMG 827) were shown to reduce clinical manifestations of psoriasis and also to reduce CCL20 expression in skin biopsies from psoriasis patients (Papp K A, N Engl J Med. 2012 Mar. 29; 366(13):1181-9. doi: 10.1056/NEJMoa1109017). Also, an IL-23 neutralizing antibody (guselkumab) was shown to be efficacious in reducing psoriatic inflammation (Reich K, Lancet. 2019 Sep. 7; 394(10201):831-839. doi: 10.1016/S0140-6736(19) 31773-8). CCR6-deficient mice failed to develop psoriasiform skin lesions following intradermal IL-23 injections (Hedrick M N, J Clin Invest. 2009 August; 119(8):2317-29. doi: 10.1172/jci37378). Small molecule CCR6 antagonists have also been shown to be efficacious in the Aldara and IL-36a-injection mouse psoriasis models (Campbell J J, J Immunol. 2019 Mar. 15; 202(6):1687-1692. doi: 10.4049/jimmunol.1801519; Campbell J J, J Immunol. 2017 Nov. 1; 199(9):3129-3136. doi: 10.4049/jimmunol.1700826). Furthermore, CCR6-deficient mice have been shown to be protected from imiquimod-induced ear swelling (Yu S, J Invest Dermatol. 2019 February; 139(2): 485-488. doi: 10.1016/j.jid.2018.07.036).

Anti-CCR6 neutralizing antibodies have also shown efficacy in Aldara induced ear swelling in mice (Robert R, JCI Insight. 2017 Aug. 3; 2(15): e94821. Published online 2017 Aug. 3. doi: 10.1172/jci.insight.94821). An engineered disulfide-linked CCL20 dimer, which binds CCR6 but inhibits T cell migration, was shown to reduce skin swelling in an IL-23-dependent mouse model of psoriasis (Getschman A E, Proc Natl Acad Sci USA. 2017 Nov. 21; 114(47):12460-12465. doi: 10.1073/pnas.1704958114). Collectively, these data show that a positive feedback consisting of epidermal and dermal production of CCL20, potent recruitment of CCR6+ T cells or into inflamed psoriatic skin, their activation by IL-23 and their expression of IL-17A and IL-22, drives a pathogenic Th17 response in psoriatic skin lesions. Inhibition of CCR6 has therefore been recognized as a potential therapeutic pathway to treat psoriasis (Hedrick M N, Expert Opin Ther Targets. 2010 September; 14(9):911-22. doi: 10.1517/14728222.2010.504716; Mabuchi T, J Dermatol Sci. 2012 January; 65(1):4-11. doi: 10.1016/j.jdermsci.2011.11.007). CCR6 expression was shown to be upregulated in synovial membranes of psoriatic arthritis (PsA) patients (Dolcino M, PLoS One. 2015 Jun. 18; 10(6): e0128262. doi: 10.1371/journal.pone.0128262). IL-17A- and GM-CSF-expressing CD4+ T cells isolated from synovial fluid of PsA patients also expressed CCR6 (Al-Mossawi et al., Nat Commun. 2017 Nov. 15; 8(1):1510. doi: 10.1038/s41467-017-01771-2). CCL20 was shown to be highly upregulated in synovial fluid retrieved from PsA patients (Melis L, Ann Rheum Dis. 2010 March; 69(3):618-23. doi: 10.1136/ard.2009.107649).

Additional inflammatory skin disorders including rosacea have been shown to have highly elevated levels of CCL20 in inflamed skin (Buhl T, JID, 2015).

CCR6 and CCL20 are highly elevated in active Crohn's disease (CD) and ulcerative colitis (UC) (Skovdahl et al., PLoS One. 2015 Nov. 4; 10(11):e0141710. doi: 10.1371/journal.pone.0141710). Increased enterocyte CCL20 production has been proposed to play an important role in lymphocyte recruitment to the colonic epithelium in irritable bowel disease (IBD) (Kwon J H, Gut. 2002 December; 51(6):818-26. doi: 10.1136/gut.51.6.818). CCL20 and CCR6 expression are also correlated with histological severity in rectum resected from UC patients. CCL20 expression in chronic UC is higher than that in acute UC after pathological examination (Uchida K, Gastroenterol Res Pract. 2015; 2015:856532. doi: 10.1155/2015/856532). Expression of CCL20 was significantly up-regulated in the PBMCs of patients with UC compared with those of normal healthy controls. UC groups treated with sulfasalazine and GC showed decreases of CCL20 expression in PBMCs, accompanied by ameliorated disease. TNF$\alpha$ or IL-1$\beta$-induced CCL20 secretion was strongly reduced by sulfasalazine and/or GC treatment of human intestinal epithelial cell lines (Lee H J, 2 Inflamm Bowel Dis. 2005 December; 11(12): 1070-9. doi: 10.1097/01.mib.0000187576.26043.ac). CCR6 deficiency resulted in reduced intestinal pathology in mice treated with dextran sodium sulfate (DSS) to induce colonic inflammation (Varona R, Eur J Immunol. 2003 October; 33(10):2937-46. doi: 10.1002/eji.200324347).

Th17 cells expressing CCR6 were shown to be important effectors mediating dry eye disease (DED), an inflammatory state at the ocular surface, potentially resulting in corneal perforation. Antibody-mediated neutralization of CCL20 in a DED mouse model reduced Th17 recruitment into the ocular surface, resulting in improved clinical readouts (Dohlman T H, Invest Ophthalmol Vis Sci. 2013 Jun. 12; 54(6):4081-91. doi: 10.1167/iovs.12-11216). Inhibition of the CCR6/CCL20 axis was therefore proposed as a therapeutic mechanism to treat DED.

CCR6 expression has been described on T cells isolated from the cerebrospinal fluid of multiple sclerosis (MS) patients (van Langelaar J, Brain, 2018 May 1; 141(5):1334-1349. doi: 10.1093/brain/awy069). CCR6 expression was also shown on T cells infiltrating the inflamed CNS in experimental autoimmune encephalomyelitis (EAE) (Mony J T, Front Cell Neurosci. 2014; 8:187. doi: 10.3389/fncel.2014.00187). Furthermore, CCL20 gene polymorphisms have been shown to be associated with MS patient cohorts (El Sharkav et al., Gene. 2019 Feb. 15; 685:164-169. doi: 10.1016/j.gene.2018.11.006). Preclinical data has shown that CCR6 is important for development of EAE (Reboldi A, Nat Immunol. 2009 May; 10(5):514-23. doi: 10.1038/ni.1716). This finding was confirmed in later study, showing that CCR6-deficient mice were resistant to disease induction with reduced peak severity. In the same study, vaccination with hCCL20 produced an anti-mouse CCL20 response in the host mice, which was sufficient to reduce clinical scores (Abraham M, Clin Immunol. 2017 October; 183:316-324. doi: 10.1016/j.clim.2017.09.018). However, conflicting data exists concerning the role for CCR6 in EAE development (J Neuroimmunol. 2009 Aug. 18; 213(1-2):91-9. doi: 10.1016/j.jneuroim.2009.05.011). EAE severity and histopathology were significantly reduced after injection of anti-CCL20 upon first clinical manifestations (Kohler R E, J Immunol. 2003 Jun. 15; 170(12):6298-306. doi: 10.4049/jimmunol.170.12.6298). Anti-CCR6 neutralizing antibodies were shown to reduce the severity of EAE in mice (Robert R, JCI Insight. 2017 Aug. 3; 2(15): e94821. Published online 2017 Aug. 3. doi: 10.1172/jci.insight.94821). IL-6 and IL-17 increase the expression of CCL20 from murine astrocytes (Meares G P, Glia. 2012 May; 60(5):771-81. doi: 10.1002/glia.22307).

CCR6 and CCL20 are proposed to influence kinetics of germinal center (GC) formation and B cell responses and CCR6 is considered a marker memory B cell precursors in both mouse and human germinal centers (Suan D, Immunity. 2017 Dec. 19; 47(6):1142-1153.e4. doi: 10.1016/j.immuni.2017.11.022). Expression of CCR6 on naive, pre-GC, GC/plasma cell and memory B cells in peripheral B cells of systemic lupus erythematosus (SLE) patients was increased (Lee A Y S, Clin Rheumatol. 2017 June; 36(6):1453-1456. doi: 10.1007/s10067-017-3652-3).CD4+CCR6+ cells may also contribute to disease severity in SLE patients and were shown to be increased in anti-DNA+ SLE patients, which correlated with disease severity and erythrocyte sedimentation rate (Zhong W, PeerJ. 2018; 6:e4294. doi: 10.7717/peerj.4294). Increased CCR6 expression in the salivary glands of patients with primary Sjögren's syndrome (pSS) was demonstrated [Scand J Immunol. 2020 March; 91(3): e12852. doi: 10.1111/sji.12852]. A trend towards increased CCL20 mRNA expression was also observed. Significant reductions in CCR6+Th cells (both CCR9- and CCR9+) in the circulation of patients with pSS as compared with healthy controls (HCs) were demonstrated [Scand J Immunol. 2020 March; 91(3):e12852. doi: 10.1111/sji.12852].

In an animal model of autoimmune hepatitis (AIH), administering anti-TNF-α suppressed hepatic CCL20 expression. Mice receiving anti-CCL20 showed reduced AIH. Furthermore, TNFα stimulation enhanced CCL20 expression in hepatocytes. These findings suggest that TNFα is essential in the induction of AIH through upregulation of hepatic CCL20 expression, which recruits CCR6+ T cells which drive pathology (Clin Immunol. 2013 January; 146(1):15-25. doi: 10.1016/j.clim.2012.10.008).

The present CCR6 modulators may be useful, alone, or in combination in the treatment or prevention of autoimmune diseases or disorders including Posterior uveitis, allergic conjunctivitis, allergic disease in the gastrointestinal tract, type I diabetes and endometriosis (Medicina (Kaunas). 2018 Nov. 16; 54(5). doi: 10.3390/medicina54050088). CCR6 modulators may also be useful, alone or in combination, to treat diseases of the ocular surface in which elevated levels of IL-17A have been recorded, including meibomian gland dysfunction; GVHD, graft-versus host disease; autoimmune keratitis, filamentary keratitis, dry eye syndrome with rheumatic arthritis; dry eye syndrome without systemic disease; Stevens-Johnson syndrome. (J Korean Med Sci. 2011 July; 26(7):938-44. doi: 10.3346/jkms.2011.26.7.938).

The present CCR6 modulators may be useful, alone, or in combination in the treatment or prevention of malignant diseases. Modulation of the CCR6/CCL20 axis using siRNA, shRNA, CCR6 knock-out animals, CCL20 ligand treatment or antibodies has been shown to alter tumor growth and metastatic processes in experimental disease models as single agents, or in combination with immunotherapy (such as especially PD1 and/or PDL1 blockade) for the prevention/prophylaxis or treatment of cancers.

The therapeutic potential of modulating this axis for the treatment of malignancies has been described in tumor mouse models using small interfering RNA (siRNA) or small hairpin RNA (shRNA)-mediated silencing of CCR6 or CCL20. Specifically, in a mouse model of cutaneous T cell lymphoma (My-La cells), Abe et al. reported that the administration of a CCR6-targeted siRNA prolonged survival of animals when compared with control animals (Oncotarget. 2017 Jan. 31; 8(5):7572-7585. doi: 10.18632/oncotarget.13810.). Using another approach, Ito and colleagues demonstrated that mice, injected with T lymphoma cells (My-La) harboring a CCR6 silencing siRNA construct, survived significantly longer than mice injected with control cells (Blood. 2014 Mar. 6; 123(10):1499-511. doi: 10.1182/blood-2013-09-527739.). Zhu and co-workers demonstrated that, the average volume and weight of tumor nodules in mice injected subcutaneously with a set of colorectal cancer cell lines was decreased when CCR6 was silenced in the cancer cells by means of shRNA (PMID Biochim Biophys Acta Mol Basis Dis. 2018 February; 1864(2):387-397. doi: 10.1016/j.bbadis.2017.10.033.). In glioblastoma xenograft models using patient-derived glioblastoma cell lines, mice injected with cells harboring a shRNA construct silencing CCR6 expression survived longer than those injected with control cells. In addition, histology and immunohistochemistry revealed that tumors formed by glioma cells with CCR6-targeting shRNA were much smaller, and tumor vessel formation was significantly lower versus control tumors. Collectively, these data further support the notion that CCR6 signaling enhances the oncogenic potential of malignancies including lymphoma, colorectal tumors and glioblastoma (Oncogene. 2018 June; 37(23):3070-3087. doi: 10.1038/s41388-018-0182-7.). Specifically, the implication of the CCR6/CCL20 axis in tumorigenesis using CCR6 knock-out animals was reported in the literature. In the CMT93 mouse model of colorectal cancer (CRC), the infiltration of T regulatory cells was completely prevented in tumors of mice deficient in CCR6 in comparison to wildtype animals. The reported data further suggest that the homing and trafficking of tumor-infiltrating T regulatory cells to the tumor mass is dependent on the chemokine receptor CCR6 in vivo (PLoS One. 2011 Apr. 29; 6(4):e19495. doi: 10.1371/journal.pone.0019495.). According to Nandi and colleagues, in a mouse model of spontaneous intestinal tumorigenesis [APCMIN/+ mice, heterozygous for a mutation in the adenomatous polyposis coli (APC) gene], mice deficient in CCR6 had a lower occurrence of spontaneous intestinal tumorigenesis (PLoS One. 2014; 9(5):e97566. doi: 10.1371/journal.pone.0097566.).

The potential role of the CCR6/CCL20 axis in tumorigenesis was also demonstrated by administrating the recombinant CCL20 chemokine. Specifically, in a mouse model of colorectal cancer (CMT93 cells), Liu and colleagues showed that tumor size was significantly increased in mice treated with recombinant mouse CCL20 compared with PBS controls, suggesting a critical role for CCL20 in colorectal cancer growth and development (PLoS One. 2011 Apr. 29; 6(4):e19495. doi: 10.1371/journal.pone.0019495.).

Specifically, using neutralizing CCL20 antibodies, the potential role of the CCR6/CCL20 axis in tumor promotion was demonstrated in the literature using mouse models. Ikeda and co-workers used a specific cutaneous T cell lymphoma (CTCL) mouse model in which animals succumb to metastasis of CTCL cells into multiple organs. However, administration of a neutralizing CCL20 antibody significantly prolonged the survival of the xenografted mice (Oncotarget. 2016 Mar. 22; 7(12):13563-74. doi: 10.18632/oncotarget.6916.). Lee and co-workers described in a mouse model of metastatic breast cancer (MDA-MB-231 cells were injected into the left cardiac ventricles of nude mice) that the administration of an anti-CCL20 antibody prevented the development of bone metastasis, one of the major site of breast cancer metastasis in human disease (Sci Rep. 2017 Aug. 29; 7(1):9610. doi: 10.1038/s41598-017-09040-4.). In a humanized mouse model of nasopharyngeal carcinoma, Mrizak et al. observed a significant decrease of T regulatory cell recruitment into the tumor when mice were injected with anti-CCL20 monoclinal antibody in comparison to sham treated animals (J Natl Cancer Inst. 2015 January; 107(1):363. doi: 10.1093/jnci/dju363.). In addition, in a mouse model of hepatocarcinoma (Hepa1-6 cells), blockade of CCL20 activity in immunocompetent mice using an anti-CCL20 antibody, attenuated tumor incidence, restrained tumor growth and distal metastasis. Moreover, the authors reported that in this mouse model, tumor angiogenesis was significantly inhibited upon CCL20 neutralization. (He at al., PMID 28560063—Am J Cancer Res. 2017; 7(5):1151-1163.). Using the same mouse model, the administration of the anti-CCL20 neutralizing antibody remarkably reduced the infiltration of T regulatory cells into the tumor, especially CCR6 positive T regulatory cells, and significantly decreased tumor growth. Antitumor efficacy was further enhanced when the mice were co-treated with an anti-PDL-1 antibody. Collectively these data sets suggest that CCL20 blockade could abrogate anti-PD-L1 resistance in a mouse model of hepatocarcinoma by inhibiting T regulatory recruitment to the tumor (Hepatology. 2019 July; 70(1):198-214. doi: 10.1002/hep.30593.).

Specifically, the potential role of the CCR6/CCL20 axis in tumor metastasis was described in the literature. Dellacasagrande and colleagues reported that, in a mouse model of plasmacytoma, tumor cells that disseminated to the liver overexpressed functional CCR6 in comparison with tumor cells of the primary tumor (from s.c. injection of mouse plasmacytoma (MOPC315)). The same authors found that CCR6 was overexpressed in small liver metastases of colon, thyroid and ovarian carcinomas compared with normal liver (Scand J Immunol. 2003 June; 57(6):534-44. doi: 10.1046/j.1365-3083.2003.01263.x.).

Furthermore, the present CCR6 modulators may be useful, alone, or in combination in the treatment or prevention of cancers where the expression of CCR6 and/or CCL20 correlates with disease progression and resistance to standard treatment care. Specifically, the correlation of CCR6 expression with disease progression was described in the literature for numerous cancer indications. For example, in renal cell carcinoma CCR6 expression is associated with a lower overall survival (Cancers (Basel). 2019 Dec. 30; 12(1). doi: 10.3390/cancers12010089.). In colorectal cancer, tumor expression of CCR6 positively correlates with metastasis and upregulated CCR6 predicts poor survival, shorter disease-free survival (PLoS One. 2014; 9(6):e101137. doi: 10.1371/journal.pone.0101137.), and poorer 5-year overall survival (Biochim Biophys Acta Mol Basis Dis. 2018 February; 1864(2):387-397. doi: 10.1016/j.bbadis.2017.10.033.). In ovarian cancer high CCR6 mRNA expression was also associated with a worse prognosis (Cancer Lett. 2020 Mar. 1; 472:59-69. doi: 10.1016/j.canlet.2019.12.024.). CCR6 expression was associated with rectal cancer aggressiveness, indeed, high-level expression of CCR6 protein was more common in non-responders to radiotherapy than in responders (Cancer Res Treat. 2018 October; 50(4):1203-1213. doi: 10.4143/crt.2017.538.). The expression level of CCR6 in prostate cancer was associated with clinical and pathologic features of more advanced and aggressive disease (J Cancer Res Clin Oncol. 2008 November; 134(11):1181-9. doi: 10.1007/s00432-008-0403-5.). In non-small cell lung cancer (NSCLC) high CCR6 expression was associated with shorter disease-free survival and conferred a disease stage-independent 5-fold increased risk for disease recurrence (PLoS One. 2011; 6(9):e24856. doi: 10.1371/journal.pone.0024856.). Hepatocarcinoma patients with increased infiltrated CCR6 positive immune cells in tumor tissues showed a poorer prognosis (Am J Cancer Res. 2017; 7(5):1151-1163.).

Analogous to CCR6, expression of its ligand CCL20 has been reported to correlate with poorer disease outcome for several indications. Specifically, in breast cancer, elevated CCL20 expression significantly correlated with lower overall free survival, lower percent metastasis free survival (Sci Rep. 2017 Aug. 29; 7(1):9610. doi: 10.1038/s41598-017-09040-4.), with higher histological grade, higher Ki67 index, and axillary lymph node metastases. Moreover, breast tumor CCL20 expression positively correlated with expression of FOXP3, a marker of T regulatory cells. Patients with axillary lymph node metastases, and concomitant elevation in CCL20 expression and FOXP3-positive T regulatory cells, had the worst overall survival. (Medicine (Baltimore). 2019 December; 98(50):e18403. doi: 10.1097/MD.0000000000018403.). In NSCLC higher expression of CCL20 was associated with a lower overall survival (Biomed Pharmacother. 2015 February; 69:242-8. doi: 10.1016/j.biopha.2014.12.008.)(Cancer Lett. 2015 Jul. 10; 363(1):60-70. doi: 10.1016/j.canlet.2015.04.005.). Analogous to NSCLC, hepatocellular carcinoma patients with high CCL20 expression had poorer overall survival and poorer recurrence-free survival. The same authors described that CCL20 expression was significantly associated with tumor size, tumor number, vascular invasion, tumor differentiation and tumor recurrence (J Gastrointest Surg. 2012 April; 16(4):828-36. doi: 10.1007/s11605-011-1775-4.). In addition to CCR6 or CCL20 alone, correlation of CCR6/CCL20 co-expression with disease progression is stated in literature. Indeed, overexpression of both, CCL20 and CCR6, was detected in high-grade glioma tissues as compared to low-grade tissues and increased with ascending tumor World Health Organization (WHO) grades. Particularly glioma patients with CCL20/CCR6 co-expression had the shortest overall survival (Med Oncol. 2012 December; 29(5):3491-7. doi: 10.1007/s12032-012-0314-9.).

Besides, CCR6 and/or CCL20 expression correlates with enhance chemotherapeutic resistance and is associated with metastasis. Indeed, CCL20 expression can increase the chemotherapeutic resistance of breast cancer cells (PLoS Biol. 2018 July; 16(7):e2005869. doi: 10.1371/journal.pbio.2005869.). Rubie and colleagues describe that in colorectal liver metastases (CRLM) and in human samples of hepatocellular carcinoma (HCC), significant up-regulation of CCL20/CCR6 was detected (RT-PCR). Moreover, CCL20 was significantly overexpression in colorectal liver metastases as compared to the primary HCC, indicating an involvement of the CCL20/CCR6 ligand-receptor pair in the carcinogenesis and progression of hepatic malignancies (World J Gastroenterol. 2006 Nov. 7; 12(41):6627-33. doi: 10.3748/wjg.v12.i41.6627.).

The present CCR6 modulators may be useful, alone, or in combination in the treatment or prevention of diseases or disorders where CCR6 and/or CCL20 are expressed or overexpressed in patient samples or cancer cell lines. Specifically, the chemokine receptor CCR6 is described to be expressed in several cancer types or cancer cell lines in the literature. Lu and coworkers describe that CCR6 expression was higher in laryngeal cancer tissues compared with their normal controls. The authors reported that CCR6 was also expressed in commonly used laryngeal cancer cells such as TU212, M4E, M2E and Hep-2 (Biomed Pharmacother. 2017 January; 85:486-492 doi: 10.1016/j.biopha.2016.11.055.). Based on gene expression data from malignant melanoma, among the biological networks reported CCR6 gene was described and characterized as a valuable factor involved in immune responses and tumor progression (PLoS One. 2018; 13(1):e0190447. doi: 10.1371/journal.pone.0190447.) Whole exome sequencing in 21 MALT lymphomas of the salivary gland and thyroid revealed that CCR6 was expressed (Haematologica. 2018 August; 103(8):1329-1336. doi: 10.3324/haematol.2018.191601.). In samples of adult human T-cell leukemia/lymphoma (ATLL) transcripts of CCR6 were detected, and CCR6 was further found at the protein level using flow cytometric analysis (Leuk Lymphoma. 2006 October; 47(10):2163-73. doi: 10.1080/10428190600775599.). In patient-derived prostate cancer samples the gene expression of CCR6 (mRNA) was significantly higher in tumor tissue as compared to adjacent normal tissue (Cancer Res Treat. 2015 April; 47(2):306-12. doi: 10.4143/crt.2014.015.). CCR6 expression was detected in commonly used cancer cell lines, indeed, according to Mays and co-workers, in salivary adenoid cystic carcinoma cells SACC-83, among other CC chemokine receptors, CCR6 was expressed using RT-PCR gene analysis (Anticancer Res. 2016 August; 36(8):4013-8.). According to Möller and colleagues, in multiple myeloma (MM) cell lines including U266 1970, U-266 1984, U-1958, Karpas 707, LP-1,28 L-363, HL407E and HL407L.3, CCR6 was also expressed (Leukemia. 2003 January; 17(1):203-10. doi: 10.1038/sj.leu.2402717.).

Analogous to CCR6, the ligand CCL20 was reported to be expressed in multiple tumor samples and tumor cell lines in the literature. For example, Zhang and co-workers demonstrated that in samples from NSCLC patients, using RT-PCR, CCL20 showed higher expression in tumor samples than in samples of adjacent tissue, this was also verified at the protein level using immunohistochemistry (Biomed Pharmacother. 2015 February; 69:242-8. doi: 10.1016/j.biopha.2014.12.008.). Gene expression analysis of cholangiocarcinoma samples and corresponding normal tissue revealed CCL20 to be one of the genes most significantly over-expressed in malignant vs healthy tissue (EXCLI J. 2020; 19:154-166. doi: 10.17179/excli2019-1893.). CCL20 expression was also reported in multiple myeloma (MM) human samples (Cancer Res. 2008 Aug. 15; 68(16):6840-50. doi: 10.1158/0008-5472.CAN-08-0402.). Besides, according to Rubies et al., CCL20 mRNA and protein was significantly up-regulated in pancreatic carcinoma (8-fold) as compared to matched normal pancreas in which CCL20 was weakly expressed (J Transl Med. 2010 May 10; 8:45. doi: 10.1186/1479-5876-8-45.) . . . ). CCL20 is also expressed in oral squamous cell carcinoma (IHC staining) and Lee et al. reported that expression is enriched in human CCR6+ regulatory T cells with superior suppressive activity (J Immunol. 2017 Jul. 15; 199(2):467-476. doi: 10.4049/jimmunol.1601815.).

In addition to CCR6 or CCL20 alone, the co-expression of both CCR6 and CCL20 is reported for samples of cancer patients and cancer cells lines in literature. Both genes have been described to be expressed in adult T-cell leukemia/lymphoma patient samples (Microarray and IHC protein staining) (Int J Oncol. 2014 September; 45(3):1200-8. doi: 10.3892/ijo.2014.2524.) and in CTCL. In the latter, CCL20 and CCR6 were detected at the mRNA and protein levels (Clin Cancer Res. 2011 Dec. 15; 17(24):7529-38. doi: 10.1158/1078-0432.CCR-11-1192.). Transcriptomic analysis (nanostring) of samples of hepatocellular carcinoma revealed CCR6 and CCL20 expression. Moreover, a chemotactic gradient between non-tumor and tumor tissues was reported and a recruitment process of T regulatory cells, tumor associated macrophages and natural killer cells involving the CCR6/CCL20 axis suggested (Proc Natl Acad Sci USA. 2017 Jul. 18; 114(29):E5900-E5909. doi: 10.1073/pnas.1706559114.). Similarly, Guo and co-workers reported CCR6 and CCL20 upregulation in hepatocarcinoma lesions compared to healthy tissue as well as CCR6 and CCL20 expression in hepatocarcinoma cell lines (L02, Li-/, Huh-7, SNU-387, Hep3B) (Oncol Rep. 2019 September; 42(3):1075-1089. doi: 10.3892/or.2019.7221.). In human colorectal cancer, both CCL20 and CCR6 are expressed according to Nandi et al. (IHC protein staining). Both, CCR6 and CCL20, were found to be highly expressed in samples of NSCLC (protein and mRNA) (Oncol Lett. 2017 December; 14(6):8183-8189. doi: 10.3892/ol.2017.7253). Using in situ hybridization, both CCL20 and CCR6 mRNA moieties were strongly expressed in all pancreatic cancer samples analysed. In contrast, in healthy pancreas CCL20 and CCR6 expression was low (Int J Cancer. 1999 May 17; 81(4):650-7. doi: 10.1002/(sici)1097-0215(19990517)81:4<650::aid-ijc23>3.0.co;2-#.). Jin and co-workers examined CCR6 and CCL20 expression in glioblastoma using publicly available datasets. The authors used the GEO dataset GSE2223 to compare the mRNA levels of CCL20 and CCR6, between normal brain and glioblastoma tissues. Again, CCR6 and CCL20 expression levels were significantly higher in glioblastoma tissues than in normal brain tissues (Oncogene. 2018 June; 37(23):3070-3087. doi: 10.1038/s41388-018-

0182-7.). In addition, Wallace and colleagues observed that in endometrial adenocarcinoma explants and cell lines, expression of CCL20 and its receptor CCR6 were higher compared to non-malignant endometrium (mRNA, RT-PCR) (Mol Cell Endocrinol. 2011 Jan. 1; 331(1):129-35. doi: 10.1016/j.mce.2010.08.018.). CCL20/CCR6 axis may play a role in breast cancer, cholangiocarcinoma, and thyroid cancer since expression of CCR6/CCL20 genes and/or proteins was reported in patient derived breast cancer cells (Mol Carcinog. 2016 July; 55(7):1175-86. doi: 10.1002/mc.22360.), in HuCCT1 and TFK-1 cholangiocarcinoma cell lines ( ) (Win et al., PMID 32194362) (EXCLI J. 2020; 19:154-166. doi: 10.17179/excli2019-1893.) and thyroid cancer cell lines such as TPC-1, BCPAP, FTC-133, and SW1736 (Tumour Biol. 2016 April; 37(4):5569-75. doi: 10.1007/s13277-015-4418-7.). Furthermore, the present CCR6 modulators may be useful, alone, or in combination in the treatment or prevention of cancers where the expression and/or evidence of CCR6/CCL20 axis activity has been reported, or where CCR6+ regulatory T cells have been identified inside the tumor microenvironment.

1) One aspect of the present invention relates to compounds of Formula (I)

Formula (I)

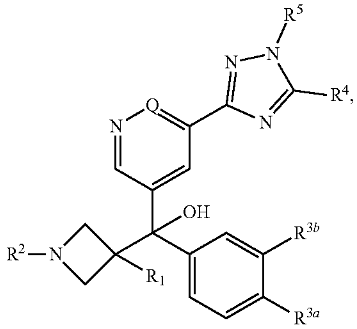

wherein

Q represents N, CH, or C—R, wherein R represents halogen or $C_{1-3}$-alkyl;

$R^1$ represents
- $C_{1-3}$-alkyl (especially methyl);

$R^2$ represents
- hydrogen;
- $C_{1-4}$-alkyl (especially methyl or isopropyl);
- hydroxy-$C_{1-3}$-alkyl (especially 2-hydroxyethyl);
- $C_{1-3}$-fluoroalkyl (notably $C_1$-fluoroalkyl; especially 2,2-difluoroethyl); or
- $C_{3-5}$-cycloalkyl;

$R^{3a}$ represents
- halogen (especially bromine);
- $C_{1-5}$-alkyl (especially ethyl, n-propyl, isopropyl, tert-butyl; in particular isopropyl);
- $C_{1-3}$-fluoroalkyl (especially 2,2,2-trifluoro-ethyl);
- $C_{1-3}$-fluoroalkoxy (notably $C_1$-fluoroalkoxy; especially trifluoromethoxy);
- $C_{3-5}$-cycloalkyl (especially cyclopropyl); or
- 1-($C_{1-3}$-fluoroalkyl)-$C_{3-5}$-cycloalkyl (notably 1-($C_1$-fluoroalkyl)-$C_{3-5}$-cycloalkyl; especially 1-trifluoromethyl-cyclopropyl);

$R^{3b}$ represents
- hydrogen; or
- halogen;

$R^4$ represents
- $C_{1-4}$-alkyl which is unsubstituted; mono-substituted, wherein the substituent is selected from hydroxy or $C_{1-3}$-alkyl-amino (especially methyl-amino); or di-substituted, wherein the first substituent represents hydroxy, and the second substituent represents $C_1$-fluoroalkyl (especially trifluoromethyl)
- [in particular such $C_{1-4}$-alkyl represents 1-hydroxy-1-methyl-ethyl, 1-methyl-1-(methyl-amino)-ethyl, or 1-hydroxy-1-trifluoromethyl-ethyl]; or
- -L-Cy, wherein
  - -L- represents a direct bond (i.e. Cy is directly attached to the triazolyl ring) or —$CH_2$— (especially a direct bond); and
  - Cy represents $C_{3-7}$-cycloalkyl optionally containing one ring heteroatom selected from nitrogen or oxygen (notably such Cy represents cyclobutyl, cyclohexyl, tetrahydropyranyl, or piperidinyl; especially cyclobutyl, cyclohexyl, tetrahydropyran-4-yl, or piperidin-4-yl), wherein Cy independently is unsubstituted; or
    - mono-substituted with
      - hydroxy;
      - oxo;
      - $C_{1-4}$-alkyl;
      - -C(=O)$R^A$, wherein $R^A$ represents $C_{1-3}$-alkyl (especially methyl) or hydroxy-$C_{1-3}$-alkyl; or
      - $C_{1-3}$-alkyl-carbonyl-amino; or
    - di-substituted, wherein the first substituent represents oxo, and the second substituent represents $C_{1-3}$-alkyl; or di-substituted, wherein the first substituent represents hydroxy and the second substituent represents $C_{1-3}$-alkyl-carbonyl;
  - or Cy represents a saturated 5- to 8-membered bridged bicyclic hydrocarbon ring system (especially such ring system represents bicyclo[1.1.1]pentan-1-yl or bicyclo[2.2.2]octan-1-yl), wherein Cy independently is mono-substituted (notably at the tertiary carbon atom of said ring system), wherein the substituent is selected from
    - hydroxy-$C_{1-3}$-alkyl (especially hydroxy-methyl); or
    - —C(=O)$R^B$, wherein $R^B$ represents
      - hydroxy;
      - —$NR^{N1}R^{N2}$, wherein $R^{N1}$ and $R^{N2}$ independently represent hydrogen or $C_{1-3}$-alkyl; or $R^{N1}$ and $R^{N2}$ together with the nitrogen atom to which they are attached form pyrrolidinyl; or
      - $C_{1-3}$-alkoxy (especially methoxy);
  - or Cy represents a 5- or 6-membered heteroaryl (notably 6-membered heteroaryl) containing one or two ring heteroatoms (notably one) independently selected from nitrogen or oxygen (notably nitrogen) (especially Cy represents pyridinyl; in particular pyridin-3-yl)
- [in particular such -L-Cy group represents tetrahydropyran-4-yl, 4-hydroxy-tetrahydropyran-4-yl, 1-hydroxy-cyclobutyl-methyl, 4-hydroxy-cyclohexyl, pyridin-3-yl, 4-methoxycarbonyl-bicyclo[2.2.2]octan-1-yl, 4-carboxy-bicyclo[2.2.2]octan-1-yl, 3-hydroxymethyl-bicyclo[1.1.1]pentan-1-yl, or N-acetyl-piperidin-4-yl]; and $R^5$ represents
- $C_{1-4}$-alkyl (especially methyl, ethyl, isopropyl, or tert-butyl);
- hydroxy-$C_{1-3}$-alkyl (especially 2-hydroxyethyl);
- $C_{1-3}$-alkoxy-$C_{1-3}$-alkyl;

$C_{3-7}$-cycloalkyl (especially cyclopropyl, cyclobutyl, cyclopentyl, or cyclohexyl);
$C_{1-3}$-fluoroalkyl (especially 2,2-difluoropropyl);
$C_{1-3}$-alkyl-carbonyl; or
$C_{1-3}$-alkyl-carbonyl-amino-$C_{1-3}$-alkyl;

or $R^4$ and $R^5$ together with the triazolyl ring to which they are attached form 5,6,7,8-tetrahydro-[1,2,4]triazolo[1,5-a]pyridin-2-yl or 6,7-dihydro-5H-pyrrolo[1,2-b][1,2,4]triazol-2-yl.

Definitions provided herein are intended to apply uniformly to the compounds of Formula (I) as defined in any one of embodiments 1) to 13), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. If not explicitly defined otherwise in the respective embodiment or claim, groups defined herein are unsubstituted.

The term "halogen", used alone or in combination, means fluorine, chlorine, bromine, or iodine; notably fluorine, chlorine, or bromine. For $R^{3b}$ preferred example is fluorine.

The term "oxy", used alone or in combination, refers to the group —O—.

The term "oxo", used alone or in combination, refers to the group =O.

The term "amino", used alone or in combination, refers to the group $—NH_2$.

The term "alkyl", used alone or in combination, refers to a saturated straight or branched hydrocarbon chain group containing one to six carbon atoms. The term "$C_{x-y}$-alkyl" (x and y each being an integer), refers to an alkyl group as defined before, containing x to y carbon atoms. In case a $C_{x-y}$-alkyl group is used in combination with another substituent, the term means that said substituent is linked through a $C_{x-y}$-alkyl group to the rest of the molecule. For example, a $C_{1-6}$-alkyl group contains from one to six carbon atoms. Examples of $C_{1-4}$-alkyl groups are methyl, ethyl, n-propyl, isopropyl, n-butyl, sec-butyl, tert-butyl, and isobutyl.

The term "hydroxyalkyl" (or hydroxy-alkyl), used alone or in combination, refers to an alkyl group as defined before, wherein one hydrogen atom has been replaced by a hydroxy group. The term "hydroxy-$C_{x-y}$-alkyl" (x and y each being an integer), used alone or in combination, refers to a hydroxyalkyl group as defined before wherein the alkyl group contains x to y carbon atoms. For example, a hydroxy-$C_{1-3}$-alkyl group is a hydroxyalkyl group as defined before which contains from one to three carbon atoms. Examples of hydroxy-$C_{1-3}$-alkyl groups are hydroxymethyl, 1-hydroxyethyl, 2-hydroxyethyl, 1-hydroxypropyl, 2-hydroxypropyl, 3-hydroxypropyl, 1-hydroxy-1-methyl-ethyl, and 1-methyl-2-hydroxyethyl.

The term "fluoroalkyl", used alone or in combination, refers to an alkyl group as defined before in which one or more (and possibly all) hydrogen atoms have been replaced by fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine. Examples of $C_{1-3}$-fluoroalkyl groups are trifluoromethyl, 2-fluoroethyl, 2,2-difluoroethyl, and 2,2,2-trifluoroethyl. A preferred example of $C_{1-3}$-fluoroalkyl group is a $C_1$-fluoroalkyl group containing one carbon atom in which one to three hydrogen atoms have been replaced with fluorine. Examples of such $C_1$-fluoroalkyl group are mono-, di-, and trifluoromethyl; especially trifluoromethyl.

The term "cycloalkyl", used alone or in combination, refers to a saturated monocyclic hydrocarbon ring containing three to seven carbon atoms (preferably three to six carbon atoms). The term "$C_{x-y}$-cycloalkyl" (x and y each being an integer), refers to a saturated monocyclic hydrocarbon ring containing x to y carbon atoms. For example, a $C_{3-6}$-cycloalkyl group contains from three to six carbon atoms. Examples of $C_{3-5}$-cycloalkyl groups are cyclopropyl, cyclobutyl, and cyclopentyl.

Examples of $C_{3-7}$-cycloalkyl are cyclopropyl, cyclobutyl, cyclopentyl, cyclohexyl, and cycloheptyl. The above-mentioned cycloalkyl groups are unsubstituted or substituted as explicitly defined.

The term "$C_{3-7}$-cycloalkyl optionally containing one ring heteroatom", used alone or in combination, refers to a $C_{3-7}$-cycloalkyl group as defined before, wherein one carbon ring atom is replaced with a heteroatom selected from oxygen, nitrogen or sulfur (especially oxygen or nitrogen), or replaced as explicitly defined. Examples of $C_{3-7}$-cycloalkyl optionally containing one ring heteroatom selected from nitrogen or oxygen are cyclopropyl, cyclobutyl, cyclopentyl, cyclohexyl, cycloheptyl, aziridinyl, oxiranyl, azetidinyl, oxetanyl, pyrrolidinyl, tetrahydrofuranyl, piperidinyl, and tetrahydropyranyl; notably pyrrolidinyl, tetrahydrofuranyl, tetrahydropyranyl, and piperidinyl; especially tetrahydropyranyl and piperidinyl. The above-mentioned groups are unsubstituted or substituted as explicitly defined.

The term "$C_{1-3}$-fluoroalkyl-$C_{3-5}$-cycloalkyl", used alone or in combination, refers to a $C_{3-5}$-cycloalkyl group as defined before, wherein one hydrogen atom is replaced by $C_{1-3}$-fluoroalkyl (especially $C_1$-fluoroalkyl) as defined before. Notably, said $C_{1-3}$-fluoroalkyl is attached at the point of attachment of said $C_{3-5}$-cycloalkyl to the rest of the molecule. Examples of such groups are 1-trifluoromethyl-cyclopropyl, 1-trifluoromethyl-cyclobutyl, and 1-trifluoromethyl-cyclopentyl.

The term "alkyl-carbonyl", used alone or in combination, refers to an alkyl group as defined herein, wherein one hydrogen atom has been replaced by the group —C(=O)—. The term "$C_{x-y}$-alkyl-carbonyl" (x and y each being an integer), used alone or in combination, refers to an alkyl-carbonyl group as defined before, wherein the alkyl group contains x to y carbon atoms. For example, a $C_{1-3}$-alkyl-carbonyl group is an alkyl-carbonyl group as defined before which contains from one to three carbon atoms. Examples of such groups are acetyl, ethyl-carbonyl, propyl-carbonyl, and isopropyl-carbonyl.

The term "alkyl-carbonyl-amino", used alone or in combination, refers to an amino group as defined before, wherein one hydrogen atom has been replaced by alkyl-carbonyl group as defined before. The term "$C_{x-y}$-alkyl-carbonyl-amino" (x and y each being an integer), used alone or in combination, refers to $C_{x-y}$-alkyl-carbonyl-amino group as defined before, wherein the alkyl group contains x to y carbon atoms. A $C_{1-3}$-alkyl-carbonyl-amino group is an alkyl-carbonyl group as defined before which contains from one to three carbon atoms. Examples of such $C_{1-3}$-alkyl-carbonyl-amino groups are acetyl-amino, ethyl-carbonyl-amino, propyl-carbonyl-amino, isopropyl-carbonyl-amino; especially acetyl. The term "alkoxy", used alone or in combination, refers to an alkyl group as defined before, wherein one hydrogen atom is replaced with —O—, i.e. to the group alkyl-O—. The term "$C_{x-y}$-alkoxy" (x and y each being an integer), used alone or in combination, refers to an alkoxy group as defined before, wherein the alkoxy group contains x to y carbon atoms. For example, a $C_{1-3}$-alkoxy group is an alkoxy group as defined herein which contains from one to three carbon atoms. Examples of $C_{1-3}$-alkoxy groups are methoxy, ethoxy, n-propoxy, or isopropoxy; notably methoxy.

The term "fluoroalkoxy", used alone or in combination, refers to an alkoxy group as defined before, wherein one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced by fluorine. Examples of $C_{1-3}$-fluoroalkoxy groups are trifluoromethoxy, difluoromethoxy, 2-fluoroethoxy, 2,2-difluoroethoxy, and 2,2,2-trifluoroethoxy.

The term "5- or 6-membered heteroaryl", used alone or in combination, refers to a 5- or 6-membered monocyclic aromatic ring containing one to four ring heteroatoms (preferably one to three ring heteroatoms), each independently selected from oxygen, nitrogen, and sulfur. Examples of 5-membered groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, and tetrazolyl. Examples of 6-membered heteroaryl groups are pyridinyl, pyrimidinyl, pyridazinyl, or pyrazinyl. Preferred examples for such 5- or 6-membered heteroaryl groups are pyrrolyl, pyrazolyl, imidazolyl, oxazolyl, isoxazolyl, pyridinyl, pyrimidinyl, pyridazinyl, or pyrazinyl. The above-mentioned heteroaryl groups are unsubstituted or substituted as explicitly defined.

The term "saturated 5- to 8-membered bridged bicyclic hydrocarbon ring system", used alone or in combination, refers to two hydrocarbon rings which have two carbon atoms in common, wherein the total number of carbon atoms in both rings is an integer from 5 to 8. More particularly, said term refers to compounds described by the term "bicyclo [x.y.z]alkyl, wherein the total number of carbon atoms is an integer from 5 to 8, and each one of "x", "y" and "z" is larger than 0 [i.e. the sum of "x", "y" and "z" is from 3 to 6; and the integers "x", "y" and "z" independently indicate the number of carbon atoms in each of the three bridges linked to the two tertiary carbon atoms in descending order (x>y>z)]. Examples for such 5- to 8-membered bridged bicyclic hydrocarbon ring system are bicyclo[1.1.1]pentanyl, bicyclo[2.1.1]hexanyl bicyclo[3.1.1]heptanyl, bicyclo [2.2.1]heptanyl, and bicyclo[2.2.2]octanyl. The above-mentioned ring system are unsubstituted or substituted as explicitly defined.

In this patent application, a bond drawn as a dotted line shows the point of attachment of the radical drawn to the rest of the molecule. For example, the radical drawn below

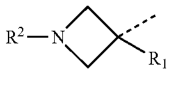

represents 1-$R^2$-3-$R^1$-azetidine-3-yl.

Further embodiments of the invention are presented hereinafter:

2) One embodiment relates to compounds according to embodiment 1), wherein

Q represents CH;

$R^1$ represents $C_{1-3}$-alkyl (especially methyl);

$R^2$ represents hydrogen;

$C_{1-4}$-alkyl (especially methyl or isopropyl);

hydroxy-$C_{1-3}$-alkyl (especially 2-hydroxyethyl); or $C_{1-3}$-fluoroalkyl (notably $C_1$-fluoroalkyl; especially 2,2-difluoroethyl);

$R^{3a}$ represents halogen (especially bromine);

$C_{1-5}$-alkyl (especially ethyl, n-propyl, isopropyl, tert-butyl; in particular isopropyl);

$C_{1-3}$-fluoroalkyl (especially 2,2,2-trifluoro-ethyl);

$C_{1-3}$-fluoroalkoxy (notably $C_1$-fluoroalkoxy; especially trifluoromethoxy);

$C_{3-5}$-cycloalkyl (especially cyclopropyl); or 1-($C_{1-3}$-fluoroalkyl)-$C_{3-5}$-cycloalkyl (notably 1-($C_1$-fluoroalkyl)-$C_{3-5}$-cycloalkyl; especially 1-trifluoromethyl-cyclopropyl);

$R^{3b}$ represents hydrogen;

$R^4$ represents $C_{1-4}$-alkyl which is mono-substituted, wherein the substituent is selected from hydroxy or $C_{1-3}$-alkyl-amino (especially methyl-amino); or di-substituted, wherein the first substituent represents hydroxy, and the second substituent represents $C_1$-fluoroalkyl (especially trifluoromethyl)

[in particular such $C_{1-4}$-alkyl represents 1-hydroxy-1-methyl-ethyl, 1-methyl-1-(methyl-amino)-ethyl, or 1-hydroxy-1-trifluoromethyl-ethyl]; or -L-Cy, wherein -L- represents a direct bond (i.e. Cy is directly attached to the triazolyl ring) or $—CH_2—$ (especially a direct bond); and Cy represents $C_{3-7}$-cycloalkyl optionally containing one ring heteroatom selected from nitrogen or oxygen (notably such Cy represents cyclobutyl, cyclohexyl, tetrahydropyranyl, or piperidinyl; especially cyclobutyl, cyclohexyl, tetrahydropyran-4-yl, or piperidin-4-yl), wherein Cy independently is unsubstituted; or mono-substituted with hydroxy; or -C(═O)$R^A$, wherein $R^A$ represents $C_{1-3}$-alkyl (especially methyl);

or Cy represents a saturated 5- to 8-membered bridged bicyclic hydrocarbon ring system (especially such ring system represents bicyclo[1.1.1]pentan-1-yl or bicyclo[2.2.2]octan-1-yl), wherein Cy independently is mono-substituted (notably at the tertiary carbon atom of said ring system), wherein the substituent is selected from hydroxy-$C_{1-3}$-alkyl (especially hydroxy-methyl); or —C(═O)$R^B$, wherein $R^B$ represents hydroxy; or $C_{1-3}$-alkoxy (especially methoxy);

or Cy represents a 6-membered heteroaryl containing one ring nitrogen atom (especially Cy represents pyridinyl; in particular pyridin-3-yl);

[in particular such -L-Cy group represents tetrahydropyran-4-yl, 4-hydroxy-tetrahydropyran-4-yl, 1-hydroxy-cyclobutyl-methyl, 4-hydroxy-cyclohexyl, pyridin-3-yl, 4-methoxycarbonyl-bicyclo[2.2.2]octan-1-yl, 4-carboxy-bicyclo[2.2.2]octan-1-yl, 3-hydroxymethyl-bicyclo[1.1.1]pentan-1-yl, or N-acetyl-piperidin-4-yl]; and $R^5$ represents $C_{1-4}$-alkyl (especially methyl, ethyl, isopropyl, or tert-butyl);

hydroxy-$C_{1-3}$-alkyl (especially 2-hydroxyethyl);

$C_{3-7}$-cycloalkyl (especially cyclopropyl, cyclobutyl, cyclopentyl, or cyclohexyl); or $C_{1-3}$-fluoroalkyl (especially 2,2-difluoropropyl).

3) A further embodiment relates to compounds according to embodiment 1), wherein Q represents CH.

4) A further embodiment relates to compounds according to embodiment 1), wherein $R^{3b}$ represents hydrogen.

5) A further embodiment relates to compounds according to any one of embodiments 1) to 4), wherein $R^2$ represents $C_{1-4}$-alkyl (especially methyl or isopropyl); or hydroxy-$C_{1-3}$-alkyl (especially 2-hydroxyethyl).

6) A further embodiment relates to compounds according to embodiment 5), wherein $R^2$ represents $C_{1-4}$-alkyl (especially methyl).

7) A further embodiment relates to compounds according to any one of embodiments 1) to 6), wherein $R^{3a}$ represents $C_{1-5}$-alkyl (especially ethyl, n-propyl, isopropyl, or tert-butyl); or $C_{1-3}$-fluoroalkyl (especially 2,2,2-trifluoro-ethyl).

8) A further embodiment relates to compounds according to embodiment 7), wherein $R^{3a}$ represents $C_{1-5}$-alkyl (especially isopropyl).

9) A further embodiment relates to compounds according to any one of embodiments 1) to 8), wherein $R^4$ represents $C_{1-4}$-alkyl which is mono-substituted with hydroxy; or di-substituted, wherein the first substituent represents hydroxy, and the second substituent represents $C_1$-fluoroalkyl (especially trifluoromethyl); or -L-Cy, wherein -L- represents a direct bond (i.e. Cy is directly attached to the triazolyl ring); and Cy represents $C_{3-7}$-cycloalkyl optionally containing one ring heteroatom selected from nitrogen or oxygen (notably such Cy represents cyclohexyl, tetrahydropyranyl, or piperidinyl; especially cyclohexyl, tetrahydropyran-4-yl, or piperidin-4-yl), wherein Cy independently is unsubstituted; or mono-substituted with hydroxy; or —C(═O)$R^A$, wherein $R^A$ represents $C_{1-3}$-alkyl (especially methyl);

or Cy represents bicyclo[1.1.1]pentan-1-yl or bicyclo [2.2.2]octan-1-yl, wherein Cy independently is mono-substituted (notably at the tertiary carbon atom of said ring system), wherein the substituent is selected from hydroxy-$C_{1-3}$-alkyl (especially hydroxy-methyl); or —C(═O)$R^B$, wherein $R^B$ represents hydroxy; or $C_{1-3}$-alkoxy (especially methoxy);

or Cy represents a 6-membered heteroaryl containing one ring nitrogen atom (especially Cy represents pyridinyl; in particular pyridin-3-yl).

10) A further embodiment relates to compounds according to embodiment 9), wherein $R^4$ represents -L-Cy, wherein -L- represents a direct bond (i.e. Cy is directly attached to the triazolyl ring); and Cy represents cyclohexyl, tetrahydropyranyl, or piperidinyl (especially cyclohexyl, tetrahydropyran-4-yl, or piperidin-4-yl), wherein Cy independently is unsubstituted; or mono-substituted with hydroxy; or -C(═O)$R^A$, wherein $R^A$ represents $C_{1-3}$-alkyl (especially methyl);

or Cy represents bicyclo[1.1.1]pentan-1-yl or bicyclo[2.2.2]octan-1-yl, wherein Cy independently is mono-substituted (notably at the tertiary carbon atom of said ring system), wherein the substituent is selected from hydroxy-$C_{1-3}$-alkyl (especially hydroxy-methyl); or —C(═O)$R^B$, wherein $R^B$ represents hydroxy; or $C_{1-3}$-alkoxy (especially methoxy);

or Cy represents pyridinyl (especially pyridin-3-yl).

11) A further embodiment relates to compounds according to any one of embodiments 1) to 10), wherein $R^5$ represents $C_{1-4}$-alkyl (especially methyl, ethyl, isopropyl, or tert-butyl); or $C_{3-7}$-cycloalkyl (especially cyclopropyl, cyclobutyl, cyclopentyl, or cyclohexyl)

[preferred is isopropyl or cyclopropyl].

12) One embodiment relates to compounds according to any one of embodiments 1) to 11), wherein at least one, especially two and in particular all of the following characteristics a), b) and/or c) below are present:

a) the radical

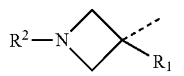

represents 3-methyl-azetidine-3-yl, 1,3-dimethyl-azetidine-3-yl, 1-isopropyl-3-methyl-azetidine-3-yl 1-(2-hydroxyethyl)-3-methyl-azetidine-3-yl, or 1-(2,2-difluoroethyl)-3-methyl-azetidine-3-yl;

b) the radical

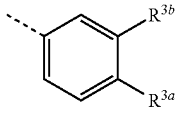

represents 4-bromo-phenyl, 4-ethyl-phenyl, 4-(n-propyl)-phenyl, 4-isopropyl-phenyl, 4-tert-butyl-phenyl, 4-cyclopropyl-phenyl, 4-(2,2,2-trifluoroethyl)-phenyl, 4-trifluoromethoxy-phenyl, or 4-(1-trifluoromethyl-cyclopropyl)-phenyl;

c) the radical

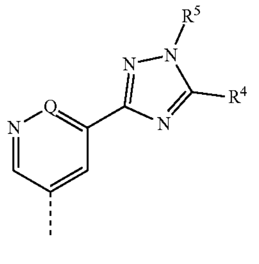

represents 5-(1-cyclopropyl-5-tetrahydropyran-4-yl-1H-1,2,4-triazol-3-yl)-pyridin-3-yl, 5-(1-cyclopropyl- 5-(4-hydroxy-cyclohexyl)-1H-1,2,4-triazol-3-yl)-pyridin-3-yl (especially trans-5-(1-cyclopropyl-5-(4-hydroxy-cyclohexyl)-1H-1,2,4-triazol-3-yl)-pyridin-3-yl), 5-(1-cyclopropyl-5-(1-hydroxy-1-trifluoromethyl-ethyl)-1H-1,2,4-triazol-3-yl)-pyridin-3-yl, 5-(1-cyclopropyl-5-(4-methoxycarbonyl-bicyclo[2.2.2]octan-1-yl)-1H-1,2,4-triazol-3-yl)-pyridin-3-yl, 5-(1-cyclopropyl-5-(1-methyl-1-methylamino-ethyl)-1H-1,2,4-triazol-3-yl)-pyridin-3-yl, 5-(1-cyclopropyl-5-(1-hydroxy-cyclobutyl-methyl)-1H-1,2,4-triazol-3-yl)-pyridin-3-yl, 5-(1-cyclopropyl-5-(4-carboxy-bicyclo[2.2.2]octan-1-yl)-1H-1,2,4-triazol-3-yl)-pyridin-3-yl, 5-(1-cyclohexyl-5-tetrahydropyran-4-yl-1H-1,2,4-triazol-3-yl)-pyridin-3-yl, 5-(1-methyl-5-tetrahydropyran-4-yl-1H-1,2,4-triazol-3-yl)-pyridin-3-yl, 5-(1-(2-hydroxyethyl)-5-tetrahydropyran-4-yl-1H-1,2,4-triazol-3-yl)-pyridin-3-yl, 5-(1-ethyl-5-tetrahydropyran-4-yl-1H-1,2,4-triazol-3-yl)-pyridin-3-yl, 5-(1-isopropyl-5-tetrahydropyran-4-yl-1H-1,2,4-triazol-3-yl)-pyridin-3-yl, 5-(1-cyclopentyl-5-tetrahydropyran-4-yl-1H-1,2,4-triazol-3-yl)-pyridin-3-yl, 5-(1-tert-butyl-5-tetrahydropyran-4-yl-1H-1,2,4-triazol-3-yl)-pyridin-3-yl, 5-(1-(2,2-difluoropropyl)-5-tetrahydropyran-4-yl-1H-1,2,4-triazol-3-yl)-pyridin-3-yl, 5-(1-cyclobutyl-5-tetrahydropyran-4-yl-1H-1,2,4-triazol-3-yl)-pyridin-3-yl, 5-(1-cyclopropyl-5-(pyridin-3-yl)-1H-1,2,4-triazol-3-yl)-pyridin-3-yl, 5-(1-cyclopropyl-5-(1-hydroxy-1-methyl-ethyl)-1H-1,2,4-triazol-3-yl)-pyridin-3-yl, 5-(1-isopropyl-5-(1-hydroxy-1-methyl-ethyl)-1H-1,2,4-triazol-3-yl)-pyridin-3-yl, 5-(1-cyclopropyl-5-(3-(hydroxymethyl)-bicyclo[1.1.1]pentan-1-yl)-1H-1,2,4-triazol-3-yl)-pyridin-3-yl, 5-(1-isopropyl-5-(3-(hydroxymethyl)-bicyclo[1.1.1]pentan-1-yl)-1H-1,2,4-triazol-3-yl)-pyridin-3-yl, 5-(1-cyclopropyl-5-(4-hydroxy-tetrahydropyran-4-yl)-1H-1,2,4-triazol-3-yl)-pyridin-3-yl, 5-(1-isopropyl-5-(4-hydroxy-tetrahydropyran-4-yl)-1H-1,2,4-triazol-3-yl)-pyridin-3-yl, 5-(1-cyclopropyl-5-(N-acetyl-piperidin-4-yl)-1H-1,2,4-triazol-3-yl)-pyridin-3-yl, 5-(1-isopropyl-5-(N-acetyl-piperidin-4-yl)-1H-1,2,4-triazol-3-yl)-pyridin-3-yl, or 5-(1-cyclopropyl-5-(1-hydroxy-1-methyl-ethyl)-1H-1,2,4-triazol-3-yl)-pyridin-3-yl.

13) A further embodiment relates to compounds according to any one of embodiments 1) to 12), wherein the asymmetric carbon atom bearing the hydroxy group has the absolute configuration depicted in Formula (II)

Formula (II)

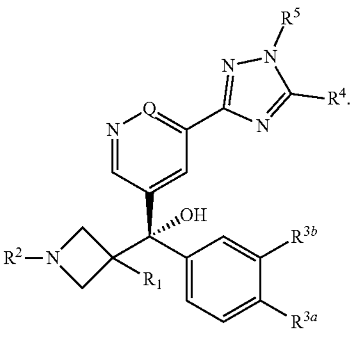

14) Another embodiment relates to compounds according to embodiment 1), which are selected from the following compounds (R)-(4-Bromo-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol;

(R)-(4-tert-Butyl-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-[4-(1-trifluoromethyl-cyclopropyl)-phenyl]-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-trifluoromethoxy-phenyl)-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-[4-(2,2,2-trifluoro-ethyl)-phenyl]-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-ethyl-phenyl)-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-propyl-phenyl)-methanol;

trans-4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-cyclohexanol;

(R)-2-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-1,1,1-trifluoro-propan-2-ol;

4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-bicyclo[2.2.2]octane-1-carboxylic acid methyl ester;

(R)-{5-[1-Cyclopropyl-5-(1-methyl-1-methylamino-ethyl)-1H-[1,2,4]triazol-3-yl]-pyridin-3-yl}-(1,3-dimethyl-azetidin-3-yl)-(4-isopropyl-phenyl)-methanol;

1-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-ylmethyl)-cyclobutanol;

4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-bicyclo[2.2.2]octane-1-carboxylic acid;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-Cyclohexyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-(1,3-Dimethyl-azetidin-3-yl)-(4-isopropyl-phenyl)-{5-[1-methyl-5-(tetrahydro-pyran-4-yl)-1H-[1,2,4]triazol-3-yl]-pyridin-3-yl}-methanol;

2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethanol;

(R)-(1,3-Dimethyl-azetidin-3-yl)-{5-[1-ethyl-5-(tetrahydro-pyran-4-yl)-1H-[1,2,4]triazol-3-yl]-pyridin-3-yl}-(4-isopropyl-phenyl)-methanol;

(R)-(1,3-Dimethyl-azetidin-3-yl)-(4-isopropyl-phenyl)-{5-[1-isopropyl-5-(tetrahydro-pyran-4-yl)-1H-[1,2,4]triazol-3-yl]-pyridin-3-yl}-methanol;

(R)-{5-[1-Cyclopentyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-tert-Butyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-(2,2-Difluoro-propyl)-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-Cyclobutyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-[5-(1-Cyclopropyl-5-pyridin-3-yl-1H-[1,2,4]triazol-3-yl)-pyridin-3-yl]-(1,3-dimethyl-azetidin-3-yl)-(4-isopropyl-phenyl)-methanol;

(R)-(4-Cyclopropyl-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol;

2-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-propan-2-ol;

2-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-propan-2-ol;

(R)-{5-[1-Cyclopropyl-5-(3-hydroxymethyl-bicyclo[1.1.1]pent-1-yl)-1H-[1,2,4]triazol-3-yl]-pyridin-3-yl}-(1,3-dimethyl-azetidin-3-yl)-(4-isopropyl-phenyl)-methanol;

(R)-(1,3-Dimethyl-azetidin-3-yl)-{5-[5-(3-hydroxymethyl-bicyclo[1.1.1]pent-1-yl)-1-isopropyl-1H-[1,2,4]triazol-3-yl]-pyridin-3-yl}-(4-isopropyl-phenyl)-methanol;

4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-tetrahydro-pyran-4-ol;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-tetrahydro-pyran-4-ol;

1-[4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-piperidin-1-yl]-ethanone;

1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-1-yl]-ethanone;

(R)-{5-[1-Cyclopropyl-5-(tetrahydro-pyran-4-yl)-1H-[1,2,4]triazol-3-yl]-pyridin-3-yl}-(1-isopropyl-3-methyl-azetidin-3-yl)-(4-isopropyl-phenyl)-methanol;

(R)-{5-[1-Cyclopropyl-5-(tetrahydro-pyran-4-yl)-1H-[1,2,4]triazol-3-yl]-pyridin-3-yl}-[1-(2,2-difluoro-ethyl)-3-methyl-azetidin-3-yl]-(4-isopropyl-phenyl)-methanol;

2-{3-[(R)-{5-[1-Cyclopropyl-5-(tetrahydro-pyran-4-yl)-1H-[1,2,4]triazol-3-yl]-pyridin-3-yl}-hydroxy-(4-isopropyl-phenyl)-methyl]-3-methyl-azetidin-1-yl}-ethanol; or 2-(2-Cyclopropyl-5-{5-[(R)-hydroxy-(4-isopropyl-phenyl)-(3-methyl-azetidin-3-yl)-methyl]-pyridin-3-yl}-2H-[1,2,4]triazol-3-yl)-propan-2-ol.

15) Another embodiment relates to compounds according to embodiment 1), which are selected from the following compounds (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(3-fluoro-4-isopropyl-phenyl)-methanol;

4-(2-Cyclopropyl-5-{5-[(R)-(1,3-dimethyl-azetidin-3-yl)-hydroxy-(4-isopropyl-phenyl)-methyl]-2-fluoro-pyridin-3-yl}-2H-[1,2,4]triazol-3-yl)-trans-cyclohexanol;

4-(2-Cyclopropyl-5-{5-[(R)-(1,3-dimethyl-azetidin-3-yl)-hydroxy-(4-isopropyl-phenyl)-methyl]-2-methyl-pyridin-3-yl}-2H-[1,2,4]triazol-3-yl)-trans-cyclohexanol;

(R)-(1,3-Dimethyl-azetidin-3-yl)-(4-isopropyl-phenyl)-[5-(1-isopropyl-5-propyl-1H-[1,2,4]triazol-3-yl)-pyridin-3-yl]-methanol;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-1-methyl-piperidin-2-one;

N-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-trans-cyclohexyl]-acetamide;

1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-1-yl]-2-hydroxy-ethanone;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-4-methyl-piperidin-2-one;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-2-one;

1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-4-hydroxy-piperidin-1-yl]-ethanone;

(R)-(1,3-Dimethyl-azetidin-3-yl)-(4-isopropyl-phenyl)-{5-[1-(2-methoxy-ethyl)-5-(tetrahydro-pyran-4-yl)-1H-[1,2,4]triazol-3-yl]-pyridin-3-yl}-methanol;

(R)-(1-Cyclopropyl-3-methyl-azetidin-3-yl)-{5-[1-cyclopropyl-5-(tetrahydro-pyran-4-yl)-1H-[1,2,4]triazol-3-yl]-pyridin-3-yl}-(4-isopropyl-phenyl)-methanol;

N-{2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethyl}-acetamide; or (R)-(1,3-Dimethyl-azetidin-3-yl)-(4-isopropyl-phenyl)-{6-[1-isopropyl-5-(tetrahydro-pyran-4-yl)-1H-[1,2,4]triazol-3-yl]-pyridazin-4-yl}-methanol.

Based on the dependencies of the different embodiments 1) to 13) as disclosed hereinabove, the following embodiments are thus possible and intended, and herewith specifically disclosed in individualized form:

2+1, 3+1, 4+1, 5+1, 5+2+1, 5+3+1, 5+4+1, 6+5+1, 6+5+2+1, 6+5+3+1, 6+5+4+1, 7+1, 7+2+1, 7+3+1, 7+4+1, 7+5+1, 7+5+2+1, 7+5+3+1, 7+5+4+1, 7+6+5+1, 7+6+5+2+1, 7+6+5+3+1, 7+6+5+4+1, 8+7+1, 8+7+2+1, 8+7+3+1, 8+7+4+1, 8+7+5+1, 8+7+5+2+1, 8+7+5+3+1, 8+7+5+4+1, 8+7+6+5+1, 8+7+6+5+2+1, 8+7+6+5+3+1, 8+7+6+5+4+1, 9+1, 9+2+1, 9+3+1, 9+4+1, 9+5+1, 9+5+2+1, 9+5+3+1, 9+5+4+1, 9+6+5+1, 9+6+5+2+1, 9+6+5+3+1, 9+6+5+4+1, 9+7+1, 9+7+2+1, 9+7+3+1, 9+7+4+1, 9+7+5+1, 9+7+5+2+1, 9+7+5+3+1, 9+7+5+4+1, 9+7+6+5+1, 9+7+6+5+2+1, 9+7+6+5+3+1, 9+7+6+5+4+1, 9+8+7+1, 9+8+7+2+1, 9+8+7+3+1, 9+8+7+4+1, 9+8+7+5+1, 9+8+7+5+2+1, 9+8+7+5+3+1, 9+8+7+5+4+1, 9+8+7+6+5+1, 9+8+7+6+5+2+1, 9+8+7+6+5+3+1, 9+8+7+6+5+4+1, 10+9+1, 10+9+2+1, 10+9+3+1, 10+9+4+1, 10+9+5+1, 10+9+5+2+1, 10+9+5+3+1, 10+9+5+4+1, 10+9+6+5+1, 10+9+6+5+2+1, 10+9+6+5+3+1, 10+9+6+5+4+1, 10+9+7+1, 10+9+7+2+1, 10+9+7+3+1, 10+9+7+4+1, 10+9+7+5+1, 10+9+7+5+2+1, 10+9+7+5+3+1, 10+9+7+5+4+1, 10+9+7+6+5+1, 10+9+7+6+5+2+1, 10+9+7+6+5+3+1, 10+9+7+6+5+4+1, 10+9+8+7+1, 10+9+8+7+2+1, 10+9+8+7+3+1, 10+9+8+7+4+1, 10+9+8+7+5+1, 10+9+8+7+5+2+1, 10+9+8+7+5+3+1, 10+9+8+7+5+4+1, 10+9+8+7+6+5+1, 10+9+8+7+6+5+2+1, 10+9+8+7+6+5+3+1, 10+9+8+7+6+5+4+1, 11+1, 11+2+1, 11+3+1, 11+4+1, 11+5+1, 11+5+2+1, 11+5+3+1, 11+5+4+1, 11+6+5+1, 11+6+5+2+1, 11+6+5+3+1, 11+6+5+4+1, 11+7+1, 11+7+2+1, 11+7+3+1, 11+7+4+1, 11+7+5+1, 11+7+5+2+1, 11+7+5+3+1, 11+7+5+4+1, 11+7+6+5+1, 11+7+6+5+2+1, 11+7+6+5+3+1, 11+7+6+5+4+1, 11+8+7+1, 11+8+7+2+1, 11+8+7+3+1, 11+8+7+4+1, 11+8+7+5+1, 11+8+7+5+2+1, 11+8+7+5+3+1, 11+8+7+5+4+1, 11+8+7+6+5+1, 11+8+7+

6+5+2+1, 11+8+7+6+5+3+1, 11+8+7+6+5+4+1, 11+9+1, 11+9+2+1, 11+9+3+1, 11+9+4+1, 11+9+5+1, 11+9+5+2+1, 11+9+5+3+1, 11+9+5+4+1, 11+9+6+5+1, 11+9+6+5+2+1, 11+9+6+5+3+1, 11+9+6+5+4+1, 11+9+7+1, 11+9+7+2+1, 11+9+7+3+1, 11+9+7+4+1, 11+9+7+5+1, 11+9+7+5+2+1, 11+9+7+5+3+1, 11+9+7+5+4+1, 11+9+7+6+5+1, 11+9+7+6+5+2+1, 11+9+7+6+5+3+1, 11+9+7+6+5+4+1, 11+9+8+7+1, 11+9+8+7+2+1, 11+9+8+7+3+1, 11+9+8+7+4+1, 11+9+8+7+5+1, 11+9+8+7+5+2+1, 11+9+8+7+5+3+1, 11+9+8+7+5+4+1, 11+9+8+7+6+5+1, 11+9+8+7+6+5+2+1, 11+9+8+7+6+5+3+1, 11+9+8+7+6+5+4+1, 11+10+9+1, 11+10+9+2+1, 11+10+9+3+1, 11+10+9+4+1, 11+10+9+5+1, 11+10+9+5+2+1, 11+10+9+5+3+1, 11+10+9+5+4+1, 11+10+9+6+5+1, 11+10+9+6+5+2+1, 11+10+9+6+5+3+1, 11+10+9+6+5+4+1, 11+10+9+7+1, 11+10+9+7+2+1, 11+10+9+7+3+1, 11+10+9+7+4+1, 11+10+9+7+5+1, 11+10+9+7+5+2+1, 11+10+9+7+5+3+1, 11+10+9+7+5+4+1, 11+10+9+7+6+5+1, 11+10+9+7+6+5+2+1, 11+10+9+7+6+5+3+1, 11+10+9+7+6+5+4+1, 11+10+9+8+7+1, 11+10+9+8+7+2+1, 11+10+9+8+7+3+1, 11+10+9+8+7+4+1, 11+10+9+8+7+5+1, 11+10+9+8+7+5+2+1, 11+10+9+8+7+5+3+1, 11+10+9+8+7+5+4+1, 11+10+9+8+7+6+5+1, 11+10+9+8+7+6+5+2+1, 11+10+9+8+7+6+5+3+1, 11+10+9+8+7+6+5+4+1, 12+1, 13+1, 13+2+1, 13+3+1, 13+4+1, 13+5+1, 13+5+2+1, 13+5+3+1, 13+5+4+1, 13+6+5+1, 13+6+5+2+1, 13+6+5+3+1, 13+6+5+4+1, 13+7+1, 13+7+2+1, 13+7+3+1, 13+7+4+1, 13+7+5+1, 13+7+5+2+1, 13+7+5+3+1, 13+7+5+4+1, 13+7+6+5+1, 13+7+6+5+2+1, 13+7+6+5+3+1, 13+7+6+5+4+1, 13+8+7+1, 13+8+7+2+1, 13+8+7+3+1, 13+8+7+4+1, 13+8+7+5+1, 13+8+7+5+2+1, 13+8+7+5+3+1, 13+8+7+5+4+1, 13+8+7+6+5+1, 13+8+7+6+5+2+1, 13+8+7+6+5+3+1, 13+8+7+6+5+4+1, 13+9+1, 13+9+2+1, 13+9+3+1, 13+9+4+1, 13+9+5+1, 13+9+5+2+1, 13+9+5+3+1, 13+9+5+4+1, 13+9+6+5+1, 13+9+6+5+2+1, 13+9+6+5+3+1, 13+9+6+5+4+1, 13+9+7+1, 13+9+7+2+1, 13+9+7+3+1, 13+9+7+4+1, 13+9+7+5+1, 13+9+7+5+2+1, 13+9+7+5+3+1, 13+9+7+5+4+1, 13+9+7+6+5+1, 13+9+7+6+5+2+1, 13+9+7+6+5+3+1, 13+9+7+6+5+4+1, 13+9+8+7+1, 13+9+8+7+2+1, 13+9+8+7+3+1, 13+9+8+7+4+1, 13+9+8+7+5+1, 13+9+8+7+5+2+1, 13+9+8+7+5+3+1, 13+9+8+7+5+4+1, 13+9+8+7+6+5+1, 13+9+8+7+6+5+2+1, 13+9+8+7+6+5+3+1, 13+9+8+7+6+5+4+1, 13+10+9+1, 13+10+9+2+1, 13+10+9+3+1, 13+10+9+4+1, 13+10+9+5+1, 13+10+9+5+2+1, 13+10+9+5+3+1, 13+10+9+5+4+1, 13+10+9+6+5+1, 13+10+9+6+5+2+1, 13+10+9+6+5+3+1, 13+10+9+6+5+4+1, 13+10+9+7+1, 13+10+9+7+2+1, 13+10+9+7+3+1, 13+10+9+7+4+1, 13+10+9+7+5+1, 13+10+9+7+5+2+1, 13+10+9+7+5+3+1, 13+10+9+7+5+4+1, 13+10+9+7+6+5+1, 13+10+9+7+6+5+2+1, 13+10+9+7+6+5+3+1, 13+10+9+7+6+5+4+1, 13+10+9+8+7+1, 13+10+9+8+7+2+1, 13+10+9+8+7+3+1, 13+10+9+8+7+4+1, 13+10+9+8+7+5+1, 13+10+9+8+7+5+2+1, 13+10+9+8+7+5+3+1, 13+10+9+8+7+5+4+1, 13+10+9+8+7+6+5+1, 13+10+9+8+7+6+5+2+1, 13+10+9+8+7+6+5+3+1, 13+10+9+8+7+6+5+4+1, 13+11+1, 13+11+2+1, 13+11+3+1, 13+11+4+1, 13+11+5+1, 13+11+5+2+1, 13+11+5+3+1, 13+11+5+4+1, 13+11+6+5+1, 13+11+6+5+2+1, 13+11+6+5+3+1, 13+11+6+5+4+1, 13+11+7+1, 13+11+7+2+1, 13+11+7+3+1, 13+11+7+4+1, 13+11+7+5+1, 13+11+7+5+2+1, 13+11+7+5+3+1, 13+11+7+5+4+1, 13+11+7+6+5+1, 13+11+7+6+5+2+1, 13+11+7+6+5+3+1, 13+11+7+6+5+4+1, 13+11+8+7+1, 13+11+8+7+2+1,

13+11+8+7+3+1, 13+11+8+7+4+1, 13+11+8+7+5+1, 13+11+8+7+5+2+1, 13+11+8+7+5+3+1, 13+11+8+7+5+4+1, 13+11+8+7+6+5+1, 13+11+8+7+6+5+2+1, 13+11+8+7+6+5+3+1, 13+11+8+7+6+5+4+1, 13+11+9+1, 13+11+9+2+1, 13+11+9+3+1, 13+11+9+4+1, 13+11+9+5+1, 13+11+9+5+2+1, 13+11+9+5+3+1, 13+11+9+5+4+1, 13+11+9+6+5+1, 13+11+9+6+5+2+1, 13+11+9+6+5+3+1, 13+11+9+6+5+4+1, 13+11+9+7+1, 13+11+9+7+2+1, 13+11+9+7+3+1, 13+11+9+7+4+1, 13+11+9+7+5+1, 13+11+9+7+5+2+1, 13+11+9+7+5+3+1, 13+11+9+7+5+4+1, 13+11+9+7+6+5+1, 13+11+9+7+6+5+2+1, 13+11+9+7+6+5+3+1, 13+11+9+7+6+5+4+1, 13+11+9+8+7+1, 13+11+9+8+7+2+1, 13+11+9+8+7+3+1, 13+11+9+8+7+4+1, 13+11+9+8+7+5+1, 13+11+9+8+7+5+2+1, 13+11+9+8+7+5+3+1, 13+11+9+8+7+5+4+1, 13+11+9+8+7+6+5+1, 13+11+9+8+7+6+5+2+1, 13+11+9+8+7+6+5+3+1, 13+11+9+8+7+6+5+4+1, 13+11+10+9+1, 13+11+10+9+2+1, 13+11+10+9+3+1, 13+11+10+9+4+1, 13+11+10+9+5+1, 13+11+10+9+5+2+1, 13+11+10+9+5+3+1, 13+11+10+9+5+4+1, 13+11+10+9+6+5+1, 13+11+10+9+6+5+2+1, 13+11+10+9+6+5+3+1, 13+11+10+9+6+5+4+1, 13+11+10+9+7+1, 13+11+10+9+7+2+1, 13+11+10+9+7+3+1, 13+11+10+9+7+4+1, 13+11+10+9+7+5+1, 13+11+10+9+7+5+2+1, 13+11+10+9+7+5+3+1, 13+11+10+9+7+5+4+1, 13+11+10+9+7+6+5+1, 13+11+10+9+7+6+5+2+1, 13+11+10+9+7+6+5+3+1, 13+11+10+9+7+6+5+4+1, 13+11+10+9+8+7+1, 13+11+10+9+8+7+2+1, 13+11+10+9+8+7+3+1, 13+11+10+9+8+7+4+1, 13+11+10+9+8+7+5+1, 13+11+10+9+8+7+5+2+1, 13+11+10+9+8+7+5+3+1, 13+11+10+9+8+7+5+4+1, 13+11+10+9+8+7+6+5+1, 13+11+10+9+8+7+6+5+2+1, 13+11+10+9+8+7+6+5+3+1, 13+11+10+9+8+7+6+5+4+1, or 13+12+1.

In the list above the numbers refer to the embodiments according to their numbering provided hereinabove whereas "+" indicates the dependency from another embodiment. The different individualized embodiments are separated by commas. In other words, "6+5+2+1," for example refers to embodiment 6) depending on embodiment 5), depending on embodiment 2), depending on embodiment 1), i.e. embodiment "6+5+2+1" corresponds to the compounds of Formula (I) according to embodiment 1) further limited by all the features of the embodiments 2), 5), and 6).

The invention relates to compounds of the Formula (I) as defined in embodiment 1), or to such compounds further limited by the characteristics of any one of embodiments 2) to 13), under consideration of their respective dependencies; to pharmaceutically acceptable salts thereof; and to the use of such compounds as medicaments especially in the treatment of diseases or disorders where CCR6 receptors are involved as described hereinbelow.

The present invention also includes isotopically labelled, especially $^{2}H$ (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^{2}H$ (deuterium) labelled compounds of Formula (I) and salts thereof are within the scope of the present invention. Substitution of hydrogen with the heavier isotope $^{2}H$ (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms.

In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Where the plural form is used for compounds, salts, pharmaceutical compositions, diseases and the like, this is intended to mean also a single compound, salt, pharmaceutical composition, disease or the like.

Any reference to compounds of Formula (I) according to embodiments 1) to 15) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of Formula (I), as defined in any one of embodiments 1) to 13), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of Formula (I) may encompass compounds with one or more asymmetric centers, such as one or more asymmetric carbon atoms, which may be present in (R)- as well as (S)-configuration. The compounds of Formula (I) may further encompass compounds with one or more double bonds which are allowed to be present in Z- as well as E-configuration and/or compounds with substituents at a ring system which are allowed to be present, relative to each other, in cis- as well as trans-configuration. The compounds of Formula (I) may thus be present as mixtures of stereoisomers or preferably in stereoisomerically enriched form, especially as essentially pure stereoisomers. Mixtures of stereoisomers may be separated in a manner known to a person skilled in the art.

In case a particular compound (or generic structure) is designated as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations are to be understood as referring to the respective stereoisomer in enriched, especially essentially pure, form. Likewise, in case a particular compound (or generic structure) is designated as Z- or E-stereoisomer (or in case a specific double bond in a compound is designated as being in Z- or E-configuration), such designation is to be understood as referring to the respective compound (or generic structure) in enriched, especially essentially pure, stereoisomeric form (or to the compound that is in enriched, especially essentially pure, form with regard to the respective configuration of the double bond).

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The compounds of Formula (I) according to embodiments 1) to 15) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively the term "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

The compounds of Formula (I) as defined hereinabove are useful for the prevention or treatment of various diseases, conditions or disorders ameliorated by modulating CCR6 receptors. Such diseases, conditions, or disorders, where CCR6 receptors are involved may be defined as inflammatory and/or autoimmune diseases, conditions, or disorders; and cancer.

The compounds of Formula (I) as defined hereinabove are useful for the prevention or treatment of of various diseases, conditions, or disorders, ameliorated by modulating CCR6 receptors. Such diseases, conditions, or disorders, where CCR6 receptors are involved may be defined as inflammatory/autoimmune diseases, conditions, or disorders, including rheumatoid arthritis; ankylosing spondylitis; spondyloarthritis; psoriasis; psoriatic arthritis; inflammatory skin disorders such as rosacea; Crohn's disease; ulcerative colitis; inflammatory bowel disease; irritable bowel disease; dry eye disease; multiple sclerosis; systemic lupus erythematosus; Sjögren's disease; autoimmune hepatitis; Primary Sclerosing Cholangitis; Posterior uveitis; allergic conjunctivitis; allergic disease in the gastrointestinal tract; type I diabetes and endometriosis; diseases of the ocular surface in which elevated levels of IL-17A have been recorded such as meibomian gland dysfunction; GVHD; graft-versus host disease; autoimmune keratitis; filamentary keratitis; dry eye syndrome with rheumatic arthritis; dry eye syndrome without systemic disease; Stevens-Johnson syndrome; psoriasis including plaque psoriasis, guttate psoriasis, inverse psoriasis, pustular psoriasis, erythrodermic psoriasis; autoimmune keratitis; filamentary keratitis; autoimmune uveitis; allergic conjunctivitis; asthma; allergic disease of the gastrointestinal tract; T1D; endometriosis; meibomian gland dysfunction; graft-versus host disease; juvenile arthritis; juvenile rheumatoid arthritis; systemic onset rheumatoid arthritis; pauciarticular rheumatoid arthritis; pauciarticular juvenile rheumatoid arthritis; polyarticular rheumatoid arthritis; enteropathic arthritis; juvenile Reiter's Syndrome; ankylosing spondylitis; juvenile ankylosing spondylitis; SEA Syndrome; reactive arthritis (reactive arthropathy); psoriatic arthropathy; juvenile enteropathic arthritis; polymyalgia rheumatica; enteropathic spondylitis; juvenile idiopathic arthritis (JIA); juvenile psoriatic arthritis; juvenile rheumatoid arthritis; systemic onset juvenile rheumatoid arthritis; acute pancreatitis; chronic pancreatitis; giant cell arteritis; atherosclerosis; bone erosion; intraperotoneal abscesses; intraperitoneal abscesses; and/or secondary osteoarthritis from inflammatory diseases.

Further, such diseases, conditions, or disorders, ameliorated by modulating CCR6 receptors may be defined as including cancer such as skin cancer e.g. melanoma (superficial spreading, nodular, lentigo maligna and acral lentiginous melanoma); advanced melanoma; metastatic melanoma; Merkel cell carcinoma; Kaposi sarcoma; basal cell carcinoma; squamous cell carcinoma; and pre-cancerous skin lesions such as actinic keratosis; lung cancer including small cell lung cancer and non-small (SCLC, NSCLC) such as squamous and non-squamous NSCLC; pleuropulmonary blastoma and tracheobronchial tumors; bladder cancer including urinary bladder cancer; urothelial cell carcinoma; mesothelioma; renal carcinomas including renal cell carcinoma (RCC) such as clear cell RCC; papillary RCC; chromophobe RCC; non-clear cell RCC; unclassified RCC; metastatic renal cell carcinoma; metastatic renal clear cell carcinoma; renal parenchymal carcinoma; gastro-intestinal cancers including colorectal cancer; metastatic colorectal cancer; familial adenomatous polyposis (FAP); rectum carcinoma; colon carcinoma; colorectal adenoma; colorectal adenocarcinoma; colorectal cancer liver metastases; hereditary non-polyposis colorectal cancer; esophageal cancer; gastric cancer; advanced gastric cancer; gallbladder cancer; cholangiocarcinoma; hepatocellular carcinoma; pancreatic cancer such as pancreatic adenocarcinoma or pancreatic ductal (adeno)carcinoma; pancreatic neuroendocrine tumors; endometrial cancer; ovarian cancer; prostate cancer including castrate-resistant prostate cancer; brain tumors including brain metastases, malignant gliomas, glioblastoma multiforme, medulloblastoma, meningiomas, astrocytoma; peripheral neuroectodermal tumors; oligoastrocytic tumors; oligodendrogliomas; ependymal tumors; anaplastic astrocytoma; pilocytic astrocytoma; craniopharyngioma; spinal cord tumors; brain stem glioma; central nervous system atypical teratoid/rhabdoid tumor; medulloblastoma; central nervous system germ cell tumors; craniopharyngioma; ependymoma; neuroblastoma; head and neck cancer such as esthesioneuroblastoma; cervical cancer; advanced cervical cancer; breast cancer including normal-like, basal-like, claudin-low, HER2 positive, luminal-A, luminal-B and triple negative breast carcinoma; pregnancy breast cancer and male breast cancer; oral tumors; nasopharyngeal tumors; heart tumors; thoracic cancer; lymphomas such as Hodgkin lymphoma, non-Hodgkin lymphoma, Burkitt lymphoma; primary intra-ocular B-Cell lymphoma; diffuse large B-cell lymphoma; primary mediastinal large B-cell lymphoma; mucosa-associated lymphoid tissue (MALT) lymphoma; gastric MALT lymphoma; cutaneous T-cell lymphoma; primary central nervous system lymphoma; Sézary syndrome and Waldenström macroglobulinemia; leukemia such as acute lymphoblastic leukemia; acute myeloid leukemia; chronic lymphocytic leukemia; chronic myelogenous leukemia; hairy cell leukemia; chronic myeloid leukemia; adult T-cell leukemia; carcinomas; adenocarcinomas; thyroid carcinoma including papillary thyroid carcinoma and medullary thyroid carcinoma choriocarcinoma; sarcomas including Ewing's sarcoma; bone cancer such as osteosarcoma; high-grade osteosarcoma; rhabdomyosarcoma; Ewing sarcoma; malignant fibrous histiocytoma of the bone; chordoma; soft tissue sarcoma; myeloma; multiple myelomas; labial carcinoma; larynx carcinoma; hypopharynx carcinoma; tongue carcinoma; salivary gland carcinoma; cervix carcinoma; uterine corpus carcinoma; endometrium carcinoma; chorion carcinoma; testis carcinoma; urinary carcinoma; bronchial carcinoma; basalioma; teratoma; retinoblastoma; choroid melanoma; seminoma; chondrosarcoma; myosarcoma; liposarcoma; fibrosarcoma; plasmacytoma; hepatocarcinoma; advanced liver cancer; gastrointestinal stromal tumors; neuroendocrine tumors; bile duct cancer; appendix cancer; gastrointestinal carcinoid tumor; carcinoid tumor; islet cell tumor; small intestine cancer; stomach cancer; adrenocortical carcinoma; parathyroid cancer; paraganglioma; pheochromocytoma; pituitary tumor; penile cancer; renal pelvis and ureter cancer; testicular cancer; urethral cancer; Wilms tumor; extracranial germ cell tumor; extragonadal germ cell tumor; fallopian tube cancer; gestational trophoblastic tumor; primary peritoneal cancer; vaginal cancer; vulvar cancer; hypopharyngeal cancer; laryngeal cancer; papillomatosis cancer; lip and oral cavity cancer; metastatic squamous neck cancer; mouth cancer; nasopharyngeal cancer; oropharyngeal cancer; paranasal sinus and nasal cavity and paranasal sinus cancer; parathyroid cancer; pharyngeal cancer; throat cancer; chronic myeloproliferative neoplasm; Langerhans cell histiocytosis; plasma cell neoplasm; myelodysplastic syndromes; myeloproliferative neoplasm; midline tract carcinoma; virally induced tumors; and/or diseases involving CCR6 and/or CCL20 mediated metastasis, chemotaxis, cell adhesion, trans-endothelial migration, cell proliferation and/or survival.

Notably, such diseases, conditions, or disorders, ameliorated by modulating CCR6 receptors are selected from inflammatory/autoimmune diseases, conditions, or disorders, such as rheumatoid arthritis; ankylosing spondylitis; spondyloarthritis; psoriasis; psoriatic arthritis; inflammatory skin disorders e.g. rosacea; Crohn's disease; ulcerative colitis; irritable bowel disease; inflammatory bowel disease; dry eye disease; multiple sclerosis; systemic lupus erythematosus; Sjögren's disease; autoimmune hepatitis; Primary Sclerosing Cholangitis;

psoriasis including plaque psoriasis, guttate psoriasis, inverse psoriasis, pustular psoriasis, erythrodermic psoriasis; autoimmune keratitis; filamentary keratitis; autoimmune uveitis; allergic conjunctivitis; asthma; allergic disease of the gastrointestinal tract; type 1 diabetes (T1D); endometriosis; meibomian gland dysfunction; and/or graft-versus host disease; and/or cancer such as lymphoma including T cell lymphoma and primary mediastinal B-cell lymphoma; brain cancer including glioma and glioblastoma; breast cancer including triple negative breast cancer; colorectal cancer; hepatocarcinoma; renal cell carcinoma; lung cancer including non-small cell lung cancer and small cell lung cancer; gastric cancer; melanoma including Merkel cell carcinoma, cutaneous squamous cell carcinoma and malignant melanoma; bladder cancer; head and neck cancer including squamous cell head and neck carcinoma; Hodgkin's lymphoma; cervical cancer; endometrial cancer; colon cancer; gastrointestinal stromal tumors; pancreatic cancer; prostatic cancer; leukemia including acute myeloid leukemia; ovarian cancer; oesophageal carcinomas; mesothelioma; neuroblastoma; sarcoma e.g. high-grade osteosarcoma; astrocytoma; myeloma; urothelial cancer including locally advanced and metastatic urothelial cancer; MSI-H or dMMR cancer; rectal cancer; laryngeal cancer; salivary adenocarcinoma; multiple myeloma; cholangiocarcinoma; oral squamous cell carcinoma; thyroid cancer; and/or esophagogastric junction cancer.

Especially, such diseases, conditions, or disorders, ameliorated by modulating CCR6 receptors are selected from inflammatory/autoimmune diseases, conditions, or disorders, such as psoriasis; psoriatic arthritis; rheumatoid arthritis; ankylosing spondylitis; spondyloarthritis; inflammatory skin disorders e.g. rosacea; Crohn's disease; ulcerative colitis; irritable bowel disease; inflammatory bowel disease; dry eye disease; multiple sclerosis; systemic lupus erythematosus; Sjögren's disease; autoimmune hepatitis; and/or Primary Sclerosing Cholangitis; In particular, such diseases, conditions, or disorders, are psoriasis, psoriatic arthritis, or inflammatory bowel disease; and especially may be selected from A1) psoriasis or psoriatic arthritis; or A2) inflammatory bowel disease; and/or cancer such as lymphoma (e.g. T cell lymphoma); brain cancer (e.g. glioma or glioblastoma); breast cancer; colorectal cancer; hepatocarcinomas; renal cell carcinoma; lung cancer; and/or gastric cancer.

When used for the prevention/prophylaxis or treatment of a cancer, such use includes use of the compounds of Formula (I) as single therapeutic agents and their use in combination with one or more chemotherapy agents and/or radiotherapy and/or targeted therapy (especially in combination with targeted therapy).

The terms "radiotherapy" or "radiation therapy" or "radiation oncology", refer to the medical use of ionizing radiation in the prevention/prophylaxis (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or inhibit angiogenesis, the growth and formation of new blood vessels in the tumor; or deliver toxic substances directly to cancer cells and kill them. An example of a targeted therapy which is in particular suitable to be combined with the compounds of Formula (I) is immunotherapy, especially immunotherapy targeting the programmed cell death receptor 1 (PD-1 receptor) or its ligand PD-L1.

Immunotherapy further refers to (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators). Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-HI (PD-LI), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-IBBL, CD137 (4-IBB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTpR, LIGHT, DcR3, HVEM, VEGI/TLIA, TRAMP/DR3, EDAR, EDAI, XEDAR, EDA2, TNFRI, Lymphotoxin a/TNFp, TNFR2, TNFa, LTPR, Lymphotoxin a 1p2, FAS, FASL, RELT, DR6, TROY, NGFR.

When used in combination with the compounds of Formula (I), the term "targeted therapy" especially refers to agents such as:

a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab) as well as trastuzumab (HERCEPTIN);

b) RAS/RAF/MEK pathway inhibitors (for example Vemurafenib, Sorafenib, Dabrafenib, GDC-0879, PLX-4720, LGX818, RG7304, Trametinib (GSK1120212), Cobimetinib (GDC-0973/XL518), Binimetinib (MEK162, ARRY-162), Selumetinib (AZD6244));

c) Janus kinase (JAK) inhibitors (for example Ruxolitinib, Itacitinib, Momelotinib); d) Aromatase inhibitors (for example Exemestane, Letrozole, Anastrozole, Vorozole, Formestane, Fadrozole);

e) signal transduction inhibitors (STI). A "signal transduction inhibitor" is an agent that selectively inhibits one or more vital steps in signaling pathways, in the normal function of cancer cells, thereby leading to apoptosis. Suitable STis include but are not limited to: (i) bcr/abl kinase inhibitors such as, for example, STI 571 (GLEEVEC®), Dasatinib; (ii) epidermal growth factor (EGF) receptor inhibitors such as, for example, kinase inhibitors (IRESSA®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as famesyl transferase inhibitors (FTI) such as, for example, L-744,832 (Kohl et al., Nat. Med., 1(8):792-797 (1995)); (iv) inhibitors of Akt family kinases or the Akt pathway, such as, for example, rapamycin (see, for example, Sekulic et al., Cancer Res., 60:3504-3513 (2000)); (v)

cell cycle kinase inhibitors such as, for example, flavopiridol and UCN-01 (see, for example, Sausville, Curr. Med. Chem. Anti-Canc. Agents, 3:47-56 (2003)); and (vi) phosphatidyl inositol kinase inhibitors such as, for example, LY294002 (see, for example, Vlahos et al., J Biol. Chem., 269:5241-5248 (1994)).

f) Angiogenesis inhibitors, especially VEGF signalling inhibitors such as Bevacuzimab (Avastin), Ramucirumab, Sorafenib or Axitinib;

g) Immune Checkpoint inhibitors (for example: anti-PD1 antibodies such as Pembrolizumab (Lambrolizumab, MK-3475), Nivolumab, Pidilizumab (CT-011), AMP-514/MEDI0680, PDR001, SHR-1210; REGN2810, BGBA317, PF-06801591, MGA-012, TSR042, JS-001, BCD100, IBI-308, BI-754091; fusion proteins targeting PD-1 such as AMP-224; small molecule anti-PD1 agents such as for example compounds disclosed in WO2015/033299, WO2015/044900 and WO2015/034820; anti-PD1L antibodies, such as BMS-936559, atezolizumab (MPDL3280A, RG7446), avelumab (MSB0010718C), durvalumab (MEDI4736); anti-PDL2 antibodies, such as AMP224; anti-CTLA-4 antibodies, such as ipilimumab, tremelimumab; anti-Lymphocyte-activation gene 3 (LAG-3) antibodies, such as Relatlimab (BMS-986016), IMP701, IMP731, MK-4280, ImmuFact IMP321; anti T cell immunoglobulin mucin-3 (TIM-3) antibodies, such as MBG453, TSR-022; anti T cell immunoreceptor with Ig and ITIM domains (TIGIT) antibodies, such as RG6058 (anti-TIGIT, MTIG7192A); anti-Killer-cell immunoglobulin-like receptors (KIR) for example Lirilumab (IPH2102/BMS-986015), antagonists of Galectins (such as Galectin-1, Galectin-9), BTLA;

h) Vaccination approaches (for example dendritic cell vaccination, DNA, peptide or protein vaccination (for example with gp100 peptide or MAGE-A3 peptide) as well as recombinant viruses;

i) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX);

j) T-cell based adoptive immunotherapies, including chimeric antigen receptor (CAR) engineered T-cells (for example CTL019);

k) Cytokine or immunocytokine based therapy (for example Interferon alpha, interferon beta, interferon gamma, interleukin 2, interleukin 6, interleukin 10, interleukin 15, TGF-β);

l) Toll-like receptor (TLR) agonists (for example resiquimod, imiquimod, motolimod, glucopyranosyl lipid A, CpG oligodesoxynucleotides);

m) Thalidomide analogues (for example Lenalidomide, Pomalidomide);

n) Activators of T-cell co-stimulatory receptors (for example anti-CD137/4-1BB antibodies, such as BMS-663513 (urelumab), Utomilumab (PF-05082566); anti-OX40/CD134 (Tumor necrosis factor receptor superfamily, member 4) (such as RG7888 (MOXR0916), 9B12; MEDI6469, GSK3174998, MEDI6383, MEDI0562), anti OX40-Ligand/CD252; anti-glucocorticoid-induced TNFR family related gene (GITR) (such as TRX518, MEDI1873, MK-4166, BMS-986156, BMS-986153), anti-CD40 (TNF receptor superfamily member 5) antibodies (such as Dacetuzumab (SGN-40), HCD122, CP-870,893, RG7876, ADC-1013, APX005M, SEA-CD40); anti-CD40-Ligand antibodies (such as BG9588); anti-CD27 antibodies such as Varlilumab; anti-CD28 antibodies; anti-ICOS antibodies;

o) Molecules binding a tumor specific antigen as well as a T-cell surface marker such as bispecific antibodies or antibody fragments, antibody mimetic proteins such as designed ankyrin repeat proteins (DARPINS), bispecific T-cell engager (BITE, for example AMG103, AMG330);

p) Antibodies or small molecular weight inhibitors targeting colony-stimulating factor-1 receptor (CSF-1R) (for example Emactuzumab (RG7155), Cabiralizumab (FPA-008), PLX3397);

q) Agents targeting immune cell check points on natural killer cells such as antibodies against Killer-cell immunoglobulin-like receptors (KIR) for example Lirilumab (IPH2102/BMS-986015);

r) Agents targeting the Adenosine receptors or the ectonucleases CD39 and CD73 that convert adenosin triphosphate (ATP) to Adenosine, such as MEDI9447 (anti-CD73 antibody), PBF-509; CPI-444 (Adenosine A2a receptor antagonist);

s) antagonists to chemokine receptors including CCR2 or CCR4;

t) modulators of the complement system v) agents that deplete or inhibit T regulatory cells (e.g., using an anti-CD25 monoclonal antibody (e.g., daclizumab) or by ex vivo anti-CD25 bead depletion) or reverse/prevent T cell anergy or exhaustion.

When used in combination with the compounds of Formula (I), immune checkpoint inhibitors, and especially those targeting the PD-1 receptor or its ligand PD-L1, are preferred.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy. The term "cytotoxic chemotherapy agent" or "chemotherapy agent" as used herein refers to an active anti-neoplastic agent inducing apoptosis or necrotic cell death.

When used in combination with the compounds of Formula (I), the term especially refers to conventional cytotoxic chemotherapy agents such as: 1) alkylating agents (including, without limitation, nitrogen mustards, ethylenimine derivatives, alkyl sulfonates, nitrosoureas and triazenes) such as uracil mustard, mechlorethamine, chlorambucil, cyclophosphamide, ifosfamide, streptozocin, carmustine, lomustine, melphalan, busulfan, procarbazine, dacarbazine, temozolomide, pipobroman, triethylene-melamine, triethylenethiophosphoramine, thiotepa or altretamine; in particular temozolomide); 2) platinum drugs (for example cisplatin, carboplatin or oxaliplatin); 3) antimetabolite drugs (for example 5-fluorouracil, floxuridine, pentostatine, capecitabine, 6-mercaptopurine, methotrexate, gemcitabine, cytarabine, fludarabine or pemetrexed); 4) anti-tumor antibiotics (for example daunorubicin, doxorubicin, epirubicin, idarubicin, actinomycin-D, bleomycin, mitomycin-C or mitoxantrone); 5) mitotic inhibitors (for example paclitaxel, docetaxel, ixabepilone, vinblastine, vincristine, vinorelbine, vindesine or estramustine); or 6) topoisomerase inhibitors (for example etoposide, teniposide, topotecan, irinotecan, diflomotecan or elomotecan). Also suitable are cytotoxic agents such as biological response modifiers; growth inhibitors; antihormonal therapeutic agents; leucovorin; tegafur; and haematopoietic growth factors.

When used in combination with the compounds of Formula (I), preferred cytotoxic chemotherapy agents are the above-mentioned alkylating agents (notably fotemustine, cyclophosphamide, ifosfamide, carmustine, dacarbazine and prodrugs thereof such as especially temozolomide or pharmaceutically acceptable salts of these compounds; in particular temozolomide); mitotic inhibitors (notably paclitaxel, docetaxel, ixabepilone; or pharmaceutically acceptable salts of these compounds; in particular paclitaxel); platinum drugs (notably cisplatin, oxaliplatin and carboplatin); as well etoposide and gemcitabine.

For avoidance of any doubt, if compounds are described as useful for the prevention or treatment of certain diseases, conditions or disorders, such compounds are likewise suitable for use in the preparation of a medicament for the prevention or treatment of said diseases.

The present invention also relates to a method for the prevention or treatment of diseases, conditions or disorders, mentioned hereinabove and/or hereinbelow comprising administering to a subject a pharmaceutically active amount of a compound as described hereinabove or/and hereinbelow either alone or in combination with other pharmacologically active compounds and/or therapies.

In a preferred embodiment of the present invention, the administered amount of a compound of Formula (I) is comprised between 1 mg and 1000 mg per day, particularly between 5 mg and 500 mg per day, more particularly between 25 mg and 400 mg per day, especially between 50 mg and 200 mg per day.

The meaning of the term "prevention" may also be understood as "prophylaxis".

Preparation of Compounds of Formula (I)

A further aspect of the invention is a process for the preparation of compounds of Formula (I). Compounds according to Formula (I) of the present invention can be prepared from commercially available or well-known starting materials according to the methods described in the experimental part; by analogous methods; or according to the general sequence of reactions outlined below. The terms "$R^1$", "$R^2$", "$R^{3a}$", "$R^{3b}$", "$R^4$", "$R^5$" and "Q", as used hereinbelow, can be deduced from the corresponding definitions in Formula (I) or are explicitly/implicitly defined in the text. The term "R" is defined in the schemes hereinbelow. For avoidance of doubt the meaning of said term may differ from the meaning of the term "R" used to designate the substituent of Q in Formula (I). Other abbreviations used herein are explicitly defined or are as defined in the experimental section. The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

General Preparation Routes:

Compounds of Formula (I) can be prepared starting from an intermediate of Formula (A1) (wherein PG represents an amine protecting group such as Boc), which is reacted with N,O-dimethylhydroxylamine hydrochloride under standard conditions (e.g. T3P®, DIPEA, DCM, RT) to give the Weinreb amide derivative of Formula (A2) (Scheme A). Upon reaction with a compound of Formula (A3) wherein X is a halide such as bromine, in presence of n-butyl lithium in THF at a temperature around −78° C., the ketone derivative of Formula (A4) is produced, which can be further reacted with a bromoderivative of Formula (A5), similarly using n-hexyl lithium in THF at a temperature around −78° C., to provide the tertiary alcohol intermediate of Formula (A6). A chiral separation by HPLC or SFC over a chiral stationary phase can be performed at this stage to yield enantiomerically pure intermediates of Formula (A6). Cleavage of the protecting group under standard conditions, such as treatment with HCl in dioxane at temperatures around RT in the case of a Boc protecting group, can provide the free NH derivative of Formula (A7), which depending on substituents $R^4$ and $R^5$ can be a final example of Formula (I). A reductive amination step can be performed with an amine of Formula (A7) and an aldehyde of Formula (A8) or a ketone of Formula (A9) under standard conditions such as using $NaBH(OAc)_3$ or $NaBH_3CN$ as reductive agent, in presence of a base such as DIPEA or TEA, or in presence of an acid such as acetic acid, in a solvent such as DCM, MeOH, THF or dioxane, or a mixture thereof, and at a temperature around RT to provide compounds of Formula (I). Alternatively, the intermediate of Formula (A7) can be alkylated with a reactant of Formula (A10) wherein X is iodine or bromine, in presence of a base such as TEA, DIPEA or $Cs_2CO_3$, in a solvent such as MeOH, THF or DMF, and stirring at a temperature from 0° C. to 70° C. to provide compounds of Formula (I). Furthermore, the compounds of Formula (I) wherein $R^2$ is cyclopropyl can be prepared by coupling with (1-ethoxycyclopropoxy)trimethysilane, using $NaBH_3CN$ in presence AcOH in MeOH and at temperatures around RT.

Scheme A

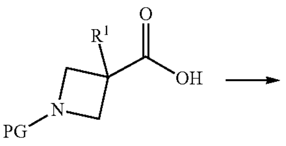

(A1)

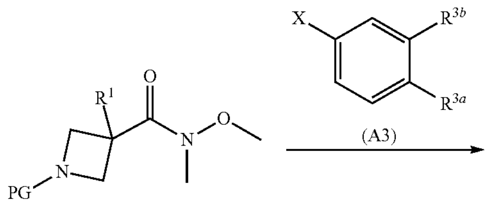

(A2)

-continued

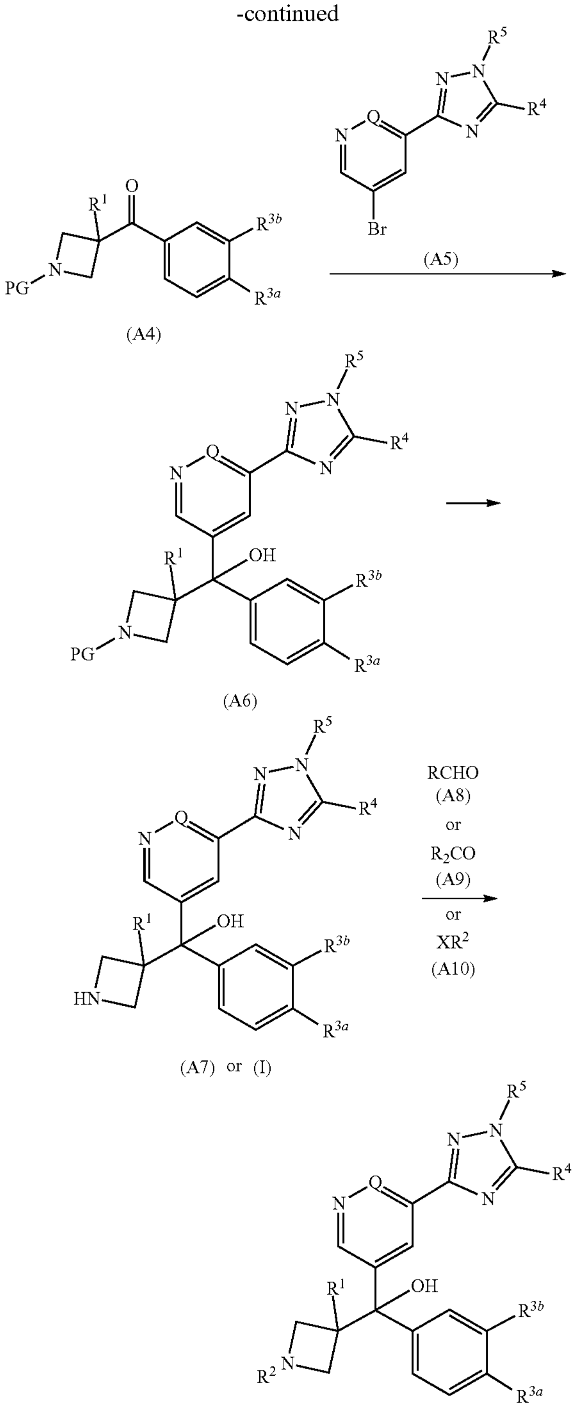

(A4) (A6) (A7) or (I) (I)

Alternatively, compounds of Formula (I) can be prepared according to the procedure described in Scheme B, where a solution of ketone of Formula (A4) and a bromocyanopyridine of Formula (B6) wherein Q is CH, CMe, CF or CCl in a solvent such as THF, can be treated with n-hexyllithium at a temperature around −78° C. The resulting intermediate of Formula (B1) may be transformed to the amidoxime of Formula (B2) by treatment with hydroxylamine in the presence of a base, such as DIPEA or $K_2CO_3$, in solvents such as DMSO or EtOH at temperatures around RT. The amidoxime of Formula (B2) may exist in two tautomeric forms, wherein the substituent of the 6-membered heteroaryl represents —C($NH_2$)═N—OH or —C(═NH)—NH—OH. The amidoxime of Formula (B2) can be converted to the amidine of Formula (B3) in a stepwise procedure involving acetylation using acetic anhydride in acetic acid, followed by hydrogenation (in the presence of Pd/C). Formation of the triazole ring in compounds of Formula (A6) or (I) may be achieved by a 2-step one-pot procedure, where the amidine of Formula (B3) can be coupled to a carboxylic acid of Formula (B4) under standard amide coupling conditions (HATU, DIPEA, DMF), followed by ring formation at elevated temperatures around 80° C. with a hydrazine of Formula (B5). Deprotection and N-alkylation of the azetidine ring according to procedures described in Scheme A can be performed at this or at an earlier stage.

Scheme B

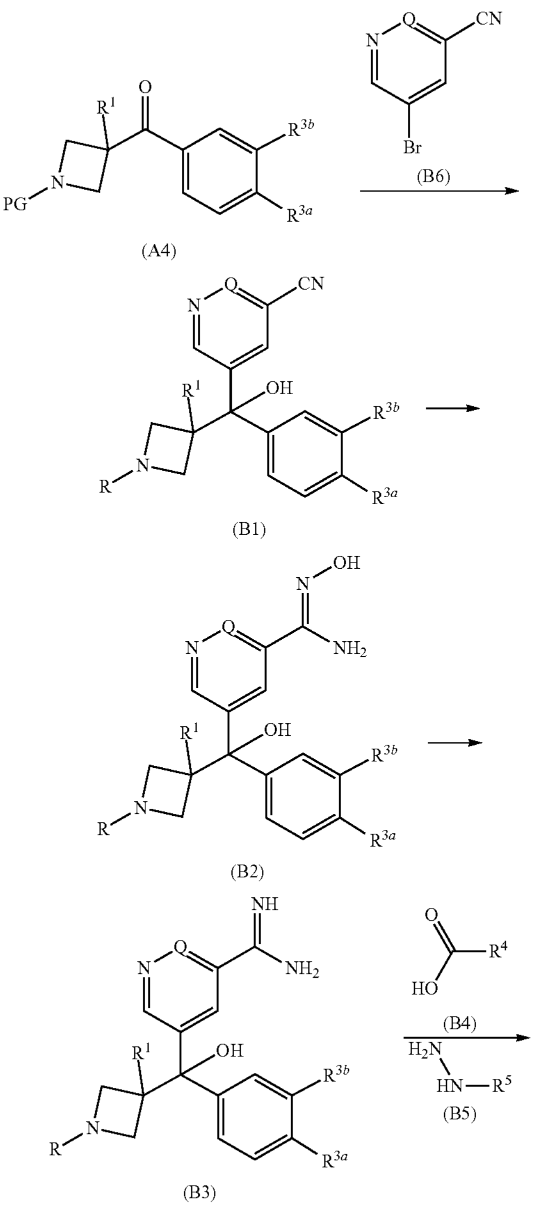

(A4) (B1) (B2) (B3) (B5)

-continued

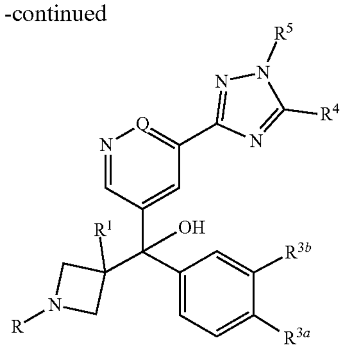

R = PG: (A6)
R = $R^2$: (I)

Another way to access compounds of Formula (I) or intermediates of Formula (A6) wherein $R^{3a}$ represents $C_{1-5}$ alkyl, $C_{1-3}$fluoroalkyl or $C_{3-5}$cycloalkyl, involves the bromophenyl compound of Formula (I) or an intermediate of Formula (A6) wherein $R^{3a}$ represents bromine and $R^{3b}$ represents hydrogen (Scheme C). Under Suzuki conditions (Pd catalyst and base in toluene/water) it can be coupled to a boron species of Formula (C1) wherein BX represents $BF_3K$, Bpin or $B(OH)_2$ and $R^{3a}$ represents $C_{1-5}$alkyl, $C_{1-3}$fluoroalkyl or $C_{3-5}$cycloalkyl to yield a compound of Formula (I) or intermediate of Formula (A6) wherein in both species $R^{3a}$ represents $C_{1-5}$ alkyl, $C_{1-3}$fluoroalkyl or $C_{3-5}$cycloalkyl and $R^{3b}$ represents hydrogen.

Scheme C

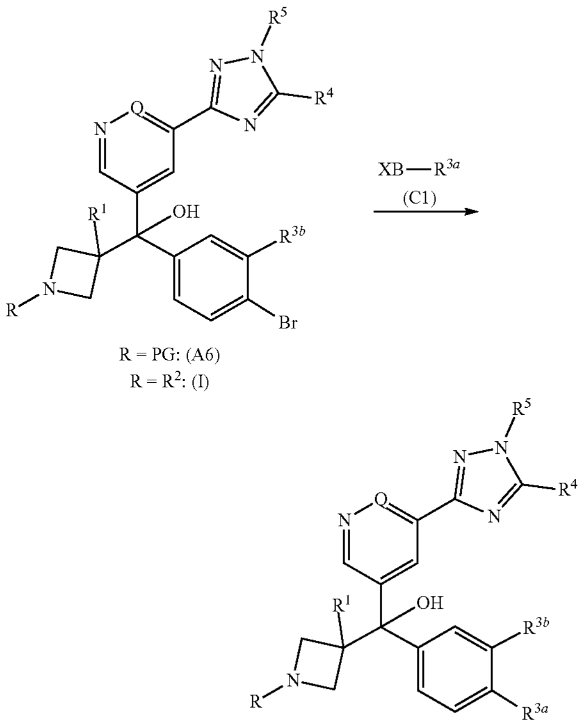

R = PG: (A6)
R = $R^2$: (I)

R = PG: (A6)
R = $R^2$: (I)

The bromopyridine building blocks of Formula (A5) can be synthesized according to the procedure depicted in Scheme D. Their production requires the triazole ring formation already described in the context of Scheme B, starting from an amidine of Formula (D1).

Scheme D

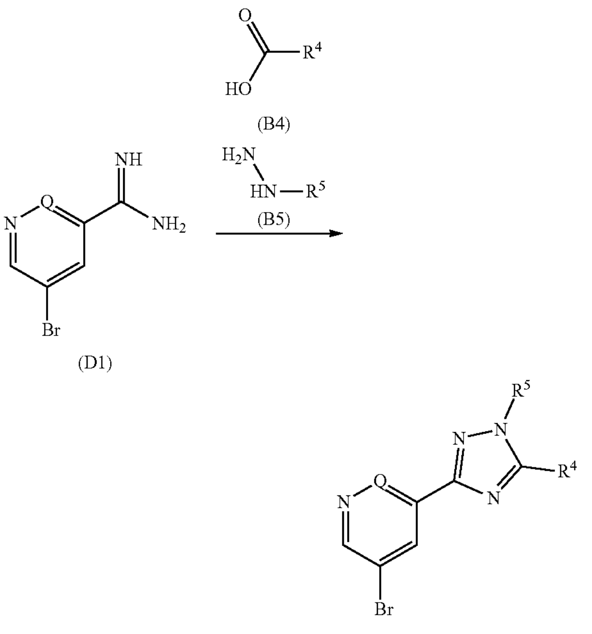

(B4)
(B5)
(D1)
(A5)

Reactants of Formula (A1), (A3), (A8), (A9), (A10), (B4), (B5), (B6), (C1), (D1) are either commercially available or can be synthesized according to published protocols.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase. Enantiomeric separation may be performed with compounds of Formula (I), or at an earlier stage.

Depending on the purification conditions, intermediates and compounds of Formula (I) may be isolated as free bases or as salts such as formate salts, or hydrochloride salts. Methods known to one skilled in the art may be applied to isolate free forms if applicable.

EXPERIMENTAL SECTION

Abbreviations (as Used Herein and in the Description Above)

Ac acetyl
anal analytical
anh anhydrous
aq aqueous
Boc tert.-butyloxycarbonyl
Bu n-butyl
BSA bovine serum albumin
cataCXium©A Pd G3 mesylate[(di(1-adamantyl)-n-butylphosphine)-2-(2'-amino-1,1'-biphenyl)]palladium (II)
CC column chromatography
CV column volume(s)
dba dibenzylideneacetone DCM dichloromethane
DEA diethylamine
DIPEA N,N-diisopropylethylamine
DMF N,N-dimethylformamide
DMSO dimethylsulfoxide
dppf 1,1'-bis(diphenylphosphino)ferrocene
EA ethyl acetate
Et ethyl
FLIPR fluorescent imaging plate reader
Fluo-8-AM acetyloxymethyl 2-[N-[2-(acetyloxymethoxy)-2-oxoethyl]-4-[3-(acetyloxymethoxy)-6-oxoxanthen-9-yl]-2-[2-[2-[bis[2-(acetyloxymethoxy)-2-oxoethyl]amino]phenoxy]ethoxy]anilino]acetate
eq equivalent
g gram(s)
HATU (1-[bis(dimethylamino)methylene]-1H-1,2,3-triazolo[4,5-b]pyridinium 3-oxide hexafluorophosphate
HEK human embryonic kidney
Hex n-hexyl
h hour(s)
Hep heptane
iPr isopropyl
HPLC high performance liquid chromatography
LC-MS liquid chromatography mass spectrometry
[M] molecular mass
M molarity [mol/$L^{-1}$]
Me methyl
mg milligram(s)
min minute(s)
mL millilitre
org organic
Pd/C palladium on carbon
PG protecting group
pin pinacol
prep preparative
RT room temperature
rxn reaction
sat saturated
SFC supercritical fluid chromatography
soln solution
t time
T3P® propanephosphonic acid anhydride
TEA triethylamine
$t_R$ retention time
THF tetrahydrofuran I. Chemistry The following Examples illustrate the preparation of biologically active compounds of the invention but do not at all limit the scope thereof.

General: All temperatures are stated in degrees Celsius (° C.). Unless otherwise indicated, the reactions take place at RT under an argon atmosphere and are run in a flame dried (for water.sensitive rxn) round-bottomed flask or sealable tube equipped with a magnetic stir bar.

Characterization Methods Used:

The LC-MS retention times have been obtained using the following elution conditions:

I) LC-MS (A):

Zorbax RRHD SB-Aq, 1.8 m, 2.1×50 mm column thermostated at 40° C. The two elution solvents were as follows: solvent A=water+0.04% TFA; solvent B=MeCN. The eluent flow rate was 0.8 mL/min and the characteristics of the eluting mixture proportion in function of the time t from start of the elution are summarized in the table below (a linear gradient being used between two consecutive time points):

| t (min) | 0 | 1.2 | 1.9 | 2.1 |
|---|---|---|---|---|
| Solvent A (%) | 95 | 5 | 5 | 95 |
| Solvent B (%) | 5 | 95 | 95 | 5 |

The chiral HPLC/SFC retention times have been obtained using the following elution conditions:

1) Chiral SFC (A):

CHIRALCEL OD-H, 5 μm, 4.6×250 mm column thermostated at 40° C. was used. The two elution solvents were as follows: solvent A=$CO_2$; solvent B=MeOH. The eluent flow rate was 4 mL/min, the isocratic solvent proportion was 90% (A)/10% (B).

II) Chiral SFC (B):

CHIRALPAK ID, 5 m, 4.6×250 mm column thermostated at 40° C. was used. The two elution solvents were as follows: solvent A=$CO_2$; solvent B=MeCN/EtOH/DEA 50/50/0.1. The eluent flow rate was 4 mL/min, the isocratic solvent proportion was 65% (A)/35% (B).

III) Chiral SFC (C):

Chiralcel OD-D, 5 m, 4.6×250 mm column thermostated at 40° C. was used. The two elution solvents were as follows: solvent A=$CO_2$; solvent B=MeCN/EtOH/1/1. The eluent flow rate was 4 mL/min, the isocratic solvent proportion was 70% (A)/30% (B).

IV) Chiral SFC (D):

ChiralCel OD-H, 5 m, 4.6×250 mm column thermostated at 40° C. was used. The two elution solvents were as follows: solvent A=$CO_2$; solvent B=MeCN/EtOH/DEA 50/50/0.1. The eluent flow rate was 4 mL/min, the isocratic solvent proportion was 65% (A)/35% (B).

V) Chiral SFC (E):

ChiralCel OD-H, 5 m, 4.6×250 mm column thermostated at 40° C. was used. The two elution solvents were as follows: solvent A=$CO_2$; solvent B=MeCN/EtOH/DEA 50/50/0.1. The eluent flow rate was 4 mL/min, the isocratic solvent proportion was 75% (A)/25% (B).

VI) Chiral SFC (F):

ChiralPak ID, 5 m, 4.6×250 mm column thermostated at 40° C. was used. The two elution solvents were as follows: solvent A=$CO_2$; solvent B=MeCN/EtOH/DEA 50/50/0.1. The eluent flow rate was 4 mL/min, the isocratic solvent proportion was 65% (A)/35% (B).

VII) Chiral SFC (G):

CHIRALCEL OJ-H, 5 m, 4.6×250 mm column thermostated at 40° C. was used. The two elution solvents were as follows: solvent A=$CO_2$; solvent B=MeOH. The eluent flow rate was 4 mL/min, the isocratic solvent proportion was 95% (A)/5% (B).

VIII) Chiral SFC (H):

CHIRALPAK IH, 5 m, 4.6×250 mm column thermostated at 40° C. was used. The two elution solvents were as follows: solvent A=$CO_2$; solvent B=MeCN+EtOH 1/1. The eluent flow rate was 4 mL/min, the duration of the run was 5 min and the isocratic solvent proportion was 85% (A)/15% (B).

Purification Methods Used:

Preparative LC-MS Methods Used:

The purifications by preparative LC-MS have been performed using the conditions described hereafter.

I) Prep LC-MS (I):

A Zorbax column (SB-AQ, 7 μm OBD, 50×150 mm) was used. The two elution solvents were as follows: solvent A=MeCN; solvent B=water+0.5% Formic acid (25%). The characteristics of the eluting mixture proportion in function of the time t from start of the elution are summarized in the tables below (a linear gradient being used between two consecutive time points):

| t (min) | 0 | 0.3 | 0.8 | 7.5 | 7.7 | 9.5 | 10.0 | 11.5 | 12.0 |
|---|---|---|---|---|---|---|---|---|---|
| Flow (mL/min) | 75 | 75 | 150 | 150 | 150 | 150 | 150 | 150 | 75 |
| Solvent A (%) | 40 | 40 | 40 | 75 | 95 | 95 | 40 | 40 | 40 |
| Solvent B (%) | 60 | 60 | 60 | 25 | 5 | 5 | 60 | 60 | 60 |

II) Prep LC-MS (II):

X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3.5 | 6.0 | 6.2 | 6.6 |
|---|---|---|---|---|---|---|
| Solvent A (%) | 70 | 70 | 5 | 5 | 70 | 70 |
| Solvent B (%) | 30 | 30 | 95 | 95 | 30 | 30 |

III) Prep LC-MS (III)

A X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 80 | 80 | 5 | 5 | 80 | 80 |
| Solvent B (%) | 20 | 20 | 95 | 95 | 20 | 20 |

IV) Prep LC-MS (IV)

A X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

V) Prep LC-MS (V):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

VI) Prep LC-MS (VI):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3 | 4.0 | 6.0 | 6.2 | 6.6 |
|---|---|---|---|---|---|---|---|
| Solvent A (%) | 95 | 95 | 50 | 5 | 5 | 95 | 95 |
| Solvent B (%) | 5 | 5 | 50 | 95 | 95 | 5 | 5 |

VII) Prep LC-MS (VHI):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 80 | 80 | 5 | 5 | 80 | 80 |
| Solvent B (%) | 20 | 20 | 95 | 95 | 20 | 20 |

VIII) Prep LC-MS (VIII):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3.5 | 6.0 | 6.2 | 6.6 |
|---|---|---|---|---|---|---|
| Solvent A (%) | 70 | 70 | 5 | 5 | 70 | 70 |
| Solvent B (%) | 30 | 30 | 95 | 95 | 30 | 30 |

IX) Prep LC-MS (IX):

A X-Bridge column (Waters C18, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

X) Prep LC-MS (X):

An X-Bridge column (Waters C18, 10 μm OBD, 30×75 mm) was used. The two elution solvents were as follows:

solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 80 | 80 | 5 | 5 | 80 | 80 |
| Solvent B (%) | 20 | 20 | 95 | 95 | 20 | 20 |

Preparative Chiral SFC and HPLC Methods Used:

The purifications by preparative chiral SFC and HPLC have been performed using the conditions described hereafter.

I) Prep Chiral SFC (I):

A ChiralCel OD-H (Sm, 30×250 mm) column thermostated at 40° C. was used. The elution solvent was $CO_2$/MeOH 90/10, run at a flow rate of 160 mL/min.

II) Prep Chiral SFC (II):

A ChiralPak ID (Sm, 30×250 mm) column thermostated at 40° C. was used. The elution solvent was $CO_2$/MeCN:EtOH:DEA 80:80:0.1 80/20 at a flow rate of 160 mL/min.

III) Prep Chiral SFC (III):

A ChiralCel OD-H (5 m, 30×250 mm) column thermostated at 40° C. was used. The elution solvent was $CO_2$/MeCN:EtOH 1:1 70/30 at a flow rate of 160 mL/min.

IV) Prep Chiral SFC (IV):

A ChiralCel OD-H (5 m, 30×250 mm) column thermostated at 40° C. was used. The elution solvent was $CO_2$/(MeCN:EtOH:DEA 50:50:0.1) 65/35 at a flow rate of 160 mL/min.

V) Prep Chiral SFC (V):

A ChiralCel OD-H (5 m, 30×250 mm) column thermostated at 40° C. was used. The elution solvent was $CO_2$/(MeCN:EtOH:DEA 50:50:0.1) 75/25 at a flow rate of 160 mL/min.

VI) Prep Chiral SFC (VI):

A ChiralPak ID (5 m, 30×250 mm) column thermostated at 40° C. was used. The elution solvent was $CO_2$/(MeCN:EtOH:DEA 50:50:0.1) 65/35 at a flow rate of 160 mL/min.

VII) Prep Chiral SFC (VII):

A ChiralCel OJ-H (5 m, 30×250 mm) column thermostated at 40° C. was used. The elution solvent was $CO_2$/MeOH 95/5 at a flow rate of 160 mL/min.

VIII) Prep Chiral SFC (VIII):

A (R,R) Whelk-01 (Sm, 30×250 mm) column thermostated at 40° C. was used. The elution solvent was $CO_2$/(MeCN:EtOH:DEA 50:50:0.1) 60/40 at a flow rate of 160 mL/min.

IX) Prep Chiral SFC (IX):

A ChiralPak IH (Sm, 30×250 mm) column thermostated at 40° C. was used. The elution solvent was $CO_2$/50% MeCN-50% EtOH 85/15, run for 6 min and at a flow rate of 160 mL/min.

Preparation of Intermediate of Formula A2

A2.1 3-(Methoxy-methyl-carbamoyl)-3-methyl-azetidine-1-carboxylic acid tert-butyl ester To a solution of 1-Boc-3-methylazetidine carboxylic acid (20 g) in DCM (500 mL) were added N,O-dimethylhydroxylamine hydrochloride (8.97 g), DIPEA (54 mL) and T3P® in DCM 1.72M (68 mL) under cooling with a water bath at RT. The resulting solution was stirred at RT for 2 h30 before it was quenched with aq. sat. $NaHCO_3$. The phases were separated, and the org. layer was washed with citric acid (10%) and water. Afterwards the aq. layers were re-extracted with 1×DCM. The combined org. layers were dried over $MgSO_4$, filtrated off, concentrated in vacuo and dried under HV to give 24.9 g of the title compound as brown oil. LC-MS (A): $t_R$=0.78 min; $[M+H]^+$: 259.29

Preparation of Intermediates of Formula A4

To a soln of bromide A3 (1.3 eq) in anh THF (1.6 to 2.6 mL/mmol) under argon and cooled to −78° C. was added dropwise BuLi (2.5 M in hexane, 1.2 eq) while maintaining the internal temperature below −70° C. (except for the preparation of Intermediate A4.6 where BuLi was replaced by HexLi). The resulting mixture was stirred at −78° C. for 30 min. A soln of Weinreb amide A2 (1 eq) in anh THF (0.9 to 1.1 mL/mmol) was added dropwise while keeping the internal temperature below −70° C. The resulting soln was allowed to warm to RT and was stirred until completion of the rxn. The rxn mixture was quenched with water and extracted with DCM. The combined org. phases were washed with brine, dried over $MgSO_4$ and evaporated to dryness. The resulting crude material was purified by CC using Sfär Silica D or Snap KP-SIL prepacked cartridges from Biotage® and eluting with Hep/EA.

| A4 | Name | Reactant A3 | $t_R$ [min] | MS-data m/z $[M + H]^+$ |
|---|---|---|---|---|
| A4.1 | 3-(4-Bromo-benzoyl)-3-methyl-azetidine-1-carboxylic acid tert-butyl ester | 1,4-Dibromo benzene | 1.07 | 355.88 |
| A4.2 | 3-(4-tert-Butyl-benzoyl)-3-methyl-azetidine-1-carboxylic acid tert-butyl ester | 1-Bromo-4-tert-butylbenzene | 1.11 | 332.27 |
| A4.3 | 3-Methyl-3-[4-(1-trifluoromethyl-cyclopropyl)-benzoyl]-azetidine-1-carboxylic acid tert-butyl ester | 1-Bromo-4-(1-trifluoromethyl-cyclopropyl)-benzene | 1.10 | 384.28 |
| A4.4 | 3-(4-Isopropyl-benzoyl)-3-methyl-azetidine-1-carboxylic acid tert-butyl ester | 1-Bromo-4-isopropylbenzene | 1.09 | 318.31 |
| A4.5 | 3-Methyl-3-(4-trifluoromethoxy-benzoyl)-azetidine-1-carboxylic acid tert-butyl ester | 1-Bromo-4-(trifluoromethoxy)benzene | 1.07 | 360.19 |
| A4.6 | 3-(4-Cyclopropyl-benzoyl)-3-methyl-azetidine-1-carboxylic acid tert-butyl ester | 1-Bromo-4-cyclopropylbenzene | 1.06 | 316.17 |
| A4.7 | 3-(3-Fluoro-4-isopropyl-benzoyl)-3-methyl-azetidine-1-carboxylic acid tert-butyl ester | 4-Bromo-2-fluoro-1-isopropylbenzene | 1.12 | 321.09 |

Preparation of Intermediates of Formula A5

A5.1 3-Bromo-5-[1-cyclopropyl-5-(tetrahydro-pyran-4-yl)-1H-[1,2,4]triazol-3-yl]-pyridine DMF (40.2 mL) and DIPEA (4.61 mL) were added to 5-bromopyridine-3-carboximidamide hydrochloride (2 g), tetrahydropyran-4-carboxylic acid (1387 mg) and HATU (3.36 g). The solution was stirred overnight at RT. Then cyclopropylhydrazine hydrochloride (1.38 g) and then AcOH (4.61 mL) were added and the mixture was stirred at 80° C. Then the mixture was diluted with EA, washed with aq. sat. $NaHCO_3$ and then water and brine. The combined org. phase was dried over $MgSO_4$, filtrated, concentrated in vacuo and purified by CC (Biotage®, 110 g sphere amino, A: Hep, B: EA; gradient (in % B); 12-50 over 4.3 CV) to afford 1.88 g of the title compound as white solid. LC-MS (A): $t_R$=0.89 mN; [M+H]A: 350.94

Preparation of Intermediates of Formula A6

To a soln of ketone A4 (1 eq) and bromide A.1 (1.0 to 1.1 eq) in anh THF (3.4 to 9 mL/mmol) under argon and cooled to −78° C. was added dropwise HexLi (2.3 M in hexane, 1.05 to 1.3 eq) while maintaining the internal temperature below −70 mC. The resulting soln was stirred below −70° C. until completion ofthe rxn, quenched with water and extracted with EA. The combined org. phases were washed with brine, dried over $MgSO_4$ and concentrated in vacuo. The resulting crude was purified using Sfär KP-Amino or Snap KP-SIL prepacked cartridges from Biotage® and eluting with Hep/EA (A6.1-A6.3) or DCM/MeOH (A6.15). When necessary an additional purification by prep. LC-MS using method Ill was performed. A6.16 was additionally purified by prep. chiral SEC (III) (chiral SEC (C): $t_R$=2.43 min, second eluting isomer). A6.25 was purified by prep. LC-MS method X.

| A6 | Name | Reactant A4 | $t_R$ [min] | MS-data m/z [M + H]$^+$ |
|---|---|---|---|---|
| A6.1 | 3-((4-Bromo-phenyl)-{5-[1-cyclopropyl-5-(tetrahydro-pyran-4-yl)-1H-[1,2,4]triazol-3-yl]-pyridin-3-yl}-hydroxy-methyl)-3-methyl-azetidine-1-carboxylic acid tert-butyl ester | A4.1 | 0.97 | 625.87 |
| A6.2 | 3-((4-tert-Butyl-phenyl)-{5-[1-cyclopropyl-5-(tetrahydro-pyran-4-yl)-1H-[1,2,4]triazol-3-yl]-pyridin-3-yl}-hydroxy-methyl)-3-methyl-azetidine-1-carboxylic acid tert-butyl ester | A4.2 | 1.02 | 602.20 |
| A6.3 | 3-{{5-[1-Cyclopropyl-5-(tetrahydro-pyran-4-yl)-1H-[1,2,4]triazol-3-yl]-pyridin-3-yl}-hydroxy-[4-(1-trifluoromethyl-cyclopropyl)-phenyl]-methyl}-3-methyl-azetidine-1-carboxylic acid tert-butyl ester | A4.3 | 1.02 | 654.15 |
| A6.15 | 3-[{5-[1-Cyclopropyl-5-(tetrahydro-pyran-4-yl)-1H-[1,2,4]triazol-3-yl]-pyridin-3-yl}-hydroxy-(4-trifluoromethoxy-phenyl)-methyl]-3-methyl-azetidine-1-carboxylic acid tert-butyl ester | A4.5 | 1.00 | 630.12 |
| A6.16 | 3-((R)-(4-Cyclopropyl-phenyl)-{5-[1-cyclopropyl-5-(tetrahydro-pyran-4-yl)-1H-[1,2,4]triazol-3-yl]-pyridin-3-yl}-hydroxy-methyl)-3-methyl-azetidine-1-carboxylic acid tert-butyl ester | A4.6 | 0.96 | 586.17 |
| A6.25 | 3-[{5-[1-Cyclopropyl-5-(tetrahydro-pyran-4-yl)-1H-[1,2,4]triazol-3-yl]-pyridin-3-yl}-(3-fluoro-4-isopropyl-phenyl)-hydroxy-methyl]-3-methyl-azetidine-1-carboxylic acid tert-butyl ester | A4.7 | 1.02 | 606.17 |

To a mixture of Intermediate B3.1 (1 eq.), carboxylic acid (1.2 eq.), molecular sieves (3 A, 450 mg/mmol B3.1) and HATU (1.2 eq.) in DMF (4 mL/mmol B3.1) was added DIPEA (4 eq.). After stirring at RT for 2.5 h, a premixed solution of carboxylic acid (1.2 eq.) and HATU (1.2 eq.) in DMF (2 mL/mmol B3.1) were added and the mixture was stirred for another hour, until the formation of the intermediate was complete. To the mixture was then added the substituted hydrazine (1.5 eq.) and AcOH (10 eq.). The reaction was stirred at 85° C. for 1 h or until complete conversion of intermediate. After cooling to RT, the mixture was diluted with EA, washed with sat. aq. $NaHCO_3$ and brine, dried over $Na_2SO_4$, filtered and concentrated under vacuum. The residue was purified by prep. LC-MS using the conditions listed in the table below.

| A6 | Name | carboxylic acid | hydrazine | $t_R$ [min] | MS-data m/z [M + H]$^+$ | prep LC-MS |
|---|---|---|---|---|---|---|
| A6.4 | 3-[(R)-{5-[1-Cyclopropyl-5-(tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | tetrahydropyran-4-carboxylic acid | cyclopropylhydrazine hydrochloride | 0.99 | 588.39 | (VII) |

-continued

| A6 | Name | carboxylic acid | hydrazine | $t_R$ [min] | MS-data m/z $[M + H]^+$ | prep LC-MS |
|---|---|---|---|---|---|---|
| A6.5 | 3-[(R)-{5-[1-Cyclohexyl-5-(tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | tetrahydropyran-4-carboxylic acid | cyclohexylhydrazine hydrochloride | 1.06 | 630.36 | (VIII) |
| A6.6 | 3-((R)-Hydroxy-(4-isopropyl-phenyl)-{5-[1-methyl-5-(tetrahydro-pyran-4-yl)-1H-[1,2,4]triazol-3-yl]-pyridin-3-yl}-methyl)-3-methyl-azetidine-1-carboxylic acid tert-butyl ester | tetrahydropyran-4-carboxylic acid | methylhydrazine | 0.95 | 562.38 | (VII) + (III) |
| A6.7 | 3-[(R)-Hydroxy-{5-[1-(2-hydroxy-ethyl)-5-(tetrahydro-pyran-4-yl)-1H-[1,2,4]triazol-3-yl]-pyridin-3-yl}-(4-isopropyl-phenyl)-methyl]-3-methyl-azetidine-1-carboxylic acid tert-butyl ester | tetrahydropyran-4-carboxylic acid | 2-hydroxyethylhaydrazine | 0.88 | 592.34 | (III) |
| A6.8 | 3-[(R)-{5-[1-Ethyl-5-(tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | tetrahydropyran-4-carboxylic acid | 1-ethylhydrazine hydrochloride | 0.98 | 576.36 | (III) |
| A6.9 | 3-((R)-Hydroxy-(4-isopropyl-phenyl)-{5-[1-isopropyl-5-(tetrahydro-pyran-4-yl)-1H-[1,2,4]triazol-3-yl]-pyridin-3-yl}-methyl)-3-methyl-azetidine-1-carboxylic acid tert-butyl ester | tetrahydropyran-4-carboxylic acid | isopropylhydrazine hydrochloride | 1.01 | 590.36 | (VII) |
| A6.10 | 3-[(R)-{5-[1-Cyclopentyl-5-(tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | tetrahydropyran-4-carboxylic acid | cyclopentylhydrazine hydrochloride | 1.06 | 616.39 | (VIII) |
| A6.11 | 3-[(R)-{5-[1-tert-Butyl-5-(tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | tetrahydropyran-4-carboxylic acid | tert-butylhydrazine hydrochloride | 1.04 | 604.36 | (VII) |
| A6.12 | 3-[(R)-{5-[1-(2,2-Difluoro-propyl)-5-(tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | tetrahydropyran-4-carboxylic acid | (2,2-difluoropropyl) hydrazine hydrochloride | 1.02 | 626.28 | (VII) |
| A6.13 | 3-[(R)-{5-[1-Cyclobutyl-5-(tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | tetrahydropyran-4-carboxylic acid | cyclobutylhydrazine dihydrochloride | 1.04 | 602.35 | (VIII) |
| A6.14 | 3-[(R)-[5-(1-Cyclopropyl-5-pyridin-3-yl-1H-[1,2,4]triazol-3-yl)-pyridin-3-yl]-hydroxy-(4-isopropyl-phenyl)-methyl]-3-methyl-azetidine-1-carboxylic acid tert-butyl ester | nicotinic acid | cyclopropylhydrazine hydrochloride | 1.04 | 582.23 | (VII) |
| A6.17 | 3-[(R)-{5-[1-Cyclopropyl-5-(1-hydroxy-1-methyl-ethyl)-1H-[1,2,4]triazol-3-yl]-pyridin-3-yl}-hydroxy-(4-isopropyl-phenyl)-methyl]-3-methyl-azetidine-1-carboxylic acid tert-butyl ester | alpha-hydroxyisobutyric acid | cyclopropylhydrazine hydrochloride | 0.97 | 562.27 | (VII) |
| A6.18 | 3-[(R)-Hydroxy-{5-[5-(1-hydroxy-1-methyl-ethyl)-1-isopropyl-1H-[1,2,4]triazol-3-yl]-pyridin-3-yl}-(4-isopropyl-phenyl)-methyl]-3-methyl-azetidine-1-carboxylic acid tert-butyl ester | alpha-hydroxyisobutyric acid | isopropylhydrazine hydrochloride | 0.98 | 564.36 | (VII) |
| A6.19 | 3-[(R)-{5-[1-Cyclopropyl-5-(3-hydroxymethyl-bicyclo[1.1.1]pent-1-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | B4.1 | cyclopropylhydrazine hydrochloride | 0.96 | 600.18 | (VII) |
| A6.20 | 3-[(R)-Hydroxy-{5-[5-(3-hydroxymethyl-bicyclo[1.1.1]pent-1-yl)-1-isopropyl-1H-[1,2,4]triazol-3-yl]-pyridin-3-yl}-(4-isopropyl-phenyl)-methyl]-3-methyl-azetidine-1-carboxylic acid tert-butyl ester | B4.1 | isopropylhydrazine hydrochloride | 0.96 | 602.35 | (VII) |

-continued

| A6 | Name | carboxylic acid | hydrazine | $t_R$ [min] | MS-data m/z $[M + H]^+$ | prep LC-MS |
|---|---|---|---|---|---|---|
| A6.21 | 3-[(R)-{5-[1-Cyclopropyl-5-(4-hydroxy-tetrahydro-pyran-4-yl)-1H-[1,2,4]triazol-3-yl]-pyridin-3-yl}-hydroxy-(4-isopropyl-phenyl)-methyl]-3-methyl-azetidine-1-carboxylic acid tert-butyl ester | 4-hydroxy tetrahydro-2H-pyran-4-carboxylic acid | cyclopropylhydrazine hydrochloride | 0.95 | 604.34 | (VII) |
| A6.22 | 3-[(R)-Hydroxy-{5-[5-(4-hydroxy-tetrahydro-pyran-4-yl)-1-isopropyl-1H-[1,2,4]triazol-3-yl]-pyridin-3-yl}-(4-isopropyl-phenyl)-methyl]-3-methyl-azetidine-1-carboxylic acid tert-butyl ester | 4-hydroxy tetrahydro-2H-pyran-4-carboxylic acid | isopropylhydrazine hydrochloride | 0.95 | 606.33 | (VII) |
| A6.23 | 3-[(R)-{5-[5-(1-Acetyl-piperidin-4-yl)-1-cyclopropyl-1H-[1,2,4]triazol-3-yl]-pyridin-3-yl}-hydroxy-(4-isopropyl-phenyl)-methyl]-3-methyl-azetidine-1-carboxylic acid tert-butyl ester | 1-acetyl piperidine-4-carboxylic acid | cyclopropylhydrazine hydrochloride | 0.98 | 629.35 | (VII) |
| A6.24 | 3-[(R)-{5-[5-(1-Acetyl-piperidin-4-yl)-1-isopropyl-1H-[1,2,4]triazol-3-yl]-pyridin-3-yl}-hydroxy-(4-isopropyl-phenyl)-methyl]-3-methyl-azetidine-1-carboxylic acid tert-butyl ester | 1-acetyl piperidine-4-carboxylic acid | Isopropylhydrazine hydrochloride | 0.99 | 631.19 | (VII) |
| A6.28 | 3-(R)-Hydroxy-(4-isopropyl-phenyl)-{5-[1-(2-methoxy-ethyl)-5-(tetrahydro-pyran-4-yl)-1H-[1,2,4]triazol-3-yl]-pyridin-3-yl}-methyl)-3-methyl-azetidine-1-carboxylic acid tert-butyl ester | tetrahydropyran-4-carboxylic acid | (2-methoxyethyl) hydrazine hydrochloride | 0.98 | 606.36 | (III) |

To a mixture of the corresponding Intermediate B3 (1 eq.), carboxylic acid (1.2 eq.), molecular sieves (3 A, 450 mg/mmol B3.1) and HATU (1.2 eq.) in DMF (4 mL/mmol B33) was added DIPEA (4 eq.). After stirring at RT for 1 h and in case of incomplete conversion of starting material, a premixed solution of carboxylic acid (1.2 eq.) and HATU (1.2 eq.) in DMF (2 mL/mmol B33) were added and the mixture was stirred for another hour, until the formation of the intermediate was complete. To the mixture was then added the substituted hydrazine (1.5 eq.) and AcOH (10 eq.). The reaction was stirred at 85° C. for 1 h or until complete conversion of intermediate. After cooling to RT, the mixture was diluted with EA, washed with sat. aq. $NaHCO_3$ and brine, dried over $Na_2SO_4$, filtered and concentrated under vacuum. The residue was purified by prep. LC-MS using the conditions listed in the table below.

| A6 | Name | B3 | Carboxylic acid | hydrazine | $t_R$ [min] | MS-data m/z $[M + H]^+$ | prep LC-MS |
|---|---|---|---|---|---|---|---|
| A6.26 | 3-[(R)-{5-[1-Cyclopropyl-5-(trans-4-hydroxy-cyclohexyl)-1H-[1,2,4]triazol-3-yl]-6-fluoro-pyridin-3-yl}-hydroxy-(4-isopropyl-phenyl)-methyl]-3-methyl-azetidine-1-carboxylic acid tert-butyl ester | B3.3 | Trans-4-hydroxycyclo-hexanecarboxylic acid | Cyclopropylhydrazine hydrochloride | 1.05 | 620.46 | (VII) |
| A6.27 | 3-[(R)-{5-[1-Cyclopropyl-5-(trans-4-hydroxy-cyclohexyl)-1H-[1,2,4]triazol-3-yl]-6-methyl-pyridin-3-yl}-hydroxy-(4-isopropyl-phenyl)-methyl]-3-methyl-azetidine-1-carboxylic acid tert-butyl ester | B3.4 | Trans-4-hydroxycyclo-hexanecarboxylic acid | Cyclopropylhydrazine hydrochloride | 0.89 | 616.49 | (V) + (VI) |
| A6.29 | 3-((R)-Hydroxy-(4-isopropyl-phenyl)-{6-[1-isopropyl-5-(tetrahydro-pyran-4-yl)-1H-[1,2,4]triazol-3-yl]-pyridazin-4-yl}-methyl)-3-methyl-azetidine-1-carboxylic acid tert-butyl ester | B3.5 | tetrahydropyran-4-carboxylic acid | Isopropylhydrazine hydrochloride | 1.04 | 591.36 | CC |

Preparation of Intermediates of Formula A7

To a soln of Intermediate A6 (1 eq) in dioxane (4 to 5 mL/mmol) was added HCl (4M in dioxane, 8 eq). The rxn mixture was stirred at RT for 1 to 2 h and evaporated to dryness to give the crude hydrochloride salt. The reaction mixtures of A7.28 and A7.29 were not evaporated to dryness but neutralized to pH 8-10 by addition of aq. sat. $NaHCO_3$ and 1N NaOH, respectively, followed by extraction with DCM. The combined org. layers were evaporated and dried at HV.

| A7 | Name | Reactant A6 | $t_R$ [min] | MS-data m/z [M + H]$^+$ |
|---|---|---|---|---|
| A7.1 | (4-Bromo-phenyl)-{5-[1-cyclopropyl-5-(tetrahydro-pyran-4-yl)-1H-[1,2,4]triazol-3-yl]-pyridin-3-yl}-(3-methyl-azetidin-3-yl)-methanol | A6.1 | 0.68 | 523.98 |
| A7.2 | (4-tert-Butyl-phenyl)-{5-[1-cyclopropyl-5-(tetrahydro-pyran-4-yl)-1H-[1,2,4]triazol-3-yl]-pyridin-3-yl}-(3-methyl-azetidin-3-yl)-methanol | A6.2 | 0.74 | 502.14 |
| A7.3 | {5-[1-Cyclopropyl-5-(tetrahydro-pyran-4-yl)-1H-[1,2,4]triazol-3-yl]-pyridin-3-yl}-(3-methyl-azetidin-3-yl)-[4-(1-trifluoromethyl-cyclopropyl)-phenyl]-methanol | A6.3 | 0.74 | 554.08 |
| A7.4 | (R)-{5-[1-Cyclopropyl-5-(tetrahydro-pyran-4-yl)-1H-[1,2,4]triazol-3-yl]-pyridin-3-yl}-(4-isopropyl-phenyl)-(3-methyl-azetidin-3-yl)-methanol | A6.4 | 0.70 | 488.38 |
| A7.5 | (R)-{5-[1-Cyclohexyl-5-(tetrahydro-pyran-4-yl)-1H-[1,2,4]triazol-3-yl]-pyridin-3-yl}-(4-isopropyl-phenyl)-(3-methyl-azetidin-3-yl)-methanol | A6.5 | 0.78 | 530.42 |
| A7.6 | (R)-(4-Isopropyl-phenyl)-(3-methyl-azetidin-3-yl)-{5-[1-methyl-5-(tetrahydro-pyran-4-yl)-1H-[1,2,4]triazol-3-yl]-pyridin-3-yl}-methanol | A6.6 | 0.66 | 462.36 |
| A7.7 | 2-[3-{5-[(R)-Hydroxy-(4-isopropyl-phenyl)-(3-methyl-azetidin-3-yl)-methyl]-pyridin-3-yl}-5-(tetrahydro-pyran-4-yl)-[1,2,4]triazol-1-yl]-ethanol | A6.7 | 0.62 | 492.34 |
| A7.8 | (R)-{5-[1-Ethyl-5-(tetrahydro-pyran-4-yl)-1H-[1,2,4]triazol-3-yl]-pyridin-3-yl}-(4-isopropyl-phenyl)-(3-methyl-azetidin-3-yl)-methanol | A6.8 | 0.69 | 476.33 |
| A7.9 | (R)-(4-Isopropyl-phenyl)-{5-[1-isopropyl-5-(tetrahydro-pyran-4-yl)-1H-[1,2,4]triazol-3-yl]-pyridin-3-yl}-(3-methyl-azetidin-3-yl)-methanol | A6.9 | 0.73 | 490.36 |
| A7.10 | (R)-{5-[1-Cyclopentyl-5-(tetrahydro-pyran-4-yl)-1H-[1,2,4]triazol-3-yl]-pyridin-3-yl}-(4-isopropyl-phenyl)-(3-methyl-azetidin-3-yl)-methanol | A6.10 | 0.78 | 516.35 |
| A7.11 | (R)-{5-[1-tert-Butyl-5-(tetrahydro-pyran-4-yl)-1H-[1,2,4]triazol-3-yl]-pyridin-3-yl}-(4-isopropyl-phenyl)-(3-methyl-azetidin-3-yl)-methanol | A6.11 | 0.77 | 504.36 |
| A7.12 | (R)-{5-[1-(2,2-Difluoro-propyl)-5-(tetrahydro-pyran-4-yl)-1H-[1,2,4]triazol-3-yl]-pyridin-3-yl}-(4-isopropyl-phenyl)-(3-methyl-azetidin-3-yl)-methanol | A6.12 | 0.74 | 526.33 |
| A7.13 | (R)-{5-[1-Cyclobutyl-5-(tetrahydro-pyran-4-yl)-1H-[1,2,4]triazol-3-yl]-pyridin-3-yl}-(4-isopropyl-phenyl)-(3-methyl-azetidin-3-yl)-methanol | A6.13 | 0.76 | 502.35 |
| A7.14 | (R)-[5-(1-Cyclopropyl-5-pyridin-3-yl-1H-[1,2,4]triazol-3-yl)-pyridin-3-yl]-(4-isopropyl-phenyl)-(3-methyl-azetidin-3-yl)-methanol | A6.14 | 0.70 | 481.35 |
| A7.15 | (5-(1-cyclopropyl-5-(tetrahydro-2H-pyran-4-yl)-1H-1,2,4-triazol-3-yl)pyridin-3-yl)(3-methylazetidin-3-yl)(4-(trifluoromethoxy)phenyl)methanol | A6.15 | 0.71 | 529.49 |
| A7.16 | (R)-(4-Cyclopropyl-phenyl)-{5-[1-cyclopropyl-5-(tetrahydro-pyran-4-yl)-1H-[1,2,4]triazol-3-yl]-pyridin-3-yl}-(3-methyl-azetidin-3-yl)-methanol | A6.16 | 0.68 | 486.02 |
| A7.17 | 2-(2-Cyclopropyl-5-{5-[(R)-hydroxy-(4-isopropyl-phenyl)-(3-methyl-azetidin-3-yl)-methyl]-pyridin-3-yl}-2H-[1,2,4]triazol-3-yl)-propan-2-ol | A6.17 | 0.69 | 462.36 |
| A7.18 | 2-(5-{5-[(R)-Hydroxy-(4-isopropyl-phenyl)-(3-methyl-azetidin-3-yl)-methyl]-pyridin-3-yl}-2-isopropyl-2H-[1,2,4]triazol-3-yl)-propan-2-ol | A6.18 | 0.70 | 464.37 |
| A7.19 | (R)-{5-[1-Cyclopropyl-5-(3-hydroxymethyl-bicyclo[1.1.1]pent-1-yl)-1H-[1,2,4]triazol-3-yl]-pyridin-3-yl}-(4-isopropyl-phenyl)-(3-methyl-azetidin-3-yl)-methanol | A6.19 | 0.69 | 500.36 |
| A7.20 | (R)-{5-[5-(3-Hydroxymethyl-bicyclo[1.1.1]pent-1-yl)-1-isopropyl-1H-[1,2,4]triazol-3-yl]-pyridin-3-yl}-(4-isopropyl-phenyl)-(3-methyl-azetidin-3-yl)-methanol | A6.20 | 0.70 | 502.17 |
| A7.21 | 4-(2-Cyclopropyl-5-{5-[(R)-hydroxy-(4-isopropyl-phenyl)-(3-methyl-azetidin-3-yl)-methyl]-pyridin-3-yl}-2H-[1,2,4]triazol-3-yl)-tetrahydro-pyran-4-ol | A6.21 | 0.68 | 504.33 |
| A7.22 | 4-(5-{5-[(R)-Hydroxy-(4-isopropyl-phenyl)-(3-methyl-azetidin-3-yl)-methyl]-pyridin-3-yl}-2-isopropyl-2H-[1,2,4]triazol-3-yl)-tetrahydro-pyran-4-ol | A6.22 | 0.69 | 506.18 |
| A7.23 | 1-[4-(2-Cyclopropyl-5-{5-[(R)-hydroxy-(4-isopropyl-phenyl)-(3-methyl-azetidin-3-yl)-methyl]-pyridin-3-yl}-2H-[1,2,4]triazol-3-yl)-piperidin-1-yl]-ethanone | A6.23 | 0.70 | 529.12 |

-continued

| A7 | Name | Reactant A6 | $t_R$ [min] | MS-data m/z $[M + H]^+$ |
|---|---|---|---|---|
| A7.24 | 1-[4-(5-{5-[(R)-Hydroxy-(4-isopropyl-phenyl)-(3-methyl-azetidin-3-yl)-methyl]-pyridin-3-yl}-2-isopropyl-2H-[1,2,4]triazol-3-yl)-piperidin-1-yl]-ethanone | A6.24 | 0.71 | 531.38 |
| A7.25 | {5-[1-Cyclopropyl-5-(tetrahydro-pyran-4-yl)-1H-[1,2,4]triazol-3-yl]-pyridin-3-yl}-(3-fluoro-4-isopropyl-phenyl)-(3-methyl-azetidin-3-yl)-methanol | A6.25 | 0.73 | 506.09 |
| A7.26 | 4-(2-Cyclopropyl-5-{2-fluoro-5-[(R)-hydroxy-(4-isopropyl-phenyl)-(3-methyl-azetidin-3-yl)-methyl]-pyridin-3-yl}-2H-[1,2,4]triazol-3-yl)-trans-cyclohexanol | A6.26 | 0.74 | 520.45 |
| A7.27 | 4-(2-Cyclopropyl-5-{5-[(R)-hydroxy-(4-isopropyl-phenyl)-(3-methyl-azetidin-3-yl)-methyl]-2-methyl-pyridin-3-yl}-2H-[1,2,4]triazol-3-yl)-trans-cyclohexanol | A6.27 | 0.64 | 516.46 |
| A7.28 | (R)-(4-Isopropyl-phenyl)-{5-[1-(2-methoxy-ethyl)-5-(tetrahydro-pyran-4-yl)-1H-[1,2,4]triazol-3-yl]-pyridin-3-yl}-(3-methyl-azetidin-3-yl)-methanol | A6.28 | 0.69 | 506.37 |
| A7.29 | (R)-(4-Isopropyl-phenyl)-{6-[1-isopropyl-5-(tetrahydro-pyran-4-yl)-1H-[1,2,4]triazol-3-yl]-pyridazin-4-yl}-(3-methyl-azetidin-3-yl)-methanol | A6.29 | 0.71 | 491.35 |

Preparation of Intermediates of Formula B1

B1.1 3-[(R)-(5-Cyano-pyridin-3-yl)-hydroxy-(4-isopropyl-phenyl)-methyl]-3-methyl-azetidine-1-carboxylic acid tert-butyl ester A flask was charged with Intermediate A4.4 (10.0 g), 5-bromo-3-cyanopyridine (7.49 g) and THF (100 mL) and the mixture was cooled to −78° C., then a solution of HexLi in hexane (2.3 M, 17.8 mL) was added dropwise over 30 min. After stirring at −78° C. for 1 h the cooling bath was removed and the reaction mixture was quenched by addition of sat. aq. $NH_4Cl$. After warming to RT the mixture was diluted with EA and washed consecutively with water and brine, dried over $MgSO_4$, filtered and concentrated under vacuum to give the crude material as a brown oil. The residue was subjected to CC (CombiFlash, RediSep 330 g $SiO_2$, gradient Hep/EA 9:1 to 5:5 over 30 min @ 200 mL/min) to give a yellow amorphous solid, which was further purified by prep LC-MS (I), then the enantiomers were separated by prep chiral SFC (I) to give 3.22 g of the desired product (off-white solid) as the second eluting enantiomer. LC-MS (A): $t_R$=1.05 min; $[M+H]^+$: 422.28. Chiral SFC (A): $t_R$=2.21 min.

B1.2 5-[(R)-(1,3-Dimethyl-azetidin-3-yl)-hydroxy-(4-isopropyl-phenyl)-methyl]-nicotinonitrile

B1.2.1 5-[(R)-Hydroxy-(4-isopropyl-phenyl)-(3-methyl-azetidin-3-yl)-methyl]-nicotinonitrile Intermediate B1.1 (0.5 g) was treated with HCl (4M in dioxane, 8.9 mL). The rxn mixture was stirred at RT for 2 h and evaporated to dryness to give the crude hydrochloride salt as beige powder. LC-MS (A): $t_R$=0.69 min; $[M+H]^+$: 321.92.

B1.2.2 5-[(R)-(1,3-Dimethyl-azetidin-3-yl)-hydroxy-(4-isopropyl-phenyl)-methyl]-nicotinonitrile To a soln of Intermediate B1.2.1 (0.55 g) in anh dioxane (24 mL) was added DIPEA (1.1 mL), formaldehyde (37% soln in $H_2O$, 0.15 mL) and $NaBH(OAc)_3$ (741 mg). The rxn mixture was stirred for 15 min at RT, quenched with NaOH (1M) and extracted with EA. The combined org. phases were dried over $MgSO_4$ and concentrated in vacuo. The resulting crude was purified by CC using Sfär KP-Amino D pre-packed cartridges from Biotage® and eluting with EA/MeOH to give the title compound as yellow oil (0.34 g). LC-MS (A): $t_R$=0.70 min; $[M+H]^+$: 336.09.

B1.3 3-[(R)-(5-Cyano-6-fluoro-pyridin-3-yl)-hydroxy-(4-isopropyl-phenyl)-methyl]-3-methyl-azetidine-1-carboxylic acid tert-butyl ester The intermediate B1.3 was synthesized according to the procedure described in for B1.1, using intermediate A4.4 (2.00 g) and 5-bromo-2-fluoronicotinonitrile (1.73 g). After work-up the crude was purified by CC (CombiFlash, RediSep 330 g SiO2, gradient nHept/EtOAc 100/0 to 60/40) followed by prep LC-MS (Zorbax column SB-AQ, 7 um OBD, 50×150 mm, gradient (0.5% formic acid in H2O)/MeCN 60/40 to 25/75 in 8 min @ 150 mL/min) to give the product as racemate (630 mg). Further purification by chiral SFC (Method I) afforded the product as a white solid and enantiomerically pure (282 mg). LC-MS (A): $t_R$=1.08 min; $[M+H]^+$: 440.32. Analytical chiral SFC (A): 1.99 min.

B1.4 3-[(R)-(5-Cyano-6-methyl-pyridin-3-yl)-hydroxy-(4-isopropyl-phenyl)-methyl]-3-methyl-azetidine-1-carboxylic acid tert-butyl ester The intermediate B1.4 was synthesized according to the procedure described in for B1.3, using intermediate A4.4 (2.00 g) and 5-bromo-2-methylnicotinonitrile (1.68 g). After work-up the crude was purified by CC (CombiFlash, RediSep 220 g $SiO_2$, gradient nHept/EtOAc 100/0 to 50/50) followed by prep LC-MS (Zorbax column SB-AQ, 7 um OBD, 50×150 mm, gradient (0.5% formic acid in H2O)/MeCN 60/40 to 30/70 in 8 min @ 150 mL/min) to give the product as racemate (1.73 g mg). Further purification by chiral SFC (Method VII) afforded the product as a white solid and enantiomerically pure (619 mg). LC-MS (A): $t_R$=1.07 min; $[M+H]^+$: 436.34. Analytical chiral SFC (G): 1.82 min.

B1.5 3-[(R)-(6-Cyano-pyridazin-4-yl)-hydroxy-(4-isopropyl-phenyl)-methyl]-3-methyl-azetidine-1-carboxylic acid tert-butyl ester B1.5.1 3-[(6-Chloro-pyridazin-4-yl)-hydroxy-(4-isopropyl-phenyl)-methyl]-3-methyl-azetidine-1-carboxylic acid tert-butyl ester The title compound (4.0 g, beige solid) was synthesized starting from intermediate A4.4 (10 g) and 5-bromo-3-chloropyridazine (7.1 g), and following the procedure described in Intermediate B1.1, however using toluene instead of THF as solvent. The crude material was purified by CC (Biotage, SNAP 340 g, solvent A: Hep; solvent B: EA; gradient in % B: 0 to 50). LC-MS (A): $t_R$=1.06 min; $[M+H]^+$: 432.08.

B1.5.2. 3-[(R)-(6-Chloro-pyridazin-4-yl)-hydroxy-(4-isopropyl-phenyl)-methyl]-3-methyl-azetidine-1-carboxylic acid tert-butyl ester The title compound was obtained by chiral separation of Example B1.5.1 using Prep Chiral SFC (IX). LC-MS (A): $t_R$=1.05 min; $[M+H]^+$: 432.22; Chiral SFC (H): 2.72 min.1.5.3 3-[(R)-(6-Cyano-pyridazin-4-yl)-hydroxy-(4-isopropyl-phenyl)-methyl]-3-methyl-azetidine-1-carboxylic acid tert-butyl ester A suspension of Intermediate B1.5.2 (140 mg), zinc powder (75 mg), zinc cyanide (62 mg), $Pd_2(dba)_3$ (21 mg), dppf (103 mg) in DMF (1.5 mL) was heated at reflux for 1 h45. The reaction mixture was allowed to cool down to RT and was diluted with $H_2O$ and DCM. The layers were separated, and the aq. phase was extracted with DCM (3×). The combined org. layers were dried over $MgSO_4$ and concentrated in vacuo. Purification by prep LC-MS (VII) gave 49 mg of the desired product as beige solid. LC-MS (A): $t_R$=1.03 min; $[M+H]^+$: 423.24.

B1.6 3-{(R)-(5-Cyano-pyridin-3-yl)-hydroxy-[4-(1-trifluoromethyl-cyclopropyl)-phenyl]-methyl}-3-methyl-azetidine-1-carboxylic acid tert-butyl ester A flask was charged with Intermediate A4.3 (800 mg), 5-bromo-3-cyanopyridine (424 mg) and THF (53 mL) and the mixture was cooled to −78° C., then a solution of BuLi in hexane (2.5 M, 1.24 mL) was added dropwise over 15 min. After stirring at −78° C. for 30 min the cooling bath was removed, and the reaction mixture was quenched by addition of water.

The mixture was extracted with EA and the combined org. layers were washed with brine, dried over $MgSO_4$, filtered and concentrated under vacuum to give the crude material as a brown oil. The residue was subjected to CC (Biotage 50 g $SiO_2$, gradient Hep/EA 12% to 100%) to give a yellow foam, which was further purified by prep LC-MS (VIII), then the enantiomers were separated by prep chiral SFC (I) to give 0.15 g of the desired product as the second eluting enantiomer. LC-MS (A): $t_R$=1.06 min; $[M+H]^+$: 488.05. Chiral SFC (A): $t_R$=1.78 min.

B1.7 5-{(R)-(1,3-Dimethyl-azetidin-3-yl)-hydroxy-[4-(1-trifluoromethyl-cyclopropyl)-phenyl]-methyl}-nicotinonitrile The title compound was synthesized starting from Intermediate B1.6 (134 mg) and following the two-step procedure described for Intermediate B1.2. The crude was isolated as white foam (74 mg). LC-MS (A): $t_R$=0.73 min; $[M+H]^+$: 401.97.

Preparation of Intermediates of Formula B2

B2.1 3-[(R)-Hydroxy-[5-(N-hydroxycarbamimidoyl)-pyridin-3-yl]-(4-isopropyl-phenyl)-methyl]-3-methyl-azetidine-1-carboxylic acid tert-butyl ester (or its tautomeric form tert-butyl (R,Z)-3-(hydroxy(5-(N'-hydroxycarbamimidoyl)pyridin-3-yl)(4-isopropylphenyl)methyl)-3-methylazetidine-1-carboxylate)

To a solution of Intermediate B1.1 (1.00 g) and hydroxylamine hydrochloride (247 mg) in DMSO (5 mL) was added DIPEA (0.81 mL) dropwise. The reaction mixture was stirred at RT for 3 h. After complete conversion it was slowly (10 min) transferred to a flask containing water cooled with an ice bath. The resulting white suspension was stirred at RT for 30 min. The mixture was filtered, and the residue was washed with water three times, dried under HV overnight, then at 45° C. under vacuum. A white solid (1.09 g) was obtained. LC-MS (A): $t_R$=0.81 min; $[M+H]^+$: 455.31.

B2.2 5-[(R)-(1,3-Dimethyl-azetidin-3-yl)-hydroxy-(4-isopropyl-phenyl)-methyl]-N-hydroxy-nicotinamidine A suspension of Intermediate B1.2 (372 mg), hydroxylamine hydrochloride (234 mg) and $K_2CO_3$ (613 mg) in EtOH (8.1 mL) was stirred for 5 h at RT. It was filtered and the filtrate was concentrated in vacuo to give the crude title compound as white powder (497 mg). LC-MS (A): $t_R$=0.54 min; $[M+H]^+$: 369.04.

B2.3 3-[(R)-[6-Fluoro-5-(N-hydroxycarbamimidoyl)-pyridin-3-yl]-hydroxy-(4-isopropyl-phenyl)-methyl]-3-methyl-azetidine-1-carboxylic acid tert-butyl ester The title compound was prepared according to the procedure described for B2.1, using intermediate B1.3 (279 mg), hydroxylamine hydrochloride (66 mg) and DIPEA (0.22 mL). The crude was purified by prep LC-MS (V) to give the desired product as a light yellow solid (61 mg). LC-MS (A): $t_R$=0.87 min; $[M+H]^+$: 473.30.

B2.4 3-[(R)-Hydroxy-[5-(N-hydroxycarbamimidoyl)-6-methyl-pyridin-3-yl]-(4-isopropyl-phenyl)-methyl]-3-methyl-azetidine-1-carboxylic acid tert-butyl ester The title compound was prepared according to the procedure described for B2.1, using intermediate B1.4 (619 mg), hydroxylamine hydrochloride (148 mg) and DIPEA (0.49 mL). To push the conversion to completion, hydroxylamine and DIPEA were added several more times. The crude was purified by prep LC-MS (VI) to give the desired product as a white solid (207 mg). LC-MS (A): $t_R$=0.78 min; $[M+H]^+$: 469.38.

B2.5 3-[(R)-Hydroxy-[6-(N-hydroxycarbamimidoyl)-pyridazin-4-yl]-(4-isopropyl-phenyl)-methyl]-3-methyl-azetidine-1-carboxylic acid tert-butyl ester A suspension of Intermediate B1.5 (49 mg), hydroxylamine hydrochloride (24.4 4 mg) and $K_2CO_3$ (64 mg) in EtOH (0.84 mL) was stirred for 20 h at RT. It was filtered and the filtrate was concentrated in vacuo to give the crude title compound as brownish solid (63 mg). LC-MS (A): $t_R$=0.92 min; $[M+H]^+$: 456.28.

B2.6 5-{(R)-(1,3-Dimethyl-azetidin-3-yl)-hydroxy-[4-(1-trifluoromethyl-cyclopropyl)-phenyl]-methyl}-N-hydroxy-nicotinamidine The title compound was synthesized starting from Intermediate B1.7 (72 mg) and following the procedure described for Intermediate B2.2. The crude was isolated as white foam (74 mg). LC-MS (A): $t_R$=0.57 min; $[M+H]^+$: 435.18.

Preparation of Intermediates of Formula B3

B3.1 3-[(R)-(5-Carbamimidoyl-pyridin-3-yl)-hydroxy-(4-isopropyl-phenyl)-methyl]-3-methyl-azetidine-1-carboxylic acid tert-butyl ester To a solution of Intermediate B2.1 (400 mg) in AcOH (15 mL) was added acetic anhydride (0.11 mL). The solution was stirred at RT for 45 min. Palladium on activated carbon (10%, wet (50%), 20 mg) was added and the mixture was hydrogenated at RT for 1 h15 min. The reaction mixture was filtered over celite, the residue washed with AcOH and the combined filtrates were concentrated under vacuum to give the crude material as a colorless amorphous solid. The crude was further purified with prep LC-MS (V) to afford the title compound as a white solid (265 mg). LC-MS (A): $t_R$=0.78 min; $[M+H]^+$: 439.29.

B3.2 5-[(R)-(1,3-Dimethyl-azetidin-3-yl)-hydroxy-(4-isopropyl-phenyl)-methyl]-nicotinamidine The title compound was synthesized starting from Intermediate B2.2 (497 mg) and following the synthesis procedure described for Intermediate B3.1 except that the acetylation step was performed for 2 h at RT and the hydrogenation for 18 h at RT. The crude was isolated as yellow foam (216 mg). LC-MS (A): $t_R$=0.50 min; $[M+H]^+$: 353.04.

B3.3 3-[(R)-(5-Carbamimidoyl-6-fluoro-pyridin-3-yl)-hydroxy-(4-isopropyl-phenyl)-methyl]-3-methyl-azetidine-1-carboxylic acid tert-butyl ester The title compound was synthesized from Intermediate B2.3 (57 mg) according to the procedure described for B3.1 (acetylation 1 h, hydrogenation 2 h). The crude was purified by prep LC-MS (V) to give the desired product as a white solid (45 mg). LC-MS (A): $t_R$=0.82 min; $[M+H]^+$: 457.36.

B3.4 3-[(R)-(5-Carbamimidoyl-6-methyl-pyridin-3-yl)-hydroxy-(4-isopropyl-phenyl)-methyl]-3-methyl-azetidine-1-carboxylic acid tert-butyl ester The title compound was synthesized from Intermediate B2.4 (80 mg) according to the procedure described for B3.1 (acetylation 30 min, hydrogenation 1.5 h) to give the desired product as a white foam (75 mg). The crude was used in the next step without further purification. LC-MS (A): $t_R$=0.78 min; $[M+H]^+$: 453.38.

B3.5 3-[(R)-(6-Carbamimidoyl-pyridazin-4-yl)-hydroxy-(4-isopropyl-phenyl)-methyl]-3-methyl-azetidine-1-carboxylic acid tert-butyl ester The title compound was synthesized from Intermediate B2.5 (52 mg) according to the procedure described for B3.1 (acetylation 17 h, hydrogenation 23 h). After reaction completion the reaction mixture was filtered, the filtrate basified to pH 12 by the addition of 1N NaOH and extracted with DCM (3×). The combined org. layers were dried over $MgSO_4$ and concentrated in vacuo to give the desired product as a yellowish solid (75 mg). The crude was used in the next step without further purification. LC-MS (A): $t_R$=0.79 min; $[M+H]^+$: 440.28.

B3.6 5-{(R)-(1,3-Dimethyl-azetidin-3-yl)-hydroxy-[4-(1-trifluoromethyl-cyclopropyl)-phenyl]-methyl}-nicotinamidine The title compound was synthesized starting from Intermediate B2.6 (70 mg) and following the synthesis procedure described for Intermediate B3.1. LC-MS (A): $t_R$=0.53 min; $[M+H]^+$: 419.23.

Preparation of Intermediates of Formula B4

B4.1 3-(Hydroxymethyl)bicyclo[1.1.1]pentane-1-carboxylic acid

To a solution of 3-(hydroxymethyl)bicyclo[1.1.1]pentane-1-carbonitrile (150 mg) in EtOH (2.3 mL) was added water (0.5 mL) and aq. NaOH (10.8M, 0.65 mL). The reaction mixture was stirred at 75° C. for 2 h. After cooling to RT, the mixture was acidified (pH 2-3) with aq. HCl (6.8M, ~1 mL). The mixture was extracted with EA four times, the combined organic layers were dried over $MgSO_4$, filtered and concentrated under vacuum to give the title compound as white solid (180 mg). $^1$H-NMR (500 MHz, DMSO) δ=12.2 (br s, 1H), 4.54 (t, J=5.6 Hz, 1H), 3.37 (d, J=5.4 Hz, 2H), 1.81 (s, 6H) ppm.

Preparation of Examples 1 to 4 and 38

To a soln of Intermediate A7 (1 eq) in anh dioxane (18.3 mL/mmol) was added DIPEA (3 eq), formaldehyde (37% soln in $H_2O$, 1.5 eq) and $NaBH(OAc)_3$ (2.6 eq). The rxn mixture was stirred for 15 min to 1 h at RT, quenched with NaOH (1M) and extracted with EA. The combined org. phases were dried over $MgSO_4$ and concentrated in vacuo. The resulting crude was purified by prep LC-MS using the conditions listed in the table below, followed by prep chiral SFC as indicated in the table below. The pure enantiomers were characterized by anal chiral SFC (with method and retention times in minutes ($t_R$ chiral) given in the table below) and by anal LC-MS (Method A, retention times ($t_R$ LC-MS) in minutes and observed mass indicated in the table below).

| Example | Name | Reactant A7 | Prep LC-MS | Prep chiral method | Anal chiral method | $t_R$ chiral | $t_R$ LC-MS | m/z $[M + H]^+$ |
|---|---|---|---|---|---|---|---|---|
| 1 | (R)-(4-Bromo-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol | A7.1 | (IV) | (IV) | D | 2.29 | 0.70 | 537.97 |
| 2 | (R)-(4-tert-Butyl-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol | A7.2 | (III) | (V) | E | 2.68 | 0.76 | 516.13 |
| 3 | (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-[4-(1-trifluoromethyl-cyclopropyl)-phenyl]-methanol | A7.3 | (III) | (VI) | F | 2.88 | 0.75 | 568.12 |
| 4 | (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-trifluoromethoxy-phenyl)-methanol | A7.15 | (IV) + (V) | (II) | B | 2.11 | 0.73 | 543.98 |
| 38 | (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(3-fluoro-4-isopropyl-phenyl)-methanol | A7.25 | (III) | (VI) | B | 3.57 | 0.75 | 520.09 |

Preparation of Examples 5 to 7

A mixture of Example 1 (1 eq), organoborane (2 eq), cataCXium®A Pd G3 (0.1 eq) and $Cs_2CO_3$ (3 eq) in a mixture of toluene (5 mL/mmol) and water (0.5 mL/mmol) was flushed with argon, heated at 100° C. in a sealed vial and stirred for 18 h. The rxn mixture was diluted with EA and washed with NaOH (1 M) and brine. The org. phase was dried over $MgSO_4$ and concentrated in vacuo. The crude was purified by prep LC-MS using the method indicated in the table below.

| Example | Name | Reactant organoborane | Prep LC-MS | $t_R$ [min] | MS-data m/z $[M + H]^+$ |
|---|---|---|---|---|---|
| 5 | (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-[4-(2,2,2-trifluoro-ethyl)-phenyl]-methanol | 4,4,5,5-Tetramethyl-2-(2,2,2-trifluoro ethyl)-1,3,2-dioxaborolane | (IV) | 0.72 | 542.04 |
| 6 | (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-ethyl-phenyl)-methanol | Potassium ethyltrifluoroborate | (IV) | 0.70 | 488.12 |
| 7 | (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-propyl-phenyl)-methanol | Potassium n-propyl trifluoroborate | (III) | 0.74 | 502.13 |

Preparation of Examples 8 to 12

To a mixture of Intermediate B3.2 (1 eq), carboxylic acid (1.5 eq) and HATU (1.1 eq) in DMF (5 mL/mmol) was added DIPEA (4 eq). After stirring at RT for 1 to 1.5 h until complete formation of the intermediate, cyclopropylhydrazine hydrochloride (1.5 eq) and AcOH (10 eq) were added at RT. The reaction was stirred at 80° C. for 20 min to 18 h. After cooling to RT, the mixture was diluted with EA, washed with 1M aq. NaOH and brine, dried over $MgSO_4$ and concentrated in vacuo. The crude was purified by prep. LC-MS using the conditions listed in the table below.

| Example | Name | Reactant Acid | Prep LC-MS | $t_R$ [min] | MS-data m/z $[M + H]^+$ |
|---|---|---|---|---|---|
| 8 | trans-4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-cyclohexanol | trans-4-Hydroxycyclohexane carboxylic acid | (IV) | 0.70 | 516.14 |
| 9 | (R)-2-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-1,1,1-trifluoro-propan-2-ol | (2R)-2-Hydroxy-2-(trifluoromethyl)propanoic acid | (IX) | 0.79 | 529.79 |
| 10 | 4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-bicyclo[2.2.2]octane-1-carboxylic acid methyl ester | 4-(Methoxycarbonyl) bicyclo[2.2.2]octane-1-carboxylic acid | (IX) | 0.85 | 584.18 |
| 11 | (R)-{5-[1-Cyclopropyl-5-(1-methyl-1-methylamino-ethyl)-1H-[1,2,4]triazol-3-yl]-pyridin-3-yl}-(1,3-dimethyl-azetidin-3-yl)-(4-isopropyl-phenyl)-methanol | 2-({[(9H-fluoren-9-yl)methoxy]carbon-yl}(methyl)amino)-2-methylpropanoic acid | (IX) | 0.60 | 489.15 |
| 12 | 1-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-ylmethyl)-cyclobutanol | 2-(1-Hydroxy cyclobutyl)acetic acid | (IX) | 0.72 | 502.12 |

Preparation of Example 13: 4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-bicyclo[2.2.2]octane-1-carboxylic acid To a soln. of Example 10 (1 eq) in MeOH (8.6 mL/mmol) was added $LiOH \cdot H_2O$ (1.5 eq) and $H_2O$ (4.3 mL/mmol). The rxn mixture was stirred for 18 h at RT, concentrated in vacua and partitioned between EA and half sat. aq. $NH_4Cl$. The org. phase was washed with brine, dried over $MgSO_4$ and concentrated in vacuo to give the title compound as yellowish oily residue. LC-MS (A): $t_R$=0.76 min; $[M+H]^+$: 570.16

Preparation of Examples 14 to 33, 39, 40, 48, and 51

To a solution of Intermediate A7 (1 eq.) in dioxane (10 mL/mmol) was added TEA (2 eq.) or AcOH (1.5 eq; for Example 48), aq. formaldehyde (37 wt.-%, 2 eq.) and $NaBH(OAc)_3$ (1.5 eq.). The mixture was stirred at RT overnight to reach full conversion of the starting material. The reaction mixture was filtered and concentrated under vacuum, then purified by prep LC-MS to give the desired compound. Prep LC-MS methods are given in the table below. Example 39 was additionally purified by chiral SFC (VI II) to separate the product from unreacted starting material.

| Example | Name | Reactant (A7) | prep LC-MS | $t_R$ [min] | MS-data m/z $[M + H]^+$ |
|---|---|---|---|---|---|
| 14 | (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol | A7.4 | (III) | 0.72 | 502.20 |
| 15 | (R)-{5-[1-Cyclohexyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol | A7.5 | (II) | 0.81 | 544.42 |
| 16 | (R)-(1,3-Dimethyl-azetidin-3-yl)-(4-isopropyl-phenyl)-{5-[1-methyl-5-(tetrahydro-pyran-4-yl)-1H-[1,2,4]triazol-3-yl]-pyridin-3-yl}-methanol | A7.6 | (IV) | 0.69 | 476.37 |
| 17 | 2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethanol | A7.7 | (VI) + (III) | 0.64 | 506.35 |
| 18 | (R)-(1,3-Dimethyl-azetidin-3-yl)-{5-[1-ethyl-5-(tetrahydro-pyran-4-yl)-1H-[1,2,4]triazol-3-yl]-pyridin-3-yl}-(4-isopropyl-phenyl)-methanol | A7.8 | (VI) + (III) | 0.72 | 490.32 |
| 19 | (R)-(1,3-Dimethyl-azetidin-3-yl)-(4-isopropyl-phenyl)-{5-[1-isopropyl-5-(tetrahydro-pyran-4-yl)-1H-[1,2,4]triazol-3-yl]-pyridin-3-yl}-methanol | A7.9 | (III) | 0.75 | 504.37 |
| 20 | (R)-{5-[1-Cyclopentyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol | A7.10 | (II) | 0.81 | 530.27 |

-continued

| Example | Name | Reactant (A7) | prep LC-MS | $t_R$ [min] | MS-data m/z $[M + H]^+$ |
|---|---|---|---|---|---|
| 21 | (R)-{5-[1-tert-Butyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol | A7.11 | (II) | 0.79 | 518.37 |
| 22 | (R)-{5-[1-(2,2-Difluoro-propyl)-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol | A7.12 | (III) | 0.76 | 540.30 |
| 23 | (R)-{5-[1-Cyclobutyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol | A7.13 | (III) | 0.78 | 516.36 |
| 24 | (R)-[5-(1-Cyclopropyl-5-pyridin-3-yl-1H-[1,2,4]triazol-3-yl)-pyridin-3-yl]-(1,3-dimethyl-azetidin-3-yl)-(4-isopropyl-phenyl)-methanol | A7.14 | III + VI + CC ($SiO_2$, DCM/MeOH + 1% $NH_4OH$ 100:0 to 8:2) | 0.73 | 495.36 |
| 25 | (R)-(4-Cyclopropyl-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol | A7.16 | (III) | 0.71 | 500.11 |
| 26 | 2-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-propan-2-ol | A7.17 | (VI) | 0.71 | 476.39 |
| 27 | 2-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-propan-2-ol | A7.18 | (VI) | 0.72 | 478.37 |
| 28 | (R)-{5-[1-Cyclopropyl-5-(3-hydroxymethyl-bicyclo[1.1.1]pent-1-yl)-1H-[1,2,4]triazol-3-yl]-pyridin-3-yl}-(1,3-dimethyl-azetidin-3-yl)-(4-isopropyl-phenyl)-methanol | A7.19 | (VI) | 0.71 | 514.23 |
| 29 | (R)-(1,3-Dimethyl-azetidin-3-yl)-{5-[5-(3-hydroxymethyl-bicyclo[1.1.1]pent-1-yl)-1-isopropyl-1H-[1,2,4]triazol-3-yl]-pyridin-3-yl}-(4-isopropyl-phenyl)-methanol | A7.20 | (VI) | 0.72 | 516.34 |
| 30 | 4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-tetrahydro-pyran-4-ol | A7.21 | (VI) | 0.70 | 518.34 |
| 31 | 4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-tetrahydro-pyran-4-ol | A7.22 | (VI) | 0.70 | 520.31 |
| 32 | 1-[4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-piperidin-1-yl]-ethanone | A7.23 | (VI) | 0.72 | 543.40 |
| 33 | 1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-1-yl]-ethanone | A7.24 | (VI) | 0.72 | 545.17 |
| 39 | 4-(2-Cyclopropyl-5-{5-[(R)-(1,3-dimethyl-azetidin-3-yl)-hydroxy-(4-isopropyl-phenyl)-methyl]-2-fluoro-pyridin-3-yl}-2H-[1,2,4]triazol-3-yl)-trans-cyclohexanol | A7.26 | (III) | 0.75 | 534.30 |
| 40 | 4-(2-Cyclopropyl-5-{5-[(R)-(1,3-dimethyl-azetidin-3-yl)-hydroxy-(4-isopropyl-phenyl)-methyl]-2-methyl-pyridin-3-yl}-2H-[1,2,4]triazol-3-yl)-trans-cyclohexanol | A7.27 | (III) | 0.65 | 530.34 |
| 48 | (R)-(1,3-Dimethyl-azetidin-3-yl)-(4-isopropyl-phenyl)-{5-[1-(2-methoxy-ethyl)-5-(tetrahydro-pyran-4-yl)-1H-[1,2,4]triazol-3-yl]-pyridin-3-yl}-methanol | A7.28 | (III) | 0.70 | 520.30 |
| 51 | (R)-(1,3-Dimethyl-azetidin-3-yl)-(4-isopropyl-phenyl)-{6-[1-isopropyl-5-(tetrahydro-pyran-4-yl)-1H-[1,2,4]triazol-3-yl]-pyridazin-4-yl}-methanol | A7.29 | (V) | 0.72 | 505.40 |

Preparation of Example 34: (R)-{5-[1-Cyclopropyl-5-(tetrahydro-pyran-4-yl)-1H-[1,2,4]triazol-3-yl]-pyridin-3-yl}-(1-isopropyl-3-methyl-azetidin-3-yl)-(4-isopropyl-phenyl)-methanol To a solution of Intermediate A7.4 (30 mg) in MeOH (1 mL), AcOH (100 μL) and acetone (44.4 μL) was added $NaB(OAc)_3H$ (44 mg) at RT. The resulting suspension was stirred at RT for 3 h30, then quenched with water, diluted with MeOH and purified by prep LC-MS (III) to give 7 mg of the title compound as white powder. LC-MS (A): $t_R$=0.77 min; $[M+H]^+$: 530.20

Preparation of Examples 35 to 37, and 49

Example 35: (R)-{5-[1-Cyclopropyl-5-(tetrahydro-pyran-4-yl)-1H-[1,2,4]triazol-3-yl]-pyridin-3-yl}-[1-(2,2-difluoro-ethyl)-3-methyl-azetidin-3-yl]-(4-isopropyl-phenyl)-methanol To a solution of Intermediate A7.4 (30 mg) in MeOH (1 mL) was added TEA (36.4 μL) followed by 1,1-difluoro-2-iodoethane (39 μL) at RT. The solution was shaken at 65° C. for 101 h before it was allowed to cool down, diluted with MeOH and water and purified by prep LC-MS (III) to give 6 mg of the title compound as off-white powder. LC-MS (A): $t_R$=0.76 min; $[M+H]^+$: 552.10

Example 36: 2-{3-[(R)-{5-[1-Cyclopropyl-5-(tetrahydro-pyran-4-yl)-1H-[1,2,4]triazol-3-yl]-pyridin-3-yl}-hydroxy-(4-isopropyl-phenyl)-methyl]-3-methyl-azetidin-1-yl}-ethanol The title compound was synthesized following the procedure described in Example 35, using 2-iodoethanol (17.5 μL), stirring for 70 h and purified by prep LC-MS (IV) to afford 3 mg of the title compound as white powder. LC-MS (A): $t_R$=0.71 min; $[M+H]^+$: 532.10.

Example 37: 2-(2-Cyclopropyl-5-{5-[(R)-hydroxy-(4-isopropyl-phenyl)-(3-methyl-azetidin-3-yl)-methyl]-pyridin-3-yl}-2H-[1,2,4]triazol-3-yl)-propan-2-ol Intermediate A7.17 served as Example 37. The procedure and characterization are described in section A7. LC-MS (A): $t_R$=0.69 min; $[M+H]^+$: 462.36.

Example 49: (R)-(1-Cyclopropyl-3-methyl-azetidin-3-yl)-{5-[1-cyclopropyl-5-(tetrahydro-pyran-4-yl)-1H-[1,2,4]triazol-3-yl]-pyridin-3-yl}-(4-isopropyl-phenyl)-methanol To a solution of Intermediate A7.4 (24 mg) in MeOH (1 mL), AcOH (5.6 μL) and (1-ethoxycyclopropoxy)trimethylsilane (30 μL) was added $NaBH_3CN$ (30 μL) at 65° C. The reaction mixture was stirred for 6 h30, then filtered through a syringe filter, diluted with water and directly purified by prep LC-MS (IV) to give 8 mg of the title compound as white powder. LC-MS (A): $t_R$=0.77 min; $[M+H]^+$: 528.36.

Preparation of Examples 41 to 47

To a mixture of Intermediate B3.2 (1 eq), carboxylic acid (1.5 eq) and HATU (1.1 eq) in DMF (5 mL/mmol) was added DIPEA (4 eq). After stirring at 40-45° C. for 15-60 min and if required overnight at RT until complete formation of the intermediate, isopropylhydrazine hydrochloride (1.5 eq) and AcOH (10 eq) were added at RT. The reaction was stirred at 80° C. for 10-45 min. After cooling to RT, the mixture was diluted with EA, washed with 1 M aq. NaOH and brine, dried over $MgSO_4$ and concentrated in vacuo. The crude was purified by an optional Biotage chromatography followed by prep. LC-MS using the conditions listed in the table below.

| Example | Name | Reactant Acid | Prep LC-MS | $t_R$ [min] | MS-data m/z $[M + H]^+$ |
|---|---|---|---|---|---|
| 41 | (R)-(1,3-Dimethyl-azetidin-3-yl)-(4-isopropyl-phenyl)-[5-(1-isopropyl-5-propyl-1H-[1,2,4]triazol-3-yl)-pyridin-3-yl]-methanol | Butyric acid | (II) | 0.78 | 462.17 |
| 42 | 4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-1-methyl-piperidin-2-one | 1-Methyl-2-oxopiperidine-4-carboxylic acid | (IV) | 0.71 | 531.19 |
| 43 | N-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-trans-cyclohexyl]-acetamide | 4-Acetamidocyclohexane-1-carboxylic acid | Biotage followed by (III) | 0.72 | 559.38 |
| 44 | 1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-1-yl]-2-hydroxy-ethanone | 1-(2-hydroxyacetyl)piperidine-4-carboxylic acid | Biotage followed by (IV) | 0.69 | 561.19 |
| 45 | 4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-4-methyl-piperidin-2-one | 4-Methyl-2-oxopiperidine-4-carboxylic acid | Biotage followed by (IV) | 0.70 | 531.39 |
| 46 | 4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-2-one | 2-Oxopiperidine-4-carboxylic acid | Biotage followed by (IV) | 0.68 | 517.35 |

-continued

| Example | Name | Reactant Acid | Prep LC-MS | $t_R$ [min] | MS-data m/z [M + H]+ |
|---|---|---|---|---|---|
| 47 | 1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-4-hydroxy-piperidin-1-yl]-ethanone | 1-acetyl-4-hydroxypiperidine-4-carboxylic acid | Biotage followed by (IV) | 0.70 | 561.22 |

Preparation of Example 50: N-{2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethyl}-acetamide 50.1: {2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethyl}-carbamic acid tert-butyl ester To a mixture of Intermediate B3.2 (175 mg), tetrahydro-pyran-4-carboxylic acid (79 mg), molecular sieves (3 A, 50 mg) and HATU (234 mg) in DMF (3 mL) was added DIPEA (0.34 mL). After stirring at RT for 60 min, tert-butyl-N-(2-hydrazinylethyl)carbamate hydrochloride (158 mg) and AcOH (0.284 mL) were added at RT. The reaction was stirred at 85° C. for 60 min. After cooling to RT, the mixture was neutralized by the addition of sat. aq. $NaHCO_3$ and extracted with EA. The combined org. layers were dried over $MgSO_4$ and concentrated in vacuo. The crude was purified by prep.

LC-MS (III) to give the title compound as white solid (0.14 g). LC-MS (A): $t_R$=0.76 min; $[M+H]^+$: 605.41.

50.2: (R)-{5-[1-(2-Amino-ethyl)-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol To Intermediate 50.1 (140 mg) was added 4M HCl in dioxane (5 mL) and the colorless solution was stirred at RT for 30 min. The reaction mixture was set to a pH of 7-8 by the addition of sat. aq. $NaHCO_3$ and was diluted with $H_2O$. The aq. phase was extracted with EA (5×). The combined org. phases were dried over $MgSO_4$, concentrated in vacuo. The aq. layer was then basified to pH 10 by the addition of 1M NaOH and extracted with DCM. The combined org. layers were dried over $MgSO_4$ and concentrated in vacuo. Both crudes were combined and dried at HV overnight to give the title compound (107 mg) as yellowish foam. LC-MS (A): $t_R$=0.55 min; $[M+H]^+$: 505.40.

50.3: N-{2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethyl}-acetamide To a a solution of Intermediate 50.2 (50 mg) in dioxane (0.5 mL) was added DIPEA (33 μL) followed by acetic anhydride (9 μL) and the mixture was stirred at RT for 1 h. The reaction mixture was evaporated to dryness, the residue was dissolved in MeOH and treated with $K_2CO_3$. After stirring for 2 h at RT, the reaction mixture was filtered, diluted with water and $CH_3CN$ and directly purified by prep. LC-MS (IV) to give 24 mg of the desired product as white solid. LC-MS (A): $t_R$=0.63 min; $[M+H]^+$: 547.35.

II. Biological Assays

FLIPR assay: The bioactivity of compounds is tested in a fluorometric imaging plate reader (FLIPR: Molecular Devices) using engineered HEK-293 cells expressing the human CCR6 (GenBank: AY242126). Frozen cells are plated on Poly-L-Lysine precoated 384-well plates 2 days prior to bioassay in DMEM medium supplemented with 10% FCS and 1% Penicillin-Streptomycin. At the day of bioassay, cell supernatant is discarded and cells are dye loaded for 30 minutes at room temperature in the dark with Fluo-8-AM (Focus Biomolecules) in Hanks Balanced Salt Solution (Gibco), buffered with 20 mM Hepes at pH 6.75 and supplemented with 0.05% BSA. This buffer, but lacking the dye, is also used for washing and compound dilution steps (assay buffer). Cells are washed free of excess dye with a wash-station (Biotek), leaving 40 microliter of assay buffer at the end. Cells were incubated for 15 minutes at room temperature in the dark, before adding compounds. Stock solutions of test compounds are made up at a concentration of 10 mM in DMSO, and serially diluted first in DMSO and then transferred in assay buffer to concentrations required for inhibition dose response curves. After a 45 minute incubation period in assay buffer at room temperature, 10 microliters of each compound dilution are transferred from a compound plate to the plate containing the recombinant cells in the FLIPR instrument according to the manufacturer's instructions. After cells and compounds were preincubated for 30 minutes at room temperature in the dark, 10 microliter agonist CCL20 (Peprotech) at a final concentration of 10 nM is added, again using the FLIPR instrument. Changes in fluorescence are monitored before and after addition of the test compounds and agonist. Emission peak values above base level after CCL20 addition are exported after base line subtraction. The calculated $IC_{50}$ values may fluctuate depending on the daily assay performance. Fluctuations of this kind are known to those skilled in the art. In the case where $IC_{50}$ values have been determined several times for the same compound, mean values are given. Data are shown in the table below.

| Example No | FLIPR $IC_{50}$ (nM) |
|---|---|
| 1 | 1050 |
| 2 | 81.1 |
| 3 | 49.8 |
| 4 | 114 |
| 5 | 182 |
| 6 | 124 |
| 7 | 44.4 |
| 8 | 98.5 |
| 9 | 22.2 |

-continued

| Example No | FLIPR $IC_{50}$ (nM) |
|---|---|
| 10 | 43.9 |
| 11 | 519 |
| 12 | 114 |
| 13 | 149 |
| 14 | 118 |
| 15 | 16.8 |
| 16 | 221 |
| 17 | 508.5 |
| 18 | 165.5 |
| 19 | 94.8 |
| 20 | 37.3 |
| 21 | 39.9 |
| 22 | 81.6 |
| 23 | 57.8 |
| 24 | 50.1 |
| 25 | 163 |
| 26 | 46.4 |
| 27 | 59.5 |
| 28 | 61.1 |
| 29 | 78.7 |
| 30 | 98.1 |
| 31 | 86.3 |
| 32 | 181 |
| 33 | 182 |
| 34 | 63.8 |
| 35 | 72.6 |
| 36 | 116 |
| 37 | 104 |
| 38 | 78.1 |
| 39 | 76.6 |
| 40 | 202 |
| 41 | 45.3 |
| 42 | 200 |
| 43 | 115 |
| 44 | 199 |
| 45 | 193 |
| 46 | 161 |
| 47 | 206 |
| 48 | 170 |
| 49 | 55.8 |
| 50 | 481 |
| 51 | 578 |

The invention claimed is:

1. A compound of Formula (I)

Formula (I)

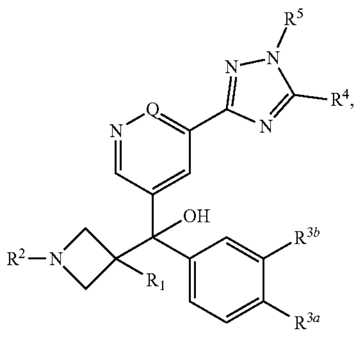

wherein

Q represents N, CH, or C—R, wherein R represents halogen or $C_{1-3}$-alkyl;

$R^1$ represents $C_{1-3}$-alkyl;

$R^2$ represents hydrogen;

$C_{1-4}$-alkyl;

hydroxy-$C_{1-3}$-alkyl;

$C_{1-3}$-fluoroalkyl; or $C_{3-5}$-cycloalkyl;

$R^{3a}$ represents halogen;

$C_{1-5}$-alkyl;

$C_{1-3}$-fluoroalkyl;

$C_{1-3}$-fluoroalkoxy;

$C_{3-5}$-cycloalkyl; or 1-($C_{1-3}$-fluoroalkyl)-$C_{3-5}$-cycloalkyl;

$R^{3b}$ represents hydrogen; or halogen;

$R^4$ represents $C_{1-4}$-alkyl which is unsubstituted; mono-substituted, wherein the substituent is selected from hydroxy or $C_{1-3}$-alkyl-amino; or di-substituted, wherein the first substituent represents hydroxy, and the second substituent represents $C_1$-fluoroalkyl; or -L-Cy, wherein -L- represents a direct bond or —$CH_2$—; and Cy represents $C_{3-7}$-cycloalkyl optionally containing one ring heteroatom selected from nitrogen or oxygen; wherein Cy independently is unsubstituted; or mono-substituted with hydroxy;

oxo;

$C_{1-4}$-alkyl;

—C(═O)$R^A$, wherein $R^A$ represents $C_{1-3}$-alkyl or hydroxy-$C_{1-3}$-alkyl; or $C_{1-3}$-alkyl-carbonyl-amino; or di-substituted, wherein the first substituent represents oxo, and the second substituent represents $C_{1-3}$-alkyl; or di-substituted, wherein the first substituent represents hydroxy and the second substituent represents $C_{1-3}$-alkyl-carbonyl;

or Cy represents a saturated 5- to 8-membered bridged bicyclic hydrocarbon ring system, wherein Cy independently is mono-substituted, wherein the substituent is selected from hydroxy-$C_{1-3}$-alkyl; or —C(═O)$R^B$, wherein $R^B$ represents hydroxy;

—$NR^{N1}R^{N2}$, wherein $R^{N1}$ and $R^{N2}$ independently represent hydrogen or $C_1$-3-alkyl; or $R^{N1}$ and $R^{N2}$ together with the nitrogen atom to which they are attached form pyrrolidinyl; or $C_{1-3}$-alkoxy;

or Cy represents a 5- or 6-membered heteroaryl containing one or two ring heteroatoms independently selected from nitrogen or oxygen; and $R^5$ represents $C_{1-4}$-alkyl;

hydroxy-$C_{1-3}$-alkyl;

$C_{1-3}$-alkoxy-$C_{1-3}$-alkyl;

$C_{3-7}$-cycloalkyl;

$C_{1-3}$-fluoroalkyl;

$C_{1-3}$-alkyl-carbonyl; or $C_{1-3}$-alkyl-carbonyl-amino-$C_{1-3}$-alkyl;

or $R^4$ and $R^5$ together with the triazolyl ring to which they are attached form 5,6,7,8-tetrahydro-[1,2,4]triazolo[1,5-a]pyridin-2-yl or 6,7-dihydro-5H-pyrrolo[1,2-b][1,2,4]triazol-2-yl;

or a pharmaceutically acceptable salt thereof.

2. A compound according to claim 1, wherein

Q represents CH;

$R^1$ represents $C_{1-3}$-alkyl;

$R^2$ represents hydrogen;

$C_{1-4}$-alkyl;

hydroxy-$C_{1-3}$-alkyl; or $C_{1-3}$-fluoroalkyl;

$R^{3a}$ represents halogen;

$C_{1-5}$-alkyl;

$C_{1-3}$-fluoroalkyl;

$C_{1-3}$-fluoroalkoxy;

$C_{3-5}$-cycloalkyl; or 1-($C_{1-3}$-fluoroalkyl)-$C_{3-5}$-cycloalkyl;

$R^{3b}$ represents hydrogen;

$R^4$ represents $C_{1-4}$-alkyl which is mono-substituted, wherein the substituent is selected from hydroxy or $C_{1-3}$-alkyl-amino; or di-substituted, wherein the first substituent represents hydroxy, and the second substituent represents $C_1$-fluoroalkyl; or -L-Cy, wherein -L- represents a direct bond or —$CH_2$—; and Cy represents $C_{3-7}$-cycloalkyl optionally containing one ring heteroatom selected from nitrogen or oxygen, wherein Cy independently is unsubstituted; or mono-substituted with hydroxy; or —C(═O)$R^A$, wherein $R^A$ represents $C_{1-3}$-alkyl;

or Cy represents a saturated 5- to 8-membered bridged bicyclic hydrocarbon ring system, wherein Cy independently is mono-substituted, wherein the substituent is selected from hydroxy-$C_{1-3}$-alkyl; or —C(═O)$R^B$, wherein $R^B$ represents hydroxy; or $C_{1-3}$-alkoxy;

or Cy represents a 6-membered heteroaryl containing one ring nitrogen atom; and $R^5$ represents $C_{1-4}$-alkyl;

hydroxy-$C_{1-3}$-alkyl;

$C_{3-7}$-cycloalkyl; or $C_{1-3}$-fluoroalkyl;

or a pharmaceutically acceptable salt thereof.

3. A compound according to claim 1, wherein $R^{3a}$ represents $C_{1-5}$-alkyl or $C_{1-3}$-fluoroalkyl; or a pharmaceutically acceptable salt thereof.

4. A compound according to claim 1, wherein $R^2$ represents $C_{1-4}$-alkyl or hydroxy-$C_{1-3}$-alkyl; or a pharmaceutically acceptable salt thereof.

5. A compound according to claim 1, wherein $R^4$ represents $C_{1-4}$-alkyl which is mono-substituted with hydroxy; or di-substituted, wherein the first substituent represents hydroxy, and the second substituent represents $C_1$-fluoroalkyl; or -L-Cy, wherein -L- represents a direct bond; and Cy represents $C_{3-7}$-cycloalkyl optionally containing one ring heteroatom selected from nitrogen or oxygen; wherein Cy independently is unsubstituted; or mono-substituted with hydroxy; or —C(═O)$R^A$, wherein $R^A$ represents $C_{1-3}$-alkyl;

or Cy represents bicyclo[1.1.1]pentan-1-yl or bicyclo[2.2.2]octan-1-yl, wherein Cy independently is mono-substituted, wherein the substituent is selected from hydroxy-$C_{1-3}$-alkyl; or —C(═O)$R^B$, wherein $R^B$ represents hydroxy; or #$C_{1-3}$-alkoxy;

or Cy represents pyridinyl;

or a pharmaceutically acceptable salt thereof.

6. A compound according to claim 1, wherein $R^5$ represents $C_{1-4}$-alkyl or $C_{3-7}$-cycloalkyl; or a pharmaceutically acceptable salt thereof.

7. A compound according to claim 1, wherein a) the radical

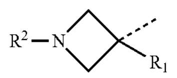

represents 3-methyl-azetidine-3-yl, 1,3-dimethyl-azetidine-3-yl, 1-isopropyl-3-methyl-azetidine-3-yl, 1-(2-hydroxyethyl)-3-methyl-azetidine-3-yl, or 1-(2,2-difluoroethyl)-3-methyl-azetidine-3-yl;

b) the radical

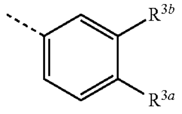

represents 4-bromo-phenyl, 4-ethyl-phenyl, 4-(n-propyl)-phenyl, 4-isopropyl-phenyl, 4-tert-butyl-phenyl, 4-cyclopropyl-phenyl, 4-(2,2,2-trifluoroethyl)-phenyl, 4-trifluoromethoxy-phenyl, or 4-(1-trifluoromethyl-cyclopropyl)-phenyl;

c) the radical

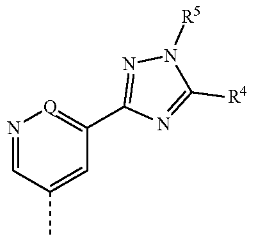

represents 5-(1-cyclopropyl-5-tetrahydropyran-4-yl-1H-1,2,4-triazol-3-yl)-pyridin-3-yl, 5-(1-cyclopropyl-5-(4-hydroxy-cyclohexyl)-1H-1,2,4-triazol-3-yl)-pyridin-3-yl, 5-(1-cyclopropyl-5-(1-hydroxy-1-trifluoromethyl-ethyl)-1H-1,2,4-triazol-3-yl)-pyridin-3-yl, 5-(1-cyclopropyl-5-(4-methoxycarbonyl-bicyclo[2.2.2]octan-1-yl)-1H-1,2,4-triazol-3-yl)-pyridin-3-yl, 5-(1-cyclopropyl-5-(1-methyl-1-methylamino-ethyl)-1H-1,2,4-triazol-3-yl)-pyridin-3-yl, 5-(1-cyclopropyl-5-(1-hydroxy-cyclobutyl-methyl)-1H-1,2,4-triazol-3-yl)-pyridin-3-yl, 5-(1-cyclopropyl-5-(4-carboxy-bicyclo[2.2.2]octan-1-yl)-1H-1,2,4-triazol-3-yl)-pyridin-3-yl, 5-(1-cyclohexyl-5-tetrahydropyran-4-yl-1H-1,2,4-triazol-3-yl)-pyridin-3-yl, 5-(1-methyl-5-tetrahydropyran-4-yl-1H-1,2,4-triazol-3-yl)-pyridin-3-yl, 5-(1-(2-hydroxyethyl)-5-tetrahydropyran-4-yl-1H-

1,2,4-triazol-3-yl)-pyridin-3-yl, 5-(1-ethyl-5-tetrahydropyran-4-yl-1H-1,2,4-triazol-3-yl)-pyridin-3-yl, 5-(1-isopropyl-5-tetrahydropyran-4-yl-1H-1,2,4-triazol-3-yl)-pyridin-3-yl, 5-(1-cyclopentyl-5-tetrahydropyran-4-yl-1H-1,2,4-triazol-3-yl)-pyridin-3-yl, 5-(1-tert-butyl-5-tetrahydropyran-4-yl-1H-1,2,4-triazol-3-yl)-pyridin-3-yl, 5-(1-(2,2-difluoropropyl)-5-tetrahydropyran-4-yl-1H-1,2,4-triazol-3-yl)-pyridin-3-yl, 5-(1-cyclobutyl-5-tetrahydropyran-4-yl-1H-1,2,4-triazol-3-yl)-pyridin-3-yl, 5-(1-cyclopropyl-5-(pyridin-3-yl)-1H-1,2,4-triazol-3-yl)-pyridin-3-yl, 5-(1-cyclopropyl-5-(1-hydroxy-1-methyl-ethyl)-1H-1,2,4-triazol-3-yl)-pyridin-3-yl, 5-(1-isopropyl-5-(1-hydroxy-1-methyl-ethyl)-1H-1,2,4-triazol-3-yl)-pyridin-3-yl, 5-(1-cyclopropyl-5-(3-(hydroxymethyl)-bicyclo[1.1.1]pentan-1-yl)-1H-1,2,4-triazol-3-yl)-pyridin-3-yl, 5-(1-isopropyl-5-(3-(hydroxymethyl)-bicyclo[1.1.1]pentan-1-yl)-1H-1,2,4-triazol-3-yl)-pyridin-3-yl, 5-(1-cyclopropyl-5-(4-hydroxy-tetrahydropyran-4-yl)-1H-1,2,4-triazol-3-yl)-pyridin-3-yl, 5-(1-isopropyl-5-(4-hydroxy-tetrahydropyran-4-yl)-1H-1,2,4-triazol-3-yl)-pyridin-3-yl, 5-(1-cyclopropyl-5-(N-acetyl-piperidin-4-yl)-1H-1,2,4-triazol-3-yl)-pyridin-3-yl, 5-(1-isopropyl-5-(N-acetyl-piperidin-4-yl)-1H-1,2,4-triazol-3-yl)-pyridin-3-yl, or 5-(1-cyclopropyl-5-(1-hydroxy-1-methyl-ethyl)-1H-1,2,4-triazol-3-yl)-pyridin-3-yl;

or a pharmaceutically acceptable salt thereof.

8. A compound according to claim 1, wherein the asymmetric carbon atom bearing the hydroxy group has the absolute configuration depicted in Formula (II)

Formula (II)

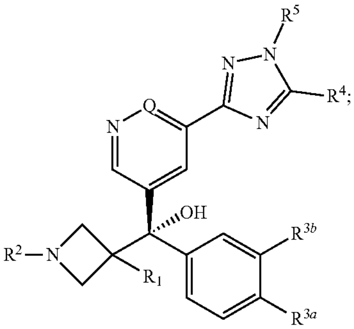

or a pharmaceutically acceptable salt thereof.

9. A compound according to claim 1, which is (R)-(4-Bromo-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol;

(R)-(4-tert-Butyl-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-[4-(1-trifluoromethyl-cyclopropyl)-phenyl]-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-trifluoromethoxy-phenyl)-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-[4-(2,2,2-trifluoro-ethyl)-phenyl]-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-ethyl-phenyl)-methanol;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-propyl-phenyl)-methanol;

trans-4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-cyclohexanol;

(R)-2-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-1,1,1-trifluoro-propan-2-ol;

4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-bicyclo[2.2.2]octane-1-carboxylic acid methyl ester;

(R)-{5-[1-Cyclopropyl-5-(1-methyl-1-methylamino-ethyl)-1H-[1,2,4]triazol-3-yl]-pyridin-3-yl}-(1,3-dimethyl-azetidin-3-yl)-(4-isopropyl-phenyl)-methanol;

1-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-ylmethyl)-cyclobutanol;

4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-bicyclo[2.2.2]octane-1-carboxylic acid;

(R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-Cyclohexyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-(1,3-Dimethyl-azetidin-3-yl)-(4-isopropyl-phenyl)-{5-[1-methyl-5-(tetrahydro-pyran-4-yl)-1H-[1,2,4]triazol-3-yl]-pyridin-3-yl}-methanol;

2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethanol;

(R)-(1,3-Dimethyl-azetidin-3-yl)-{5-[1-ethyl-5-(tetrahydro-pyran-4-yl)-1H-[1,2,4]triazol-3-yl]-pyridin-3-yl}-(4-isopropyl-phenyl)-methanol;

(R)-(1,3-Dimethyl-azetidin-3-yl)-(4-isopropyl-phenyl)-{5-[1-isopropyl-5-(tetrahydro-pyran-4-yl)-1H-[1,2,4]triazol-3-yl]-pyridin-3-yl}-methanol;

(R)-{5-[1-Cyclopentyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-tert-Butyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-(2,2-Difluoro-propyl)-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-{5-[1-Cyclobutyl-5-(tetrahydro-pyran-4-yl)-1H-[1,2,4]triazol-3-yl]-pyridin-3-yl}-(1,3-dimethyl-azetidin-3-yl)-(4-isopropyl-phenyl)-methanol;

(R)-[5-(1-Cyclopropyl-5-pyridin-3-yl-1H-[1,2,4]triazol-3-yl)-pyridin-3-yl]-(1,3-dimethyl-azetidin-3-yl)-(4-isopropyl-phenyl)-methanol;

(R)-(4-Cyclopropyl-phenyl)-{5-[1-cyclopropyl-5-(tetrahydro-pyran-4-yl)-1H-[1,2,4]triazol-3-yl]-pyridin-3-yl}-(1,3-dimethyl-azetidin-3-yl)-methanol;

2-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-propan-2-ol;

2-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-propan-2-ol;

(R)-{5-[1-Cyclopropyl-5-(3-hydroxymethyl-bicyclo[1.1.1]pent-1-yl)-1H-[1,2,4]triazol-3-yl]-pyridin-3-yl}-(1,3-dimethyl-azetidin-3-yl)-(4-isopropyl-phenyl)-methanol;

(R)-(1,3-Dimethyl-azetidin-3-yl)-{5-[5-(3-hydroxymethyl-bicyclo[1.1.1]pent-1-yl)-1-isopropyl-1H-[1,2,4]triazol-3-yl]-pyridin-3-yl}-(4-isopropyl-phenyl)-methanol;

4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-tetrahydro-pyran-4-ol;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-tetrahydro-pyran-4-ol;

1-[4-(2-Cyclopropyl-5-{5-[(R)-(1,3-dimethyl-azetidin-3-yl)-hydroxy-(4-isopropyl-phenyl)-methyl]-pyridin-3-yl}-2H-[1,2,4]triazol-3-yl)-piperidin-1-yl]-ethanone;

1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-1-yl]-ethanone;

(R)-{5-[1-Cyclopropyl-5-(tetrahydro-pyran-4-yl)-1H-[1,2,4]triazol-3-yl]-pyridin-3-yl}-(1-isopropyl-3-methyl-azetidin-3-yl)-(4-isopropyl-phenyl)-methanol;

(R)-{5-[1-Cyclopropyl-5-(tetrahydro-pyran-4-yl)-1H-[1,2,4]triazol-3-yl]-pyridin-3-yl}-[1-(2,2-difluoro-ethyl)-3-methyl-azetidin-3-yl]-(4-isopropyl-phenyl)-methanol;

2-{3-[(R)-{5-[1-Cyclopropyl-5-(tetrahydro-pyran-4-yl)-1H-[1,2,4]triazol-3-yl]-pyridin-3-yl}-hydroxy-(4-isopropyl-phenyl)-methyl]-3-methyl-azetidin-1-yl}-ethanol; or 2-(2-Cyclopropyl-5-{5-[(R)-hydroxy-(4-isopropyl-phenyl)-(3-methyl-azetidin-3-yl)-methyl]-pyridin-3-yl}-2H-[1,2,4]triazol-3-yl)-propan-2-ol;

or a pharmaceutically acceptable salt thereof.

10. A compound according to claim 1, which is (R)-{5-[1-Cyclopropyl-5-(tetrahydro-pyran-4-yl)-1H-[1,2,4]triazol-3-yl]-pyridin-3-yl}-(1,3-dimethyl-azetidin-3-yl)-(3-fluoro-4-isopropyl-phenyl)-methanol;

4-(2-Cyclopropyl-5-{5-[(R)-(1,3-dimethyl-azetidin-3-yl)-hydroxy-(4-isopropyl-phenyl)-methyl]-2-fluoro-pyridin-3-yl}-2H-[1,2,4]triazol-3-yl)-trans-cyclohexanol;

4-(2-Cyclopropyl-5-{5-[(R)-(1,3-dimethyl-azetidin-3-yl)-hydroxy-(4-isopropyl-phenyl)-methyl]-2-methyl-pyridin-3-yl}-2H-[1,2,4]triazol-3-yl)-trans-cyclohexanol;

(R)-(1,3-Dimethyl-azetidin-3-yl)-(4-isopropyl-phenyl)-[5-(1-isopropyl-5-propyl-1H-[1,2,4]triazol-3-yl)-pyridin-3-yl]-methanol;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-1-methyl-piperidin-2-one;

N-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-trans-cyclohexyl]-acetamide;

1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-1-yl]-2-hydroxy-ethanone;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-4-methyl-piperidin-2-one;

4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-piperidin-2-one;

1-[4-(5-{5-[(R)-(1,3-Dimethyl-azetidin-3-yl)-hydroxy-(4-isopropyl-phenyl)-methyl]-pyridin-3-yl}-2-isopropyl-2H-[1,2,4]triazol-3-yl)-4-hydroxy-piperidin-1-yl]-ethanone;

(R)-(1,3-Dimethyl-azetidin-3-yl)-(4-isopropyl-phenyl)-{5-[1-(2-methoxy-ethyl)-5-(tetrahydro-pyran-4-yl)-1H-[1,2,4]triazol-3-yl]-pyridin-3-yl}-methanol;

(R)-(1-Cyclopropyl-3-methyl-azetidin-3-yl)-{5-[1-cyclopropyl-5-(tetrahydro-pyran-4-yl)-1H-[1,2,4]triazol-3-yl]-pyridin-3-yl}-(4-isopropyl-phenyl)-methanol;

N-{2-[3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-[1,2,4]triazol-1-yl]-ethyl}-acetamide; or (R)-(1,3-Dimethyl-azetidin-3-yl)-(4-isopropyl-phenyl)-{6-[1-isopropyl-5-(tetrahydro-pyran-4-yl)-1H-[1,2,4]triazol-3-yl]-pyridazin-4-yl}-methanol;

or a pharmaceutically acceptable salt thereof.

11. A pharmaceutical composition comprising a compound according to claim 1 or a pharmaceutically acceptable salt thereof and further comprising at least one pharmaceutically acceptable carrier.

12. A method for the prevention or treatment of inflammatory/autoimmune diseases, conditions, or disorders; or cancer, said method comprising administering to a subject in need of said prevention or treatment a pharmaceutically active amount of a compound according to claim 1 or a pharmaceutically acceptable salt thereof.

13. A pharmaceutical composition comprising a compound according to claim 9 or a pharmaceutically acceptable salt thereof and further comprising at least one pharmaceutically acceptable carrier.

14. A pharmaceutical composition comprising a compound or a pharmaceutically acceptable salt thereof according to claim 10 and further comprising at least one pharmaceutically acceptable carrier.

15. A method for the prevention or treatment of inflammatory/autoimmune diseases, conditions, or disorders; or cancer, said method comprising administering to a subject in need of said prevention or treatment a pharmaceutically active amount of a compound according to claim 9 or a pharmaceutically acceptable salt thereof.

16. A method for the prevention or treatment of inflammatory/autoimmune diseases, conditions, or disorders; or cancer, said method comprising administering to a subject in need of said prevention or treatment a pharmaceutically active amount of a compound according to claim 10 or a pharmaceutically acceptable salt thereof.

* * * * *